US009856300B2

(12) United States Patent
Yang et al.

(10) Patent No.: US 9,856,300 B2
(45) Date of Patent: Jan. 2, 2018

(54) DPY-30 BINDING PEPTIDES AND METHODS OF USE

(71) Applicant: Marquette University, Milwaukee, WI (US)

(72) Inventors: Pinfen Yang, Milwaukee, WI (US); Priyanka Sivadas, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 0 days.

(21) Appl. No.: 15/185,299

(22) Filed: Jun. 17, 2016

(65) Prior Publication Data

US 2016/0297858 A1  Oct. 13, 2016

Related U.S. Application Data

(60) Continuation of application No. 14/531,570, filed on Nov. 3, 2014, now abandoned, which is a division of application No. 13/569,583, filed on Aug. 8, 2012, now Pat. No. 8,907,054.

(60) Provisional application No. 61/521,215, filed on Aug. 8, 2011.

(51) Int. Cl.
| | |
|---|---|
| *A61K 38/16* | (2006.01) |
| *C07K 14/47* | (2006.01) |
| *C07K 14/405* | (2006.01) |
| *C07K 7/08* | (2006.01) |
| *C07K 14/415* | (2006.01) |
| *C07K 7/06* | (2006.01) |
| *A61K 38/00* | (2006.01) |

(52) U.S. Cl.
CPC .............. *C07K 14/47* (2013.01); *C07K 7/06* (2013.01); *C07K 7/08* (2013.01); *C07K 14/405* (2013.01); *C07K 14/415* (2013.01); *A61K 38/00* (2013.01); *C07K 2319/10* (2013.01); *C07K 2319/21* (2013.01)

(58) Field of Classification Search
CPC .......... A61K 38/00; C07K 14/47; C07K 7/08; C07K 14/415; C07K 7/06; C07K 2319/10; C07K 14/405; C07K 2319/21
See application file for complete search history.

(56) References Cited

U.S. PATENT DOCUMENTS

| | | | |
|---|---|---|---|
| 5,595,756 A | 1/1997 | Bally et al. | |
| 2004/0236091 A1 | 11/2004 | Chicz et al. | |
| 2010/0125055 A1* | 5/2010 | Kufe ................. | A61K 38/1735 514/1.1 |

OTHER PUBLICATIONS

Hulme et al, Ligand binding assays at equilibrium: validation and interpretation, British Journal of Pharmacology, 2010, 161, pp. 1219-1237.*
Shaheen et al, Liposome as a Carrier for Advanced Drug Delivery, Pakistan Journal of Biological Sciences, 2006, 9, pp. 1181-1191.*
Hait, Anticancer drug development: the grand challenges, Nature Reviews/Drug Discovery, 2010, 9, pp. 253-254.*
Gravanis et al, The changing world of cancer drug development: the regulatory bodies' perspective, Chin Clin Oncol, 2014, 3, pp. 1-5.*
Alto et al., "Bioinformatic Design of A-kinase Anchoring Protein-in Silico: A Potent and Selective Peptide Antagonist of Type II Potein Kinase A Anchoring", Proceedings of the National Academy of Sciences, U.S.A., 2003, 100:4445-4450.
Angelo et al., "Molecular Characterization of an Anchor Protein (AKAPCE) that Binds the RI Subunit (RCE) of Type I Protein Knase A from Caenorhabditis Elegans", The Journal of Biological Chemistry, 1998, 273:14633-14643.
Barber et al., "Three-dimensional Structure of the Radial Spokes Reveals Heterogeneity and Interactions with Dyneins in Chlamydomonas Flagella", Molecular Biology of the Cell, 2003, 23:111-120.
Burns-Hamuro et al., "Designing Isoform-specific Peptide Disruptors of Protein Kinase A localization", Proceedings of the National Academy of Sciences, U S A., 2003, 100:4072-4077.
Cao et al., "An Ash2L/RbBP5 Heterodimer Stimulates the MLL1 Methyltransferase Activity Through Coordinated Substrate Interactions with the MLL1 Set Domain", Public Library of Science, 2010, 5:e14102.
Carr et al., "Interaction of the Regulatory Subunit (RII) of c-AMP Dependent Protein Kinase with RII-anchoring Proteins Occurs Through an Amphipathic Helix Binding Motif", The Journal of Biological Chemistry,1991, 266 (22)14188-14192.
Chen et al., "Crystal Structure of the N-terminal Region of Human Ash2L Shows a Winged-helix Motif Involved in DNA Binding", EMBO Reports, 2011,12:797-803.
Cho et al., "PTIP Associates with MLL3- and MLL4-Containing Histone H3 Lysine 4 Methyltransferase Complex", The Journal of Biological Chemistry, 2007, 282:20395-20406.
Diener et al., "Assembly of Flagellar Radial Spoke Proteins in Chlamydomonas: Identification of the Axoneme Binding Domain of Radial Spoke Protein 3", The Journal of Cell Biology, 1993, 123:183-190.
Fujita et al., "Ropporin, a Sperm Specific Binding Protein of Rhophilin that is Localized in the Fibrous Sheath of Sperm Flagella", The Journal of Cell Science, 2000, 113(Pt1):103-112.

(Continued)

*Primary Examiner* — Julie Ha
*Assistant Examiner* — Li Ni Komatsu
(74) *Attorney, Agent, or Firm* — Andrus Intellectual Property Law, LLP

(57) ABSTRACT

Disclosed are compositions and methods for modulating Dpy-30 binding activity. The compositions may include peptides or peptidomimetics thereof that are related to radial spoke protein 3 (RSP3) or absent, small, homeotic discs 2-like protein (Ash2L) and that bind to Dumpy-30 protein (Dpy-30).

7 Claims, 17 Drawing Sheets

(56) References Cited

OTHER PUBLICATIONS

Gaillard et al., "Flagellar Radial Spoke Protein 3 is an A-kinase Anchoring Protein (AKAP)", The Journal of Cell Biology, 2001, 153:443-448.
Gaillard et al., "Disruption of the A-kinase Anchoring Domain in Flagellar Radial Spoke Protein 3 Results in Unregulated Axonemal cAMP-dependent Protein Kinase Activity and Abnormal Flagellar Motility", Molecular Biology of the Cell, 2006, 17:2626-2635.
Gold et al., "Molecular Basis of AKAP Specificity for PKA Regulatory Subunits", Molecular Cell, 2006, 24:383-395.
Habermacher et al., "Regulation of Flagellar Dynein by an Axonemal type-1 Phosphatase in Chlamydomonas", Journal of Cell Science,1996, 109(Pt 7):1899-1907.
Habermacher et al., "Regulation of Flagellar Dynein by Phosphorylation of a 138-kD Inner Arm Dynein Intermediate Chain", The Journal of Cell Biology, 1997,136:167-176.
Hirsch et al., "Cloning and Expression of an Intron-less Gene for AKAP 75, an Anchor Protein for the Regulatory Subunit of cAMP-dependent Rotein Kinase II Beta", The Journal of Biological Chemistry, 1992, 267:2131-2134.
Howard et al., "Regulation of Chlamydomonas Flagellar Dynein by an Axonemal Protein Knase", The Journal of Cell Biology, 1994, 127:1683-1692.
Hsu et al., "The dpy-30 Gene Encodes an Essential Component of the Caenorhabditis Elegans Dosage Compensation Machinery", Genetics, 1994, 137:999-1018.
Huang et al., "Radial Spokes of Chlamydomonas Flagella: Genetic Analysis of Assembly and Function", Journal of Cell Biology, 1981, 88:80-88.
Huang et al., "D-AKAP2, A novel Protein Kinase A Anchoring Protein with a Putative RGS Domain", Proceedings of the National Academy of Sciences U S A., 1997, 94:11184-11189.
Huang et al., "Identification of a Novel Protein Kinase A Anchoring Protein that Binds Both Type I and Type II Regulatory Subunits", The Journal of Biological Chemistry, 1997, 272:8057-8064.
Jarnaess et al., "Dual Specificity A-kinase Anchoring Proteins (AKAPs) Contain an Additional Binding Region that Enhances Targeting of Protein Kinase A type I", The Journal of Biological Chemistry, 2008, 283:33708-33718.
Jiang et al., "Role for Dpy-30 in ES Cell-fate Specification by Regulation of H3K4 Methylation within Bivalent Domains", 2011, Cell, 144:513-525.
Kammerer et al., "Amino Acid Variant in the Kinase Binding Domain of Dual-specific A Kinase-Anchoring Protein 2: A Disease Susceptibility Polymorphism", Proceedings of the National Academy of Sciences U S A., 2003, 100:4066-4071.
Kinderman et al., "A Dynamic Mechanism for AKAP Binding to RII isoforms of cAMP-dependent Protein Kinase", Molecular Cell, 2006, 24:397-408.
Kindle et al., "High-frequency Nuclear Transformation of Chlamydomonas Reinhardtii", Proceedings of the National Academy of Sciences U S A., 1990, 87:1228-1232.
Li et al., "Protein kinase A-anchoring (AKAP) Domains in Brefeldin A-inhibited Guanine Nucleotide-exchange Protein 2 (BIG2)", Proceedings of the National Academy of Sciences U S A, 2003, 100:1627-1632.
Mak et al., A Lentiviral Functional Proteomics Approach Identifies Chromatin Remodeling Complexes Important for the Induction of Pluripotency, Molecular Cell Proteomics, 2010, 9:811-823.
Mastronarde et al., "Arrangement of Inner Dynein Arms in Wild-type and Mutant Flagella of Chlamydomonas", Journal of Cell Biology, 1992, 118:1145-1162.
Mauban et al., "AKAP-scaffolding Proteins and Regulation of Cardiac Physiology", Physiology (Bethesda), 2009, 24:78-87.
Means et al., "An Entirely Specific Type I A-kinase Anchoring Protein that can Sequester Two Molecules of Protein Kinase A at Mitochondria", Proceedings of the National Academy of Sciences USA, 2011, 108(48):E1227-1235.
Newlon et al., "A Novel Mechanism of PKA Anchoring Revealed by Solution Structures of Anchoring Complexes", EMBO Journal, 2001, 20:1651-1662.
Nicastro et al., "3D Structure of Eukaryotic Flagella in a Quiescent State Revealed by Cryo-electron Tomography", Proceedings of the National Academy of Sciences U S A, 2005, 102:15889-15894.
Omoto et al., "Rotation of the Central Pair Microtubules in Eukaryotic Flagella", Molecular Biology of the Cell, 1999, 10:1-4.
Patel et al., "On the Mechanism of Multiple Lysine Methylation by the Human Mixed Lineage Leukemia Protein-1 (MLL1) Core Complex", The Journal of Biological Chemistry, 2009, 284:24242-24256.
Patel-King et al., "Flagellar Radial Spokes Contain a Ca2+-stimulated Nucleoside Diphosphate Kinase", Molecular Biology of the Cell, 2004,15:3891-3902.
Pauling et al., "The Structure of Proteins; Two Hydrogen-bonded Helical Configurations of the Polypeptide Chain", Proceedings of the National Academy of Sciences U S A, 1951, 37:205-211.
Pferdehirt et al., "An MLL/Compass Subunit Functions in the C. elegans Dosage Compensation Complex to Target X Chromosomes for Transcriptional Regulation of Gene Expression", Genes & Development, 2011, 25:499-515.
Pigino et al., "Cryoelectron Tomography of Radial Spokes in Cilia and Flagella", The Journal of Cell Biology, 2011, 195(4):673-687.
Roguev et al., "The *Saccharomyces cerevisiae* Set1 Complex Includes an Ash2 Homologue and Methylates Histone 3 Lysine 4", EMBO Journal, 2001, 20:7137-7148.
Sarma et al., "Structure of D-AKAP2:PKA RI Complex: Insights into AKAP Specificity and Selectivity", Structure, 2010, 18:155-166.
Scott et al., "Cell Signaling in Space and Time: Where Proteins Come Together and When They're Apart", Science, 2009, 326:1220-1224.
Silflow et al., "The Vfl1 Protein in Chlamydomonas Localizes in a Rotationally Asymmetric Pattern at the Distal Ends of the Basal Bodies", The Journal of Cell Biology, 2001, 153:63-74.
Smith et al., "The Super Elongation Complex (SEC) and MLL in Development and Disease", Genes & Development, 2011, 25:661-672.
South et al., "A Cconserved Interaction Between the SDI Domain of Bre2 and the Dpy-30 Domain of Sdc1 is Required for Histone Methylation and Gene Expression", The Journal of Biological Chemistry, 2010, 285:595-607.
Southall et al., "Structural Basis for the Requirement of Additional Factors for MLL1 Set Domain Activity and Recognition of Epigenetic Marks", Molecular Cell, 2009, 33:181-191.
Stoller et al., "Ash2I Interacts with Tbx1 and is Required During Early Embryogenesis", Experimental Biology and Medicine (Maywood), 2010, 235:569-576.
Takahashi et al., "Structural Analysis of the Core Compass Family of Histone H3K4 Methylases from Yeast to Human", Proceedings of the National Academy of Sciences U S A., 2011, 108:20526-20531.
Wang et al., "Cloning and Mitochondrial Localization of Full-length D-AKAP2, a Protein Kinase A Anchoring Protein", Proceeding of the National Academy of Sciences U S A, 2001, 98:3220-3225.
Warner et al., "The Structural Basis of Ciliary Bend Formation. Radial Spoke Positional Changes Accompanying Microtubule Sliding", The Journal of Cell Biology, 1974, 63:35-63.
Tremblay, et al., Molecular Basis for DPY-30 Association to Compass-like and NURF Complexes, Structure, 2014, 22, pp. 1821-1830.
Simboeck, et al., DPY-30 Regulates Pathways in Cellular Senescence through ID Protein Expression, The EMBO Journal, 2013, 32, pp. 2217-2230.
Cancer Drug Design and Discovery. Neidle, Stephen, ed., Elsevier/ACademic Press, 2008, pp. 427-431.
Cellular and Molecular Basis of Cancer-Merck Manual, from http://www.merckmanuals.com/professional/print/hematology_and_oncology/overview . . . , pp. 1-5, accessed Nov. 7, 2012.
Sporn, et al., Chemoprevention of Cancer, Carcinogenesis, 2000, 21, pp. 525-530.
Yang et al., "Protein phosphatases PP1 and PP2A are located in distinct positions in the Chlamydomonas flagellar axoneme", Journal of Cell Science, 2000, 113:91-102.

(56) References Cited

OTHER PUBLICATIONS

"Written Description Training Materials" dated Mar. 25, 2008.
Avdic et al., "Structural and Biochemical Insights into MLL1 Core Complex Assembly", Structure, 2011, 19:101-8.
Banky et al., "Related Protein-Protein Interaction Modules Present Drastically Different Surface Topographies Despite a Conserved Helical Platform", J Mol Biol, 2003, 330:1117-29.
Beavo et al., "Cyclic Nucleotide Research—Still Expanding After Half a Century", Nat Rev Mol Cell Biol, 2002, 3:710-8.
Carr et al., "Identification of Sperm-Specific Proteins that Interact with A-Kinase Anchoring Proteins in a Manner Similar to the Type II Regulatory Subunit of PKA", J Biol Chem, 2001, 276:17332-8.
Carr et al., "Association of the Type II cAMP-Dependent Protein Kinase with a Human Thyroid RII-Anchoring Protein. Cloning and Characterization of the RII—~Binding Domain", J Biol Chem, 1992, 267:13376-82.
Chen et al., "Structure of the SPRY domain of human Ash2L and its interactions with RbBP5 and DPY30", Cell Research, 2012, 22:598-602.
Diener et al., "Sequential Assembly of Flagellar Radial Spokes", Cytoskeleton, 2011, 68(7):389-400.
Dong et al., "Characterization and Crystallization of Human DPY-30-Like Protein, an Essential Component of Dosage Compensation Complex", Biochim Biophys Acta, 2005,1753:257-62.
Dou et al., "Regulation of MLL1 H3K4 Methyltransferase Activity by its Core Components", Nat Struct Mol Biol, 2006, 3(8):713-9.
Gopal et al., "The DPY-30 domain and its flanking sequence mediate the assembly and modulation of flagellar radial spoke complexes", Molecular and Cellular Biology, Oct. 2012, 32(19):4012-4024.
Greengard et al., "Enhancement of the Glutamate Response by cAMP-Dependent Protein Kinase in Hippocampal Neurons", Science, 1991, 253:1135-8.
Gupta et al., "The versatile molecular complex component LC8 promotes several distinct steps of flagellar assembly", The Journal of Cell Biology, 2012, 198:115-126.
Hendrickson et al., IC138 is a WD-repeat dynein intermediate chain required for light chain assembly and regulation of flagellar bending, Molecular Biology of the Cell, 2004, 15:5431-5442.
Herberg et al., "Analysis of A-Kinase Anchoring Protein (AKAP) Interaction with Protein Kinase A (PKA) Regulatory Subunits: PKA Isoform Specificity in AKAP Binding", J Mol Biol, 2001, 298:329-39.
Kelekar et al., "Isolation and analysis of radial spoke protein", Chapter 12 of Cilia: Motors and Regulation, Methods in Cell Biology, 2009, 92:181.
Klauck et al., "Coordination of Three Signaling Enzymes by AKAP79, a Mammalian Scaffold Protein", Science, 1996, 271:1589-92.
Kohno et al., "Subunit Interactions within the Chlamydomonas Flagellar Spokehead", Cytoskeleton (Hoboken), 2011, 68:237-46.
Kovar et al., "Chlamydomonas reinhardtii produces a profilin with unusual biochemical properties", Journal of Cell Science, 2001, 114:4293-4305.
Lindemann, "The Geometric Clutch as a Working Hypothesis for Fture Research on Cilia and Flagella", Ann N Y Acad Sci, 2007, 1101:477-93.
Liu et al., "Human t-complex protein 11 (TCP11), a testis-specific gene product, is a potential determinant of the sperm morphology", Journal of Experimental Medicine, 2011, 224:111-117.
Merchant et al., "The Chlamydomonas genome reveals the evolution of key animal and plant functions", Science, 2007, 318 (5848):245-250.
Newell et al., "Protein Kinase A RII-like (R2D2) Proteins Exhibit Differential Localization and AKAP Interaction", Cell Motil Cytoskeleton, 2008, 65:539-52.
Nicastro et al., "3D Structure of Eukaryotic Flagella in a Quiescent State Revealed by Cryo-Electron Tomography", Proc Natl Acad Sci U S A, 2005,102:15889-94.

Patel et al., "Disruption of Protein Kinase A Localization Using a Trans-activator of Transcription (TAT)-conjugated A-Kinase-anchoring Peptide Reduces Cardiac Function", The Journal of Biological Chemistry, 2010, 285 (36):27632-27640.
Rual et al., "Towards a Proteome-Scale Map of the Human Protein-Protein Interaction Network", Nature, 2005, 437:1173-8.
Sarvan et al., "Crystal Structure of the Trithorax Group Protein ASH2L Reveals a Forkhead-Like DNA Binding Domain", Nat Struct Mol Biol, 2011,18:857-9.
Satir, "The Cilium as a Biological Nanomachine", Faseb Journal,1999,13(2):S235-7.
Sivadas et al., "A flagellar AKAP with two amphipathic helices form a structural scaffold in the radial spoke complex", Marquette University, Department of Biological Sciences, 2012, 1-43.
Sivadas et al., "A flagellar A-kinase anchoring protein with two amphipathic helices forms a structural scaffold in the radial spoke complex", The Journal of Cell Biology, 2012, 199(4):639-651.
Sivadas et al., "RIIa and Dpy-30 domains dock discrete effectors to two amphipathic helices in a flagellar AKAP", Marquette University, Department of Biological Sciences, 2012.
Smith et al., "The radial spokes and central apparatus: mechanochemical transducers that regulate flagellar motility", Cell Motil Cytoskeleton, 2004, 57(1):8-17.
Stelter et al., "Molecular Basis for the Functional Interaction of Dynein Light Chain with the Nuclear-Pore Complex", Nat Cell Biol, 2007, 9:788-96.
Steward et al., "Molecular Regulation of H3K4 Trimethylation by ASH2L, a Shared Subunit of MLL Complexes", Nat Struct Mol Biol, 2006,13(9):852-4.
Wang et al., "Crystal Structure of the C-Terminal Domain of Human DPY-30-Like Protein: A Component of the Histone Methyltransferase Complex", J Mol Biol, 2009, 390:530-7.
Welch et al., Networking with AKAPs: Context-dependent Regulation of Anchored Enzymes, Molecular Interventions, 2010, 10:86-97.
Wei et al., "Chlamydomonas Mutants Display Reversible Deficiencies in Flagellar Beating and Axonemal Assembly", Cytoskeleton (Hoboken), 2010, 67:71-80.
Williams et al., "Molecular Cloning and Sequence Analysis of the Chlamydomonas Gene Coding for Radial Spoke Protein 3: Flagellar Mutation pf-14 is an Ochre Allele", The Journal of Cell Biology, 1989,109:235-245.
Wirschell et al., "Building a Radial Spoke: Flagellar Radial Spoke Protein 3 (RSP3) is a Dimer", Cell Motil Cytoskeleton, 2008, 65:238-48.
Witman et al., "Chlamydomonas Flagellar Mutants Lacking Radial Spokes and Central Tubules. Structure, Composition, and Function of Specific Axonemal Components", The Journal of Cell Biology, 1978, 76:729-747.
Xia et al., "Modulation of Cell Adhesion and Migration by the Histone Methyltransferase Subunit mDpy-30 and its Interacting Proteins", PLoS One, 2010, 5:e11771.
Xu et al., "A Role of Histone H3 Lysine 4 Methyltransferase Components in Endosomal Trafficking", The Journal of Cell Biology, 2009, 186:343-353.
Yang et al., "Dimeric Heat Shock Protein 40 Binds Radial Spokes for Generating Coupled Power Strokes and Recovery Strokes of 9+2 Flagella", The Journal of Cell Biology, 2008, 180:403-415.
Yang et al., "The Flagellar Motility of Chlamydomonas pf25 Mutant Lacking an AKAP-binding Protein is Overtly Sensitive to Medium Conditions", Molecular Biology of the Cell, 2006, 17:227-238.
Yang et al., "Radial Spoke Proteins of Chlamydomonas Flagella", Journal of Cell Science, 2006, 119:1165-1174.
Yang et al., "Flagellar Radial Spoke Protein 2 is a Calmodulin Binding Protein Required for Motility in Chlamydomonas Reinhardtii", Eukaryotic Cell, 2006, 3: 72-81.
Yang et al., "Novel LC8 mutations have disparate effects on the assembly and stability of flagellar complexes", The Journal of Biological Chemistry, 2009, 284(45):31412-31421.
Yang et al, "The Mr 140,000 intermediate chain of *Chlamydomonas flagellar* inner arm dynein is a WD-repeat protein implicated in dynein arm anchoring", Molecular Biology of the Cell, 1998, 9:3335-3349.

(56) References Cited

OTHER PUBLICATIONS

Yang et al., "Dimeric novel HSP40 is incorporated into the radial spoke complex during the assembly process in flagella", Molecular Biology of the Cell, 2005, 16:637-648.
Yang et al., "Localization of calmodulin and dynein light chain LC8 in flagellar radial spokes", The Journal of Cell Biology, 2001, 153(6):1315-1325.
Yang et al., "Casein kinase I is anchored on axonemal doublet microtubules and regulates flagellar dynein phosphorylation and activity", The Journal of Biological Chemistry, 2000, 275(25):18905-18912.
Lee, et al., "Roles of DPY30 in the Proliferation and Motility of Gastric Cancer Cells", Plos One 2015, 10(7): 1-12.
Yang, et al., "The DPY30 subunit in SET1/MLL complexes regulates the proliferation and differentiation of hematopoietic progenitor cells", Blood 2014, 124(13): 2025-2033.
Zhang, et al., "Structural implications of DPY30 oligomerization for MLL/ SET1 Compass H3K4 trimethylation", Protein Cell 2015, 6(2): 147-151.

* cited by examiner

| | | | |
|---|---|---|---|
| (SEQ ID NO:56) | H.s. : | AQEELWKIAKMLSDVQQ | D-AKAP2 |
| (SEQ ID NO:57) | *C.r. : | ILEVIVGKVIEQGIMEVIEE | |
| (SEQ ID NO:58) | D.r. : | MLQVIVGKTIEQALLEVVEG | RSP3 |
| (SEQ ID NO:59) | H.s. : | VLEVIVGKTIEQSILEVVEE | |
| (SEQ ID NO:60) | H.s. : | LIEELASPIVDAVIEQIKAA | RII-AKAP |
| (SEQ ID NO:61) | C.e. : | ALYQFADRISELVISEANH | RI-AKAP |

RIIa-binding

| | | | |
|---|---|---|---|
| (SEQ ID NO:62) | *C.r. : | ARGVVRRVDKIEDAAA | |
| (SEQ ID NO:63) | D.r. : | EKRYVRMVIDMLQDVNQ | RSP3 |
| (SEQ ID NO:64) | H.s. : | EYSMVGRTVIDMLREVEK | |
| (SEQ ID NO:65) | S.c. : | DTLYKEIELIVWDIDE | Ash2 ? |
| (SEQ ID NO:66) | H.s. : | SDMCIGAVEHTADVIYH | |
| (SEQ ID NO:67) | H.s. : | PQDIVDNIVEEVVNIVGD | BIG1 ? |

Dpy-30-binding

D-AKAP2

RSP3-AH$_R$

RSP3-AH$_D$

|  |  |  |  |
|---|---|---|---|
| Ash2 | H.s. | GWGAVVEHTLADVLYHVETE | (SEQ ID NO:74) |
|  | D.r. | GWGAVIEHTLADLLYHVETE | (SEQ ID NO:75) |
|  | S.m. | VISAAVEQTVADIICLVEKD | (SEQ ID NO:76) |
|  | C.e. | ADEQQHEQTISDIIYLVSKE | (SEQ ID NO:77) |
|  | D.m. | VEELITEQCIADTLYLTEHD | (SEQ ID NO:78) |
|  | S.c. | YKEQIAEDIVWDLIDELEQI | (SEQ ID NO:79) |
| RSP3 | C.r. | ARGVVARRVIDKIVEDAIAA | (SEQ ID NO:62) |
|  | H.s. | EYSMVCRTVLDMAIREVVEK | (SEQ ID NO:64) |
| BIG1? | H.s. | PQDIVQNIVEEVVNIVVGD | (SEQ ID NO:67) |

B

|  |  | β or α0 / α1 |  |
|---|---|---|---|
| RIIα | M.m. | MGHIQI.PPGLTELLQGYTVEVLRQQ.. | (SEQ ID NO:80) |
| RIα | B.t. | SLRECELYVQKHNIQALLKDSIVQLCT | (SEQ ID NO:81) |
| Dpy | H.s. | LPTRAYLDQTVVPILLQGLAVLAKER.. | (SEQ ID NO:82) |
|  | D.r. | LPTRAYLDQTVVPILLQGLSVLAKER.. | (SEQ ID NO:83) |
|  | C.e. | VPTRQYLDSTVVPILLQGLGALAKDR.. | (SEQ ID NO:84) |
|  | S.c. | SQTEKYLNXNVTPHLLAGMRLIAVQQ.. | (SEQ ID NO:85) |
| Dpy/ DYDC | H.s. | -METNYLKRCFGNCLAQALAEVAKVR.. | (SEQ ID NO:86) |
|  | C.r. | -HDTAYLKETVGEALARGCAAAISAQ.. | (SEQ ID NO:87) |

SEQUENCE LISTING

<160> NUMBER OF SEQ ID NOS: 87

<210> SEQ ID NO 1
<211> LENGTH: 516
<212> TYPE: PRT
<213> ORGANISM: Chlamydomonas reinhardtii

<400> SEQUENCE: 1

Met Val Gln Ala Lys Ala Gln Gln Gln Leu Tyr Thr His Ala Ala Glu
1               5                   10                  15

Pro Lys Ala Val Gln Gln Arg Arg Ala Lys Tyr Arg Glu Asp Glu Thr
            20                  25                  30

Thr Gln Thr Leu Pro Thr Ala Asn Ile Met Phe Asp Arg Arg Val Val

```
            35                  40                  45
Arg Gly Asn Thr Tyr Ala Ala Arg Ile Leu Pro Ala Asp Ala Thr Gln
         50                  55                  60

Thr Gln Thr Lys Gly Pro Ser Pro Ala Ser Thr Lys Lys Arg Thr Thr
65                  70                  75                  80

Arg Thr Leu Pro Pro Arg Thr Pro Glu Ala Val Asp Gly Arg Arg His
                85                  90                  95

Ile Asp Ile Gln Thr Asp Val Tyr Leu Glu Glu Leu Thr Asp Thr Val
            100                 105                 110

Pro Glu Ala Asp Thr Ser Thr Gln Thr Asp Ala Phe Leu Asp Arg Pro
        115                 120                 125

Pro Thr Pro Leu Phe Val Pro Gln Lys Thr Gly Thr Asp Ala Ile Thr
    130                 135                 140

Gln Ile Glu Asn Gly Asp Leu Phe Asp Phe Asp Phe Glu Val Glu Pro
145                 150                 155                 160

Ile Leu Glu Val Leu Val Gly Lys Val Leu Glu Gln Gly Leu Met Glu
                165                 170                 175

Val Leu Glu Glu Glu Glu Leu Ala Ala Met Arg Ala His Gln Glu His
            180                 185                 190

Phe Glu Gln Ile Arg Asn Ala Glu Leu Val Ala Thr Gln Arg Met Glu
        195                 200                 205

Ala Ala Glu Arg Arg Lys Leu Glu Glu Lys Glu Arg Arg Met Gln Gln
    210                 215                 220

Glu Arg Glu Arg Val Glu Arg Glu Arg Val Val Arg Gln Lys Val Ala
225                 230                 235                 240

Ala Ser Ala Phe Ala Arg Gly Tyr Leu Ser Gly Ile Val Asn Thr Val
                245                 250                 255

Phe Asp Arg Leu Val Ser Ser Gly Tyr Ile Tyr Asp Pro Val Met Arg
            260                 265                 270

Glu Val Glu Thr Ala Phe Met Pro Trp Leu Lys Glu Gln Ala Ile Gly
        275                 280                 285

Tyr Leu Ala Arg Gly Val Val Ala Arg Arg Val Val Asp Lys Leu Val
    290                 295                 300

Glu Asp Ala Ala Ala Ala Leu Ala Ala Asn Arg Ser Thr Leu Ala Asp
305                 310                 315                 320

Lys Ala Ala Ser Thr Ala Ala Thr Val Asp Ala Trp Ala Glu Arg Gln
                325                 330                 335

Ala Lys Met Glu Ala Glu Leu Gln Gly Lys Glu Leu Glu Ala Val Arg
            340                 345                 350

Arg Arg Pro Thr Phe Val Leu Arg Glu Leu Lys Pro Ala Val Ala Ser
        355                 360                 365

Ala Asp Ala Val Glu Ala Ala Ala Glu Leu Thr Ala Gln Ala Glu
        370                 375                 380

Glu Ala Ala Asn Ala Lys Trp Glu Ala Asp Lys Ala Glu Ala Ala Glu
385                 390                 395                 400

Lys Ala Arg Ala Glu Ala Glu Ala Ala Glu Glu Gln Lys Ala Leu
                405                 410                 415

Leu Glu Glu Leu Ala Ala Thr Ala Ala Ala Glu Ala Glu Glu Arg Gly
            420                 425                 430

Glu Glu Pro Pro Ala Glu Pro Pro Ser Leu Pro Asp Gly Val Glu Pro
        435                 440                 445

Val Asp Val Glu Ala Glu Val Ala Lys Ala Val Glu Ala Val Pro Lys
450                 455                 460
```

```
Pro Pro Val Lys Glu Val Thr Asp Ile Asp Ile Leu Ser Tyr Met Met
465                 470                 475                 480

Asp Lys Gly Ala Ile Thr Lys Asp Ala Ile Ile Gln Ala Leu Ala Val
                485                 490                 495

His Ala Leu Gly Asp Lys Ala Tyr Thr Asn His Pro Ala Phe Ala Glu
            500                 505                 510

Ala Glu Gly Ala
        515

<210> SEQ ID NO 2
<211> LENGTH: 20
<212> TYPE: PRT
<213> ORGANISM: Chlamydomonas reinhardtii

<400> SEQUENCE: 2

Ala Arg Gly Val Val Ala Arg Val Val Asp Lys Leu Val Glu Asp
1               5                   10                  15

Ala Ala Ala Ala
        20

<210> SEQ ID NO 3
<211> LENGTH: 418
<212> TYPE: PRT
<213> ORGANISM: Homo sapiens

<400> SEQUENCE: 3

Met Ala Ser Ala Leu Thr Asp Arg Thr Ser Arg Ala Pro Ser Thr Tyr
1               5                   10                  15

Thr Tyr Thr Ser Arg Pro Arg Ala Leu Pro Cys Gln Arg Ser Arg Tyr
                20                  25                  30

Arg Asp Ser Leu Thr Gln Pro Asp Glu Pro Met His Tyr Gly Asn
            35                  40                  45

Ile Met Tyr Asp Arg Arg Val Ile Arg Gly Asn Thr Tyr Ala Leu Gln
    50                  55                  60

Thr Gly Pro Leu Leu Gly Arg Pro Asp Ser Leu Glu Leu Gln Arg Gln
65                  70                  75                  80

Arg Glu Ala Arg Lys Arg Ala Leu Ala Arg Lys Gln Ala Gln Glu Gln
                85                  90                  95

Leu Arg Pro Gln Thr Pro Glu Pro Val Glu Gly Arg Lys His Val Asp
            100                 105                 110

Val Gln Thr Glu Leu Tyr Leu Glu Glu Ile Ala Asp Arg Ile Ile Glu
        115                 120                 125

Val Asp Met Glu Cys Gln Thr Asp Ala Phe Leu Asp Arg Pro Pro Thr
130                 135                 140

Pro Leu Phe Ile Pro Ala Lys Thr Gly Lys Asp Val Ala Thr Gln Ile
145                 150                 155                 160

Leu Glu Gly Glu Leu Phe Asp Phe Asp Leu Glu Val Lys Pro Val Leu
                165                 170                 175

Glu Val Leu Val Gly Lys Thr Ile Glu Gln Ser Leu Leu Glu Val Met
            180                 185                 190

Glu Glu Glu Glu Leu Ala Asn Leu Arg Ala Ser Gln Arg Glu Tyr Glu
        195                 200                 205

Glu Leu Arg Asn Ser Glu Arg Ala Glu Val Gln Arg Leu Glu Glu Gln
    210                 215                 220

Glu Arg Arg His Arg Glu Glu Lys Glu Arg Arg Lys Lys Gln Gln Trp
225                 230                 235                 240
```

```
Glu Ile Met His Lys His Asn Glu Thr Ser Gln Lys Ile Ala Ala Arg
                245                 250                 255

Ala Phe Ala Gln Arg Tyr Leu Ala Asp Leu Leu Pro Ser Val Phe Gly
            260                 265                 270

Ser Leu Arg Asp Ser Gly Tyr Phe Tyr Asp Pro Ile Glu Arg Asp Ile
        275                 280                 285

Glu Ile Gly Phe Leu Pro Trp Leu Met Asn Glu Val Glu Lys Thr Met
    290                 295                 300

Glu Tyr Ser Met Val Gly Arg Thr Val Leu Asp Met Leu Ile Arg Glu
305                 310                 315                 320

Val Val Glu Lys Arg Leu Cys Met Tyr Glu His Gly Glu Asp Thr His
                325                 330                 335

Gln Ser Pro Glu Pro Glu Asp Glu Pro Gly Gly Pro Gly Ala Met Thr
            340                 345                 350

Glu Ser Leu Glu Ala Ser Glu Phe Leu Glu Gln Ser Met Ser Gln Thr
        355                 360                 365

Arg Glu Leu Leu Leu Asp Gly Gly Tyr Leu Gln Arg Thr Thr Tyr Asp
    370                 375                 380

Arg Arg Ser Ser Gln Glu Arg Lys Phe Met Glu Glu Arg Glu Leu Leu
385                 390                 395                 400

Gly Gln Asp Glu Glu Thr Ala Met Arg Lys Ser Leu Gly Glu Glu Glu
                405                 410                 415

Leu Ser

<210> SEQ ID NO 4
<211> LENGTH: 20
<212> TYPE: PRT
<213> ORGANISM: Homo sapiens

<400> SEQUENCE: 4

Glu Tyr Ser Met Val Gly Arg Thr Val Leu Asp Met Leu Ile Arg Glu
1               5                   10                  15

Val Val Glu Lys
            20

<210> SEQ ID NO 5
<211> LENGTH: 628
<212> TYPE: PRT
<213> ORGANISM: Homo sapiens

<400> SEQUENCE: 5

Met Ala Ala Ala Gly Ala Gly Pro Gly Gln Glu Ala Gly Ala Gly Pro
1               5                   10                  15

Gly Pro Gly Ala Val Ala Asn Ala Thr Gly Ala Glu Glu Gly Glu Met
            20                  25                  30

Lys Pro Val Ala Ala Gly Ala Ala Pro Pro Gly Glu Gly Ile Ser
        35                  40                  45

Ala Ala Pro Thr Val Glu Pro Ser Ser Gly Glu Ala Glu Gly Gly Glu
    50                  55                  60

Ala Asn Leu Val Asp Val Ser Gly Gly Leu Glu Thr Glu Ser Ser Asn
65                  70                  75                  80

Gly Lys Asp Thr Leu Glu Gly Ala Gly Asp Thr Ser Glu Val Met Asp
                85                  90                  95

Thr Gln Ala Gly Ser Val Asp Glu Glu Asn Gly Arg Gln Leu Gly Glu
            100                 105                 110
```

```
Val Glu Leu Gln Cys Gly Ile Cys Thr Lys Trp Phe Thr Ala Asp Thr
            115                 120                 125

Phe Gly Ile Asp Thr Ser Ser Cys Leu Pro Phe Met Thr Asn Tyr Ser
        130                 135                 140

Phe His Cys Asn Val Cys His His Ser Gly Asn Thr Tyr Phe Leu Arg
145                 150                 155                 160

Lys Gln Ala Asn Leu Lys Glu Met Cys Leu Ser Ala Leu Ala Asn Leu
                165                 170                 175

Thr Trp Gln Ser Arg Thr Gln Asp Glu His Pro Lys Thr Met Phe Ser
            180                 185                 190

Lys Asp Lys Asp Ile Ile Pro Phe Ile Asp Lys Tyr Trp Glu Cys Met
        195                 200                 205

Thr Thr Arg Gln Arg Pro Gly Lys Met Thr Trp Pro Asn Asn Ile Val
    210                 215                 220

Lys Thr Met Ser Lys Glu Arg Asp Val Phe Leu Val Lys Glu His Pro
225                 230                 235                 240

Asp Pro Gly Ser Lys Asp Pro Glu Glu Asp Tyr Pro Lys Phe Gly Leu
                245                 250                 255

Leu Asp Gln Asp Leu Ser Asn Ile Gly Pro Ala Tyr Asp Asn Gln Lys
            260                 265                 270

Gln Ser Ser Ala Val Ser Thr Ser Gly Asn Leu Asn Gly Gly Ile Ala
        275                 280                 285

Ala Gly Ser Ser Gly Lys Gly Arg Gly Ala Lys Arg Lys Gln Gln Asp
    290                 295                 300

Gly Gly Thr Thr Gly Thr Thr Lys Lys Ala Arg Ser Asp Pro Leu Phe
305                 310                 315                 320

Ser Ala Gln Arg Leu Pro Pro His Gly Tyr Pro Leu Glu His Pro Phe
                325                 330                 335

Asn Lys Asp Gly Tyr Arg Tyr Ile Leu Ala Glu Pro Asp Pro His Ala
            340                 345                 350

Pro Asp Pro Glu Lys Leu Glu Leu Asp Cys Trp Ala Gly Lys Pro Ile
        355                 360                 365

Pro Gly Asp Leu Tyr Arg Ala Cys Leu Tyr Glu Arg Val Leu Leu Ala
    370                 375                 380

Leu His Asp Arg Ala Pro Gln Leu Lys Ile Ser Asp Arg Leu Thr
385                 390                 395                 400

Val Val Gly Glu Lys Gly Tyr Ser Met Val Arg Ala Ser His Gly Val
                405                 410                 415

Arg Lys Gly Ala Trp Tyr Phe Glu Ile Thr Val Asp Glu Met Pro Pro
            420                 425                 430

Asp Thr Ala Ala Arg Leu Gly Trp Ser Gln Pro Leu Gly Asn Leu Gln
        435                 440                 445

Ala Pro Leu Gly Tyr Asp Lys Phe Ser Tyr Ser Trp Arg Ser Lys Lys
    450                 455                 460

Gly Thr Lys Phe His Gln Ser Ile Gly Lys His Tyr Ser Ser Gly Tyr
465                 470                 475                 480

Gly Gln Gly Asp Val Leu Gly Phe Tyr Ile Asn Leu Pro Glu Asp Thr
                485                 490                 495

Glu Thr Ala Lys Ser Leu Pro Asp Thr Tyr Lys Asp Lys Ala Leu Ile
            500                 505                 510

Lys Phe Lys Ser Tyr Leu Tyr Phe Glu Glu Lys Asp Phe Val Asp Lys
        515                 520                 525

Ala Glu Lys Ser Leu Lys Gln Thr Pro His Ser Glu Ile Ile Phe Tyr
```

```
                        530                 535                 540
Lys Asn Gly Val Asn Gln Gly Val Ala Tyr Lys Asp Ile Phe Glu Gly
545                 550                 555                 560

Val Tyr Phe Pro Ala Ile Ser Leu Tyr Lys Ser Cys Thr Val Ser Ile
                565                 570                 575

Asn Phe Gly Pro Cys Phe Lys Tyr Pro Pro Lys Asp Leu Thr Tyr Arg
            580                 585                 590

Pro Met Ser Asp Met Gly Trp Gly Ala Val Glu His Thr Leu Ala
        595                 600                 605

Asp Val Leu Tyr His Val Glu Thr Glu Val Asp Gly Arg Arg Ser Pro
    610                 615                 620

Pro Trp Glu Pro
625

<210> SEQ ID NO 6
<211> LENGTH: 20
<212> TYPE: PRT
<213> ORGANISM: Homo sapiens

<400> SEQUENCE: 6

Val Val Glu His Thr Leu Ala Asp Val Leu Tyr His Val Glu Thr Glu
1               5                   10                  15

Val Asp Gly Arg
            20

<210> SEQ ID NO 7
<211> LENGTH: 9
<212> TYPE: PRT
<213> ORGANISM: Human immunodeficiency virus type 1

<400> SEQUENCE: 7

Arg Lys Lys Arg Arg Gln Arg Arg Arg
1               5

<210> SEQ ID NO 8
<211> LENGTH: 11
<212> TYPE: PRT
<213> ORGANISM: Artificial
<220> FEATURE:
<223> OTHER INFORMATION: Synthesized peptide having protein transduction
      domain

<400> SEQUENCE: 8

Tyr Ala Arg Ala Ala Ala Arg Gln Ala Arg Ala
1               5                   10

<210> SEQ ID NO 9
<211> LENGTH: 12
<212> TYPE: PRT
<213> ORGANISM: Artificial
<220> FEATURE:
<223> OTHER INFORMATION: Synthesized peptide having protein transduction
      domain

<400> SEQUENCE: 9

Arg Arg Gln Arg Arg Thr Ser Lys Leu Met Lys Arg
1               5                   10

<210> SEQ ID NO 10
<211> LENGTH: 12
<212> TYPE: PRT
<213> ORGANISM: Artificial
<220> FEATURE:
```

```
<223> OTHER INFORMATION: Synthesized peptide having protein transduction
      domain

<400> SEQUENCE: 10

Ala Ala Val Leu Leu Pro Val Leu Leu Ala Ala Arg
1               5                   10

<210> SEQ ID NO 11
<211> LENGTH: 9
<212> TYPE: PRT
<213> ORGANISM: Artificial
<220> FEATURE:
<223> OTHER INFORMATION: Synthesized peptide having protein transduction
      domain

<400> SEQUENCE: 11

Arg Arg Arg Arg Arg Arg Arg Arg Arg
1               5

<210> SEQ ID NO 12
<211> LENGTH: 9
<212> TYPE: PRT
<213> ORGANISM: Artificial
<220> FEATURE:
<223> OTHER INFORMATION: Synthesized peptide having protein transduction
      domain

<400> SEQUENCE: 12

Ser Gly Trp Phe Arg Arg Trp Lys Lys
1               5

<210> SEQ ID NO 13
<211> LENGTH: 16
<212> TYPE: PRT
<213> ORGANISM: Homo sapiens

<400> SEQUENCE: 13

Arg Gln Ile Lys Ile Trp Phe Gln Asn Arg Arg Met Lys Trp Lys Lys
1               5                   10                  15

<210> SEQ ID NO 14
<211> LENGTH: 31
<212> TYPE: DNA
<213> ORGANISM: Artificial
<220> FEATURE:
<223> OTHER INFORMATION: Synthesized oligonucleotide for amplifying
      Chlamydomona reinhardtii RSP3 gene

<400> SEQUENCE: 14
tccaactcta catctagagc tcgcagagag g                                    31

<210> SEQ ID NO 15
<211> LENGTH: 34
<212> TYPE: DNA
<213> ORGANISM: Artificial
<220> FEATURE:
<223> OTHER INFORMATION: Synthesized oligonucleotide for amplifying
      Chlamydomona reinhardtii RSP3 gene

<400> SEQUENCE: 15
tctccatcag gccctgctcg agcaccttgc ccac                                 34

<210> SEQ ID NO 16
<211> LENGTH: 31
<212> TYPE: DNA
<213> ORGANISM: Artificial
<220> FEATURE:
```

```
<223> OTHER INFORMATION: Synthesized oligonucleotide for amplifying
      Chlamydomona reinhardtii RSP3 gene

<400> SEQUENCE: 16
tctcgagctg tctggcattg tcaacacggt g                                    31

<210> SEQ ID NO 17
<211> LENGTH: 26
<212> TYPE: DNA
<213> ORGANISM: Artificial
<220> FEATURE:
<223> OTHER INFORMATION: Synthesized oligonucleotide for amplifying
      Chlamydomona reinhardtii RSP3 gene

<400> SEQUENCE: 17
tcttgtccgc ctcccacttg gcgttg                                          26

<210> SEQ ID NO 18
<211> LENGTH: 27
<212> TYPE: DNA
<213> ORGANISM: Artificial
<220> FEATURE:
<223> OTHER INFORMATION: Synthesized oligonucleotide for amplifying
      Chlamydomona reinhardtii RSP3 gene

<400> SEQUENCE: 18
ccgcaagctc actcgttcac cataaac                                         27

<210> SEQ ID NO 19
<211> LENGTH: 33
<212> TYPE: DNA
<213> ORGANISM: Artificial
<220> FEATURE:
<223> OTHER INFORMATION: Synthesized oligonucleotide for amplifying
      Chlamydomona reinhardtii RSP3 gene

<400> SEQUENCE: 19
agcggccgcg cgattggctg ccagcgccgc cgc                                  33

<210> SEQ ID NO 20
<211> LENGTH: 34
<212> TYPE: DNA
<213> ORGANISM: Artificial
<220> FEATURE:
<223> OTHER INFORMATION: Synthesized oligonucleotide for amplifying
      Chlamydomona reinhardtii RSP3 gene

<400> SEQUENCE: 20
ggaattcccg ctctgctctc cagtccgact aggg                                 34

<210> SEQ ID NO 21
<211> LENGTH: 35
<212> TYPE: DNA
<213> ORGANISM: Artificial
<220> FEATURE:
<223> OTHER INFORMATION: Synthesized oligonucleotide for amplifying
      Chlamydomona reinhardtii RSP3 gene

<400> SEQUENCE: 21
gctctagact cctcctcctc cagcacctcc atcag                                35

<210> SEQ ID NO 22
<211> LENGTH: 33
<212> TYPE: DNA
<213> ORGANISM: Artificial
<220> FEATURE:
<223> OTHER INFORMATION: Synthesized oligonucleotide for amplifying
```

Chlamydomona reinhardtii RSP3 gene

<400> SEQUENCE: 22
gctctagacg ccagggtgct gcgattggct gcc                33

<210> SEQ ID NO 23
<211> LENGTH: 33
<212> TYPE: DNA
<213> ORGANISM: Artificial
<220> FEATURE:
<223> OTHER INFORMATION: Synthesized oligonucleotide for amplifying
      Chlamydomona reinhardtii RSP3 gene

<400> SEQUENCE: 23
ggaattctgt tgcctgagag ctccgcctcg gcc                33

<210> SEQ ID NO 24
<211> LENGTH: 33
<212> TYPE: DNA
<213> ORGANISM: Artificial
<220> FEATURE:
<223> OTHER INFORMATION: Synthesized oligonucleotide for amplifying
      Chlamydomona reinhardtii RSP3 gene

<400> SEQUENCE: 24
gctctagagc cgcgcgcaaa ggcgctggcc gcc                33

<210> SEQ ID NO 25
<211> LENGTH: 33
<212> TYPE: DNA
<213> ORGANISM: Artificial
<220> FEATURE:
<223> OTHER INFORMATION: Synthesized oligonucleotide for amplifying
      Chlamydomona reinhardtii RSP3 gene

<400> SEQUENCE: 25
gctctagacg ccagggtgct gcgattggct gcc                33

<210> SEQ ID NO 26
<211> LENGTH: 29
<212> TYPE: DNA
<213> ORGANISM: Artificial
<220> FEATURE:
<223> OTHER INFORMATION: Synthesized oligonucleotide for amplifying
      Chlamydomona reinhardtii RSP3 gene

<400> SEQUENCE: 26
acctcgaggg ggtcgtagat gtagccgct                     29

<210> SEQ ID NO 27
<211> LENGTH: 38
<212> TYPE: DNA
<213> ORGANISM: Artificial
<220> FEATURE:
<223> OTHER INFORMATION: Synthesized oligonucleotide for amplifying
      Chlamydomona reinhardtii RSP3 gene

<400> SEQUENCE: 27
acctcgagca ccaccaccac caccactaag ctagaggg           38

<210> SEQ ID NO 28
<211> LENGTH: 31
<212> TYPE: PRT
<213> ORGANISM: Homo sapiens

<400> SEQUENCE: 28

Pro Met Ser Asp Met Gly Trp Gly Ala Val Val Glu His Thr Leu Ala
1               5                   10                  15

Asp Val Leu Tyr His Val Glu Thr Glu Val Asp Gly Arg Arg Ser
            20                  25                  30

<210> SEQ ID NO 29
<211> LENGTH: 25
<212> TYPE: PRT
<213> ORGANISM: Homo sapiens

<400> SEQUENCE: 29

Pro Met Ser Asp Met Gly Trp Gly Ala Val Val Glu His Thr Leu Ala
1               5                   10                  15

Asp Val Leu Tyr His Val Glu Thr Glu
            20                  25

<210> SEQ ID NO 30
<211> LENGTH: 31
<212> TYPE: PRT
<213> ORGANISM: Artificial
<220> FEATURE:
<223> OTHER INFORMATION: Modified fragment of Homo sapiens Ash2L
      polypeptide

<400> SEQUENCE: 30

Pro Met Ser Asp Met Gly Pro Gly Ala Val Val Glu His Thr Leu Ala
1               5                   10                  15

Asp Val Leu Tyr His Val Glu Thr Glu Val Asp Gly Arg Arg Ser
            20                  25                  30

<210> SEQ ID NO 31
<211> LENGTH: 25
<212> TYPE: PRT
<213> ORGANISM: Artificial
<220> FEATURE:
<223> OTHER INFORMATION: Modified fragment of Homo sapiens Ash2L
      polypeptide

<400> SEQUENCE: 31

Pro Met Ser Asp Met Gly Trp Gly Ala Val Val Glu His Thr Leu Ala
1               5                   10                  15

Asp Val Leu Tyr His Gly Arg Arg Ser
            20                  25

<210> SEQ ID NO 32
<211> LENGTH: 21
<212> TYPE: PRT
<213> ORGANISM: Artificial
<220> FEATURE:
<223> OTHER INFORMATION: Modified fragment of Homo sapiens Ash2L
      polypeptide

<400> SEQUENCE: 32

Pro Met Ser Asp Met Gly Trp Gly Ala Val Val Glu His Thr Leu Ala
1               5                   10                  15

Asp Gly Arg Arg Ser
            20

<210> SEQ ID NO 33
<211> LENGTH: 31
<212> TYPE: PRT
<213> ORGANISM: Artificial
<220> FEATURE:
<223> OTHER INFORMATION: Modified fragment of Homo sapiens Ash2L
      polypeptide

<400> SEQUENCE: 33

Pro Met Ser Asp Met Gly Trp Gly Ala Val Val Lys His Thr Leu Ala
1               5                   10                  15

Asp Val Leu Tyr His Val Glu Thr Glu Val Asp Gly Arg Arg Ser
            20                  25                  30

<210> SEQ ID NO 34
<211> LENGTH: 6
<212> TYPE: PRT
<213> ORGANISM: Homo sapiens

<400> SEQUENCE: 34

Val Glu Thr Glu Val Asp
1               5

<210> SEQ ID NO 35
<211> LENGTH: 4
<212> TYPE: PRT
<213> ORGANISM: Homo sapiens

<400> SEQUENCE: 35

Val Glu Thr Glu
1

<210> SEQ ID NO 36
<211> LENGTH: 4
<212> TYPE: PRT
<213> ORGANISM: Homo sapiens

<400> SEQUENCE: 36

Val Val Glu His
1

<210> SEQ ID NO 37
<211> LENGTH: 29
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 37
cccatatgga gccagagcag atgctggag                                    29

<210> SEQ ID NO 38
<211> LENGTH: 33
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 38
gcctcgagtc agtttcgatc ttcaaactgt gcc                               33

<210> SEQ ID NO 39
<211> LENGTH: 33
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 39

```
gctgcagaag gtagatctcc agtctttgcc aac                                    33

<210> SEQ ID NO 40
<211> LENGTH: 32
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 40
ggctagctca gtttcgatct tcaaactgtg cc                                     32

<210> SEQ ID NO 41
<211> LENGTH: 27
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 41
accatatggg ccacatccag atcccgc                                           27

<210> SEQ ID NO 42
<211> LENGTH: 37
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 42
acctcgagct agctggactc ctgcgtgtga aaggtcg                                37

<210> SEQ ID NO 43
<211> LENGTH: 25
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 43
accatatggc ttccggcacc accgc                                             25

<210> SEQ ID NO 44
<211> LENGTH: 35
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 44
acctcgagct attcatcctc ccgagagtct gcacg                                  35

<210> SEQ ID NO 45
<211> LENGTH: 31
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 45
gcccatggag tccctatac taggttattg g                                       31
```

<210> SEQ ID NO 46
<211> LENGTH: 26
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 46 ggggatcca cgcggaacca gatccg                                              26

<210> SEQ ID NO 47
<211> LENGTH: 42
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 47
ctggttccgc gtggatcccc ccctatgagt gacatgggct gg                           42

<210> SEQ ID NO 48
<211> LENGTH: 31
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 48
aatgcattca actgcgcctc ccatccactt c                                       31

<210> SEQ ID NO 49
<211> LENGTH: 31
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 49
gtatcacgtg gagacagaat aagatgggag g                                       31

<210> SEQ ID NO 50
<211> LENGTH: 37
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 50
cctatgagtg acatgggccc gggcgccgtg gtagagc                                 37

<210> SEQ ID NO 51
<211> LENGTH: 27
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 51
ggatactcac tgtacccggg cccgcgg                                            27

```
<210> SEQ ID NO 52
<211> LENGTH: 30
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 52
gcgccgtggt aaagcacacc ctggctgacg                                     30

<210> SEQ ID NO 53
<211> LENGTH: 43
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 53
ctggctgacg tcttgtatca cgggaggcgc agttgaatgc agg                      43

<210> SEQ ID NO 54
<211> LENGTH: 41
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 54
ggtagagcac accctggctg acgggaggcg cagttgaatg c                        41

<210> SEQ ID NO 55
<211> LENGTH: 18
<212> TYPE: DNA
<213> ORGANISM: Artificial
<220> FEATURE:
<223> OTHER INFORMATION: Synthesized oligonucleotide for amplifying Homo
      sapiens Ash2L gene

<400> SEQUENCE: 55
gcccatgtca ctcatagg                                                  18

<210> SEQ ID NO 56
<211> LENGTH: 20
<212> TYPE: PRT
<213> ORGANISM: Homo sapiens

<400> SEQUENCE: 56

Ala Gln Glu Glu Leu Ala Trp Lys Ile Ala Lys Met Ile Val Ser Asp
1               5                   10                  15

Val Met Gln Gln
            20

<210> SEQ ID NO 57
<211> LENGTH: 20
<212> TYPE: PRT
<213> ORGANISM: Chlamydomonas reinhardtii

<400> SEQUENCE: 57

Ile Leu Glu Val Leu Val Gly Lys Val Leu Glu Gln Gly Leu Met Glu
1               5                   10                  15

Val Leu Glu Glu
            20
```

<210> SEQ ID NO 58
<211> LENGTH: 20
<212> TYPE: PRT
<213> ORGANISM: Danio rerio

<400> SEQUENCE: 58

Met Leu Gln Val Leu Val Gly Lys Thr Ile Glu Gln Ala Leu Leu Glu
1               5                   10                  15

Val Met Glu Gly
            20

<210> SEQ ID NO 59
<211> LENGTH: 20
<212> TYPE: PRT
<213> ORGANISM: Homo sapiens

<400> SEQUENCE: 59

Val Leu Glu Val Leu Val Gly Lys Thr Ile Glu Gln Ser Leu Leu Glu
1               5                   10                  15

Val Met Glu Glu
            20

<210> SEQ ID NO 60
<211> LENGTH: 20
<212> TYPE: PRT
<213> ORGANISM: Homo sapiens

<400> SEQUENCE: 60

Leu Ile Glu Glu Ala Ala Ser Arg Ile Val Asp Ala Val Ile Glu Gln
1               5                   10                  15

Val Lys Ala Ala
            20

<210> SEQ ID NO 61
<211> LENGTH: 20
<212> TYPE: PRT
<213> ORGANISM: Caenorhabditis elegans

<400> SEQUENCE: 61

Ala Leu Tyr Gln Phe Ala Asp Arg Phe Ser Glu Leu Val Ile Ser Glu
1               5                   10                  15

Ala Leu Asn His
            20

<210> SEQ ID NO 62
<211> LENGTH: 20
<212> TYPE: PRT
<213> ORGANISM: Chlamydomonas reinhardtii

<400> SEQUENCE: 62

Ala Arg Gly Val Val Ala Arg Arg Val Val Asp Lys Leu Val Glu Asp
1               5                   10                  15

Ala Ala Ala Ala
            20

<210> SEQ ID NO 63
<211> LENGTH: 20
<212> TYPE: PRT
<213> ORGANISM: Danio rerio

<400> SEQUENCE: 63

Glu Lys Arg Tyr Val Ala Arg Met Val Leu Asp Met Leu Ile Gln Asp
1               5                   10                  15

Val Thr Asn Gln
            20

<210> SEQ ID NO 64
<211> LENGTH: 20
<212> TYPE: PRT
<213> ORGANISM: Homo sapiens

<400> SEQUENCE: 64

Glu Tyr Ser Met Val Gly Arg Thr Val Leu Asp Met Leu Ile Arg Glu
1               5                   10                  15

Val Val Glu Lys
            20

<210> SEQ ID NO 65
<211> LENGTH: 19
<212> TYPE: PRT
<213> ORGANISM: Saccharomyces cerevisiae

<400> SEQUENCE: 65

Asp Thr Leu Tyr Lys Glu Gln Ile Ala Glu Ile Val Trp Asp Ile
1               5                   10                  15

Ile Asp Glu

<210> SEQ ID NO 66
<211> LENGTH: 19
<212> TYPE: PRT
<213> ORGANISM: Homo sapiens

<400> SEQUENCE: 66

Ser Asp Met Gly Trp Gly Ala Val Val Glu His Thr Leu Ala Asp Val
1               5                   10                  15

Leu Tyr His

<210> SEQ ID NO 67
<211> LENGTH: 19
<212> TYPE: PRT
<213> ORGANISM: Homo sapiens

<400> SEQUENCE: 67

Pro Gln Asp Ile Val Gln Asn Ile Val Glu Glu Met Val Asn Ile Val
1               5                   10                  15

Val Gly Asp

<210> SEQ ID NO 68
<211> LENGTH: 43
<212> TYPE: PRT
<213> ORGANISM: Homo sapiens

<400> SEQUENCE: 68

Pro Lys Asp Leu Thr Tyr Arg Pro Met Ser Asp Met Gly Trp Gly Ala
1               5                   10                  15

Val Val Glu His Thr Leu Ala Asp Val Leu Tyr His Val Glu Thr Glu
            20                  25                  30

Val Asp Gly Arg Arg Ser Pro Pro Trp Glu Pro
        35                  40

<210> SEQ ID NO 69
<211> LENGTH: 43

<212> TYPE: PRT
<213> ORGANISM: Danio rerio

<400> SEQUENCE: 69

Pro Lys Asp Ile Lys Phe Gln Pro Met Ser Asp Met Gly Trp Gly Ala
1               5                   10                  15

Val Ile Glu His Thr Leu Ala Asp Met Leu Tyr His Val Glu Thr Glu
            20                  25                  30

Val Asp Gly Arg Arg Ser Pro Gln Tyr Glu Gly
        35                  40

<210> SEQ ID NO 70
<211> LENGTH: 48
<212> TYPE: PRT
<213> ORGANISM: Schistosoma mansoni

<400> SEQUENCE: 70

Pro Ser Asp Ile Thr Asp Trp Glu Pro Met Ser Ser Arg Val Ile Ser
1               5                   10                  15

Ala Ala Val Glu Gln Thr Val Ala Asp Met Ile Cys Leu Val Glu Lys
            20                  25                  30

Asp Gly Phe Ile Glu Arg Thr Ile Lys Ser Cys Thr Pro Gln Phe Asn
        35                  40                  45

<210> SEQ ID NO 71
<211> LENGTH: 45
<212> TYPE: PRT
<213> ORGANISM: Caenorhabditis elegans

<400> SEQUENCE: 71

Pro Arg Gly Ala Thr Gly Ile His Ala Arg Ala Asp Glu Gln Gln His
1               5                   10                  15

Glu Gln Thr Leu Ser Asp Met Leu Tyr Leu Val Ser Lys Glu Val Asn
            20                  25                  30

Leu Asp His Pro Pro Arg Val Lys Arg Glu Asp Asp
        35                  40                  45

<210> SEQ ID NO 72
<211> LENGTH: 45
<212> TYPE: PRT
<213> ORGANISM: Drosophila melanogaster

<400> SEQUENCE: 72

Pro Glu Val Leu Val Glu His Lys Ala Lys Gly Met His Asp Arg Val
1               5                   10                  15

Glu Glu Leu Ile Thr Glu Gln Cys Leu Ala Asp Thr Leu Tyr Leu Thr
            20                  25                  30

Glu His Asp Gly Arg Leu Arg Leu Asp Asn Met Gly Leu
        35                  40                  45

<210> SEQ ID NO 73
<211> LENGTH: 45
<212> TYPE: PRT
<213> ORGANISM: Saccharomyces cerevisiea

<400> SEQUENCE: 73

Asp Gln Ile Arg Ser Ala Tyr Cys Val Asp Gly Asn Ser Lys Val Asn
1               5                   10                  15

Thr Leu Asp Thr Leu Tyr Lys Glu Gln Ile Ala Glu Asp Ile Val Trp
            20                  25                  30

-continued

Asp Ile Ile Asp Glu Leu Glu Gln Ile Ala Leu Gln Gln
        35                  40                  45

<210> SEQ ID NO 74
<211> LENGTH: 20
<212> TYPE: PRT
<213> ORGANISM: Homo sapiens

<400> SEQUENCE: 74

Gly Trp Gly Ala Val Val Glu His Thr Leu Ala Asp Val Leu Tyr His
1               5                   10                  15

Val Glu Thr Glu
            20

<210> SEQ ID NO 75
<211> LENGTH: 20
<212> TYPE: PRT
<213> ORGANISM: Danio rerio

<400> SEQUENCE: 75

Gly Trp Gly Ala Val Ile Glu His Thr Leu Ala Asp Met Leu Tyr His
1               5                   10                  15

Val Glu Thr Glu
            20

<210> SEQ ID NO 76
<211> LENGTH: 20
<212> TYPE: PRT
<213> ORGANISM: Schistosoma mansoni

<400> SEQUENCE: 76

Val Ile Ser Ala Ala Val Glu Gln Thr Val Ala Asp Met Ile Cys Leu
1               5                   10                  15

Val Glu Lys Asp
            20

<210> SEQ ID NO 77
<211> LENGTH: 20
<212> TYPE: PRT
<213> ORGANISM: Caenorhabditis elegans

<400> SEQUENCE: 77

Ala Asp Glu Gln Gln His Glu Gln Thr Leu Ser Asp Met Leu Tyr Leu
1               5                   10                  15

Val Ser Lys Glu
            20

<210> SEQ ID NO 78
<211> LENGTH: 20
<212> TYPE: PRT
<213> ORGANISM: Drosophila melanogaster

<400> SEQUENCE: 78

Val Glu Glu Leu Ile Thr Glu Gln Cys Leu Ala Asp Thr Leu Tyr Leu
1               5                   10                  15

Thr Glu His Asp
            20

<210> SEQ ID NO 79
<211> LENGTH: 20
<212> TYPE: PRT
<213> ORGANISM: Saccharomyces cerevisiea -continued

```
<400> SEQUENCE: 79

Tyr Lys Glu Gln Ile Ala Glu Asp Ile Val Trp Asp Ile Ile Asp Glu
1               5                   10                  15

Leu Glu Gln Ile
            20

<210> SEQ ID NO 80
<211> LENGTH: 25
<212> TYPE: PRT
<213> ORGANISM: Mus musculus

<400> SEQUENCE: 80

Met Gly His Ile Gln Ile Pro Pro Gly Leu Thr Glu Leu Leu Gln Gly
1               5                   10                  15

Tyr Thr Val Glu Val Leu Arg Gln Gln
            20                  25

<210> SEQ ID NO 81
<211> LENGTH: 27
<212> TYPE: PRT
<213> ORGANISM: Bos taurus

<400> SEQUENCE: 81

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr
            20                  25

<210> SEQ ID NO 82
<211> LENGTH: 26
<212> TYPE: PRT
<213> ORGANISM: Homo sapiens

<400> SEQUENCE: 82

Leu Pro Thr Arg Ala Tyr Leu Asp Gln Thr Val Val Pro Ile Leu Leu
1               5                   10                  15

Gln Gly Leu Ala Val Leu Ala Lys Glu Arg
            20                  25

<210> SEQ ID NO 83
<211> LENGTH: 26
<212> TYPE: PRT
<213> ORGANISM: Danio rerio

<400> SEQUENCE: 83

Leu Pro Thr Arg Ala Tyr Leu Asp Gln Thr Val Val Pro Ile Leu Leu
1               5                   10                  15

Gln Gly Leu Ser Val Leu Ala Lys Glu Arg
            20                  25

<210> SEQ ID NO 84
<211> LENGTH: 26
<212> TYPE: PRT
<213> ORGANISM: Caenorhabditis elegans

<400> SEQUENCE: 84

Val Pro Thr Arg Gln Tyr Leu Asp Ser Thr Val Val Pro Ile Leu Leu
1               5                   10                  15

Gln Gly Leu Gly Ala Leu Ala Lys Asp Arg
            20                  25
```

```
<210> SEQ ID NO 85
<211> LENGTH: 26
<212> TYPE: PRT
<213> ORGANISM: Saccharomyces cerevisiae
<220> FEATURE:
<221> NAME/KEY: misc_feature
<222> LOCATION: (9)..(9)
<223> OTHER INFORMATION: Xaa can be any naturally occurring amino acid

<400> SEQUENCE: 85

Ser Gln Thr Arg Lys Tyr Leu Asn Xaa Asn Val Thr Pro His Leu Leu
1               5                  10                  15

Ala Gly Met Arg Leu Ile Ala Val Gln Gln
            20                  25

<210> SEQ ID NO 86
<211> LENGTH: 25
<212> TYPE: PRT
<213> ORGANISM: Homo sapiens

<400> SEQUENCE: 86

Met Glu Thr Asn Tyr Leu Lys Arg Cys Phe Gly Asn Cys Leu Ala Gln
1               5                  10                  15

Ala Leu Ala Glu Val Ala Lys Val Arg
            20                  25

<210> SEQ ID NO 87
<211> LENGTH: 25
<212> TYPE: PRT
<213> ORGANISM: Chlamydomonas reinhardtii

<400> SEQUENCE: 87

His Asp Thr Ala Tyr Leu Lys Glu Thr Val Gly Glu Ala Leu Ala Arg
1               5                  10                  15

Gly Cys Ala Ala Ala Ile Ser Ala Gln
            20                  25
```

DPY-30 BINDING PEPTIDES AND METHODS OF USE

CROSS-REFERENCE TO RELATED PATENT APPLICATIONS

This application is a continuation of U.S. application Ser. No. 14/531,570, filed on Nov. 3, 2014, which published on Mar. 12, 2015, as U.S. Publication No. 2015/0072941, now abandoned, and is a divisional application of U.S. application Ser. No. 13/569,583, filed on Aug. 8, 2012, which application published on Aug. 22, 2013, as U.S. Publication No. 2013/0217613, now issued as U.S. Pat. No. 8,907,054, and claims the benefit of priority to U.S. Provisional Patent Application No. 61/521,215, filed on Aug. 8, 2011, the contents of which are incorporated herein by reference in their entireties.

STATEMENT REGARDING FEDERALLY SPONSORED RESEARCH OR DEVELOPMENT

This invention was made with government support under GM 068101 and GM 090162 awarded by the National Institutes of Health. The government has certain rights in the invention.

BACKGROUND

The Dpy-30 domain resembles, in sequence as well as structure, the dimerization and docking (D/D) domain, RIIa, in cAMP-dependent protein kinase (PKA). The history of RIIa and the emerging evidence on proteins containing the Dpy-30 domain can attest the importance of the discoveries related to the Dpy-30 domain pertain to this application.

RIIa targets PKA to A-Kinase-Anchoring-Proteins (AKAPs) in various micro-compartments in cells. The precise localization of PKA is central for this critical yet promiscuous enzyme that regulates various cellular reactions. Mutations interfering with the localization and function of PKA have severe impact on health and longevity. Various PKA-based reagents including those perturbing the binding between RIIa and AKAPs have been successfully developed into research tools and have potentials to be converted into therapeutic products. RIIa binds to a ~14-18-a.a. amphipathic helix (AH) in AKAPs. Some AHs has higher affinity than the others. Those AHs with a higher affinity block those with lower affinity. The first-generation AHs were further modified to generate additional AHs of varying affinity and specificity to different isoforms of PKA. In practice, the peptides, modified to improve solubility and membrane permeability, were used in at least two ways. For research, the high-affinity peptides perturb the binding in a RIIa overlay assay and the perturbation is necessary to confirm novel AKAPs. They were shown to perturb cellular reactions. In addition, they have been used in the discovery of non-peptidic chemical blockers.

In the same vein, the binding peptides to the Dpy-30 domain will become powerful tools. Dpy-30, as RIIa, is present in a handful of important molecules, most of which have not been vigorously studied. Yet it has been demonstrated that Dpy-30 protein, from which the domain derives its name, plays critical roles in development and in health. It is present in a wide range of organisms from single cell organisms to human. It is a key subunit in a major group of chromosome modification complexes—Set-1 like histone methyltransferase complexes. In nematodes, the body of the Dpy-30 mutant appears dumpy. In mammals, the chromosome modification complexes are the key culprits in acute mixed lineage lymphoma (MLL). The enzyme, Dpy-30 specifically, is crucial for the embryonic stem cells to differentiate into neurons. As shown from the history of PKA and RIIa, the discovery of high-affinity ligand for Dpy-30 will stimulate research in many directions, both basic and clinical.

In 2009 and 2010, it was demonstrated that human Dpy-30 protein binds to Ash2L of Set1-like histone methyltransferase complex and BIG1 of Golgi apparatus. And the binding fragments were identified. Thus like RI or RII of PKA, Dpy-30 as well as the Dpy-30 domain, likely have many binding proteins in the cells. However, the regions are longer than the binding cavity of the Dpy-30 domain. Furthermore, it has not been demonstrated that the interaction is through the Dpy-30 domain and the common features of the binding peptides remain unknown. Yang lab recently discovered the binding peptides respectively for RIIa domains and Dpy-30 domains in a highly conserved protein, RSP3 in the flagella of *Chlamydomonas*—a green alga and in humans. In particular, the binding site was narrowed down to 18-25 a.a. This small peptide in algal and human RSP3 share common features with each other and with the AHs for RIIa domains. Both peptides are amphipathic helices and thus are named $AH_R$ after the AH that bind RIIa in cells and $AH_D$ after the AH that bind Dpy-30 in cells. In addition, based on the study of flagellar protein, we discovered the shortest region in human Ash2L that bind Dpy-30 domain in the histone methyltransferase complex. However, there are distinctions between $AH_D$ and $AH_R$.

This study defines peptides that will bind the Dpy-30 domain specifically. Importantly, the $AH_R$ binds RIIa domains as well as Dpy-30 domains in vitro. The cross reactivity of $AH_R$ suggests that the applications using AHs that have been discovered so far potentially will cause serious problems. In contrast, $AH_D$S from flagellar RSP3 and from Ash2L are monospecific and highly selective to the Dpy-30 domain, indicating a high specificity. Furthermore, the interaction appears to be of high affinity because of the constitutive interactions of the Dpy-30 domains with RSP3 in flagella. Furthermore, the interaction can resist up to 0.6 M KI a chaotropic salt. These results strongly indicate that the Dpy-30-domain-binding peptides from RSP3 and from Ash2L could be modified into high-affinity and high-specificity derivatives that can be used to perturb the interaction of the Dpy-30 domain in methyltransferase complexes and in various circumstances in or outside the cells. The blocking peptides could be used for a wide range of applications, as shown in the blocking peptides for AKAP.

SUMMARY

Disclosed are peptide-based compounds including peptides or peptidomimetics that bind specifically to Dpy-30, and in particular peptides or peptidomimetics that bind specifically to the Dpy-30 binding domain or that bind specifically to a protein comprising the Dpy-30 binding domain. In particular, the peptides or peptidomimetics may bind to Dpy-30 specifically and inhibit Dpy-30 binding activity. The peptides and peptidomimetics typically are relatively short, comprising no more than about 50, 40, 30, or preferably 20 amino acids. The peptides and peptidomimetics typically have a relatively low molecular weight that is less than about 10 kD, preferably less than about 7.5 kD, more preferably less than about 5 kD, most preferably less than about 2 kD. Typically, the peptides and peptidomimetics are based on radial spoke protein 3 (RSP3) from the flagella of *Chlamydomonas reinhardtii*, the human radial spoke protein 3 (RSP3), or the human absent, small, homeotic discs 2-like (Ash2L) protein. The peptides and peptidomimetics may have one or more functional or biological activities associated with RSP3 or Ash2L. The peptides and peptidomimetics may be formulated as pharmaceutical compositions for treating and preventing conditions and diseases associated with Dpy-30 functional activity.

The peptides and peptidomimetics may bind to Dpy-30 or to a Dpy-30 binding domain with a relative high affinity and selectivity. In some embodiments, the pharmaceutical composition comprises a peptide or a peptidomimetic that binds Dpy-30 or a Dpy-30 binding domain with a $K_d$ of less than about 1 micromolar (more preferably with a $K_d$ of less than about 500 nanomolar, 100 nanomolar, 20 nanomolar, or most preferably with a $K_d$ of less than about 10 nanomolar). In further embodiments, the peptide or peptidomimetic binds Dpy-30 or a Dpy-30 binding domain and may have a $K_d$ within a range of about 1-20 nanomolar. In even further embodiments, the peptide or peptidomimetic does not bind to an RIIa domain or to a protein comprising an RIIa domain. The peptide or peptidomimetic may comprise or consist essentially of one or more contiguous amino acid sequences of RSP3 and Ash2L (e.g., a contiguous amino acid sequence of RSP3 or Ash2L having at least (or no more than) 10, 20, 30, 40, 50, 60, 70, 80, 90, or 100 amino acids). The peptide or peptidomimetic may comprise or consist essentially of a fragment of RSP3 or Ash2L that includes an N-terminal truncation, a C-terminal truncation, or both relative to full-length RSP3 or Ash2L.

The peptides and peptidomimetics may be formulated as a pharmaceutical composition for treating or preventing conditions associated with Dpy-30 activity. The compositions may include a carrier, diluent, or excipient. The pharmaceutical composition may comprise peptide or a peptidomimetic that is present at a concentration effective for inhibiting Dpy-30 binding to a target protein within a cell.

In some embodiments, the disclosed peptide or peptidomimetic comprises or consists essentially of any of SEQ ID NO:2 (ARGVVARRVV DKLVEDAAA), SEQ ID NO:4 (EYSMVGRTVL DMLIREVVK), and SEQ ID NO:6 (VVEHTLADVL YHVETEVDGR). In other embodiments, the disclosed peptide or peptidomimetic comprises or consists essentially of a variant of any of SEQ ID NOs: 2, 4, and 6, where the variant has at least about 80%, 90%, 95%, 96%, 97%, 98%, or 99% sequence identity to any of SEQ ID NOs: 2, 4, and 6 and the variant has Dpy-30 binding activity.

In some embodiments, the disclosed peptides or peptidomimetics may be utilized to discover proteins that comprise a Dpy-30 domain and their natural binding partners, such as Dpy-30 protein. The disclosed peptides or peptidomimetics may be utilized to block binding interactions that are facilitated by the Dpy-30 domain.

In further embodiments, the disclosed peptides or peptidomimetics may be utilized to modulate the function of Dpy-30 protein in cells within the context of culture systems or organisms. For example, the disclosed peptides or peptidomimetics may be utilized as tools to study and treat cell proliferation disorders or diseases such as cancer (e.g., mixed lineage leukemia (MLL)). In other embodiments, the disclosed peptides or peptidemimetics may be utilized as tools to manipulate differentiation of embryonic stem cells. In other embodiments, the disclosed peptides or peptidemimetics may be utilized as tools to treat diseases and disorders via modulating transcription and translation.

The disclosed peptides or peptidomimetics also may be utilized to develop non-peptide inhibitors of Dpy-30 binding activity. For example, the affinity and specificity of the disclosed peptides or peptidomimetics may be utilized to develop non-peptide inhibitors of Dpy-30 binding activity based on structural similarity.

Figure 13:
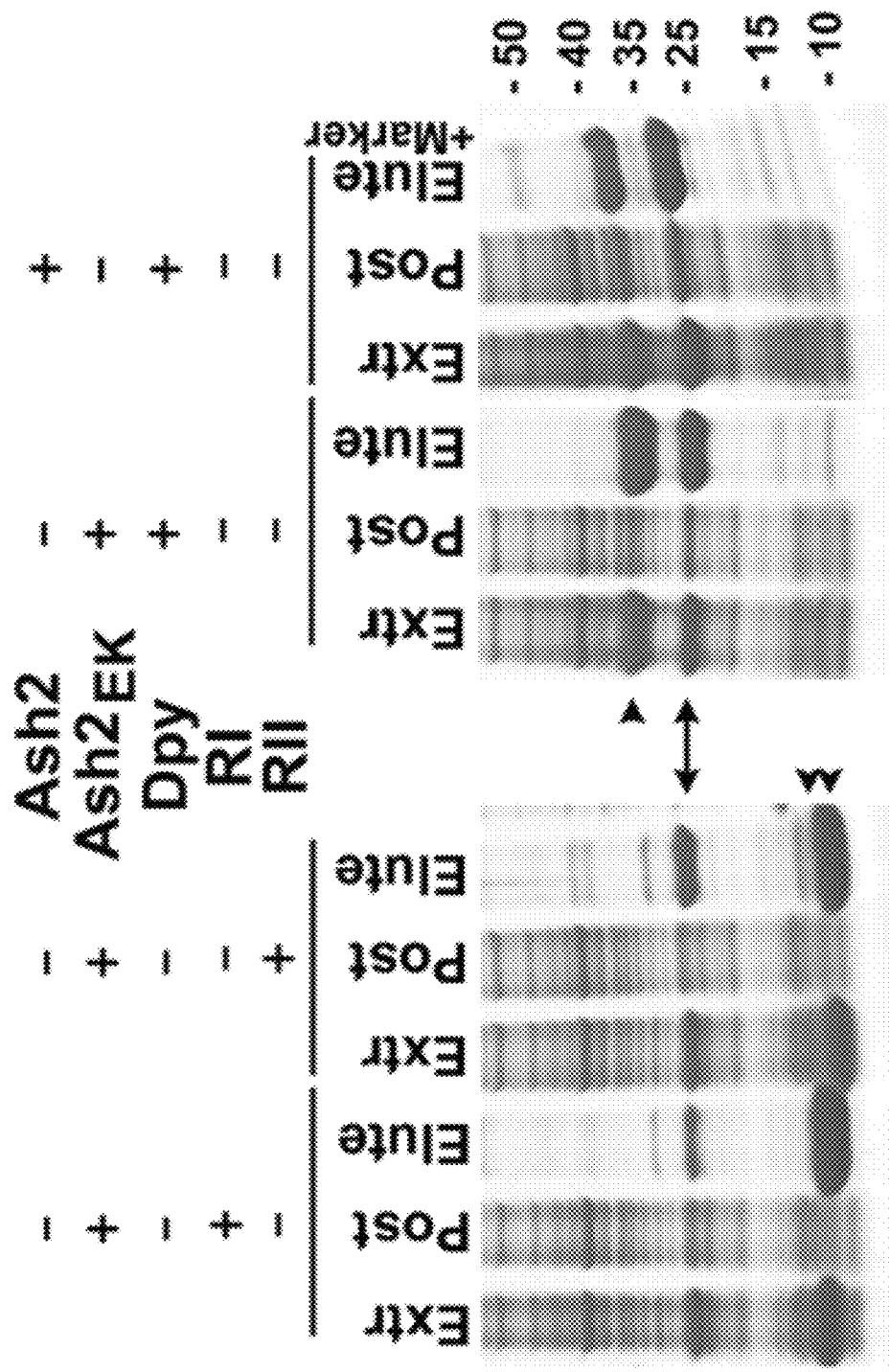

FIG. 13. $E_{604}K$ mutation increased the promiscuity of GST-hAsh2$_{593-623}$. Ni-NTA pulldown showed different effects of the $E_{510}K$ mutation to the co-purification of His-D/D domains (arrowhead). The mutation substantially increased the co-purification of GST-hAsh2$_{593-623}$ (arrow) with His-RIIα D/D, but its effect on RIα D/D or Dpy-30 D/D was not as evident. The samples were fractionated by SDS-PAGE and revealed by Coomassie stain. In this experiment, all fusion proteins were expressed at high concentrations and concentrated Dpy-30 D/D molecules form into stable oligomers (Dong et al., 2005) that resist dissociation by the SDS-PAGE sample buffer.

FIG. 14. The unusual residues potentially crucial for selective Ash2/Dpy-30 interaction. (A) Significant deviation of the ΦΦXX repeats in Ash2 AH. Manual alignment of the Dpy-30 D/D binding site in hAsh2 and RSP3 with the other putative sites showed frequent replacement of hydrophobic residue in the ΦΦXX motifs, especially the replacement with the charged $E_{615}$ (arrowhead) in the last motif. $E_{604}$ in the first motif (arrowhead) is highly conserved as well. The sequence in BIG1 has not been tested (?). (B) Sequence comparison of the D/D domains. The signature residues for each D/D are highlighted in grey shade. Note that a positively charged R in the domain from all Dpy-30 proteins is absent in that from DYDC-like proteins in the radial spokes. H.s., *Homo sapiens*; D.r., *Danio rerio*; S.m., *Schistosoma mansoni*; C.e., *Caenorhabditis elegans*; D.m., *Drosophila melanogaster*; S.c., *Saccharomyces cerevisiea*; C.r. *Chlamydomonas reinhardtii*.

DETAILED DESCRIPTION

The subject matter disclosed herein is described using several definitions, as set forth below and throughout the application.

Unless otherwise noted, the terms used herein are to be understood according to conventional usage by those of ordinary skill in the relevant art. In addition to the definitions of terms provided below, it is to be understood that as used in the specification, embodiments, and in the claims, "a", "an", and "the" can mean one or more, depending upon the context in which it is used.

As used herein, "about," "approximately," "substantially," and "significantly" will be understood by persons of ordinary skill in the art and will vary to some extent on the context in which they are used. If there are uses of the term which are not clear to persons of ordinary skill in the art given the context in which it is used, "about" or "approximately" will mean up to plus or minus 10% of the particular term and "substantially" and "significantly" will mean more than plus or minus 10% of the particular term.

Disclosed herein are peptides that bind to Dpy-30. In particular, the peptides may bind to the Dpy-30 binding domain or to proteins comprising the Dpy-30 binding domain. In some embodiments, the peptides do not bind to the RIIa binding domain or to proteins comprising the RIIa binding domain.

As used herein, a "peptide" is defined as a short polymer of amino acids, of a length typically of 50, 40, 30, 20 or less amino acids (Garrett & Grisham, Biochemistry, $2^{nd}$ edition, 1999, Brooks/Cole, 110). A "polypeptide" or "protein" is defined as a longer polymer of amino acids, of a length typically of greater than 50, 60, 70, 80, 90, or 100 amino acids.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

Also contemplated herein are peptidomimetics of the disclosed peptides. As disclosed herein, a peptidomimetic is a peptide equivalent characterized as retaining the polarity, three dimensional size and functionality (bioactivity) of its peptide equivalent but where the peptide bonds have been replaced (e.g., by more stable linkages which are more resistant to enzymatic degradation by hydrolytic enzymes). Generally, the bond which replaces the amide bond conserves many of the properties of the amide bond (e.g., conformation, steric bulk, electrostatic character, and possibility for hydrogen bonding). A general discussion of prior art techniques for the design and synthesis of peptidomimetics is provided in "Drug Design and Development", Chapter 14, Krogsgaard, Larsen, Liljefors and Madsen (Eds) 1996, Horwood Acad. Pub, the contents of which are incorporated herein by reference in their entirety. Suitable amide bond substitutes include the following groups: N-alkylation (Schmidt, R. et. al., Int. J. Peptide Protein Res., 1995, 46, 47), retro-inverse amide (Chorev, M and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391), which all are incorporated herein by reference in their entireties. The polypeptides disclosed herein may include peptidomimetic equivalents of the disclosed RSP3 variants, mutants, and fragments. The polypeptides disclosed herein may include peptidomimetic equivalents of the disclosed Ash2L variants, mutants, and fragments.

Variants and mutants of the disclosed peptides also are contemplated herein. As used herein, a "variant" or "mutant"

refers to a peptide molecule having an amino acid sequence that differs from a reference peptide or polypeptide molecule. A variant or mutant may have one or more insertions, deletions, or substitutions of an amino acid residue relative to a reference molecule. A variant or mutant may include a fragment of a reference molecule. For example, a RSP3 variant molecule has one or more insertions, deletions, or substitution of at least one amino acid residue relative to the RSP3 full-length polypeptide. The sequence of the full-length *Chlamydomonas reinhardtii* RSP3 polypeptide is presented as SEQ ID NO:1. The sequence of the full-length *Homo sapiens* RSP3 polypeptide is presented as SEQ ID NO:3. An Ash2L variant molecule has one or more insertions, deletions, or substitution of at least one amino acid residue relative to the Ash2L full-length polypeptide. The sequence of the full-length *Homo sapiens* RSP3 polypeptide is presented as SEQ ID NO:5.

A "deletion" refers to a change in the amino acid or that results in the absence of one or more amino acid residues. A deletion removes at least 1, 2, 3, 4, 5, 10, 20, 50, 100, 200, or more amino acids residues. A deletion may include an internal deletion or a terminal deletion (e.g., an N-terminal truncation, a C-terminal truncation or both of a reference polypeptide).

A "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full length polypeptide. A fragment of RSP3 may comprise or consist essentially of a contiguous amino acid sequence of RSP3 or Ash2L. A fragment may include an N-terminal truncation, a C-terminal truncation, or both relative to full-length RSP3 or full-length Ash2L (i.e., relative to SEQ ID NOs: 1, 3, or 5). In some embodiments, a fragment of RSP3 may comprise or consist essentially of amino acid sequence 281-318 of *Chlamydomonas reinhardtii* RSP3 (SEQ ID NO:1). In some embodiments, a fragment of RSP3 may comprise or consist essentially of amino acid sequence 296-333 of human RSP3 (SEQ ID NO:3). In some embodiments, a fragment of Ash2L may comprise or consist essentially of amino acid sequence 593-628 of Ash2L (SEQ ID NO:5).

The words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases. As described herein, variants, mutants, or fragments (e.g., a RSP3 variant, an Ash2L, variant, mutant, or fragment thereof) may have 99%, 98%, 97%, 96%, 95%, 94%, 93%, 92%, 91%, 90%, 80%, 70%, 60%, or 50% amino acid sequence identity relative to a reference molecule (e.g., relative to the RSP3 full-length polypeptide (SEQ ID:1, *Chlamydomonas reinhardtii* RSP3; or SEQ ID NO:3, *Homo sapiens* RSP3) or the Ash2L full-length polypeptide (SEQ ID NO:5, *Homo sapiens* Ash2L).

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

The amino acid sequences contemplated herein may include conservative amino acid substitutions relative to a reference amino acid sequence. For example, a variant, mutant, or derivative peptide may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed peptides, peptidomimetics, variants, mutants, or fragments described herein may have one or functional or biological activities exhibited by a reference polypeptide (e.g., one or more functional or biological activities exhibited by RSP3 or Ash2L). The disclosed peptides, peptidomimetics, variants, mutants, or fragments may bind to Dpy30 to form a complex. For example, The disclosed peptides, peptidomimetics, variants, mutants, or fragments may bind to Dpy-30 with a relative high affinity (e.g., a $K_d$ of less than about 1 micromolar (more preferably with a $K_d$ of less than about 500 nanomolar, 100 nanomolar, 20 nanomolar, or most preferably with a $K_d$ of less than about 10 nanomolar)). In further embodiments, the disclosed peptides, peptidomimetics, variants, mutants, or fragments bind Dpy-30 and may have a $K_d$ within a range of about 1-20 nanomolar). In even further embodiments, the disclosed peptides, peptidomimetics, variants, mutants, or fragments do not bind an RIIa domain or a protein comprising an RIIa domain.

The disclosed peptides or peptidomimetic may be substantially isolated or purified. The term "substantially isolated or purified" refers to amino acid sequences that are removed from their natural environment, and are at least 60% free, preferably at least 75% free, and more preferably at least 90% free, even more preferably at least 95% free from other components with which they are naturally associated.

The disclosed pharmaceutical compositions may include a therapeutic effective amount of a substantially isolated or purified peptide or peptidomimetic as disclosed herein. As used herein, the phrase "therapeutically effective amount" shall mean that dosage of an active agent that provides the specific pharmacological response for which the active agent is administered in a significant number of patients in need of such treatment. A therapeutically effective amount of an active agent that is administered to a particular patient in a particular instance will not always be effective in treating the conditions/diseases described herein, even though such dosage is deemed to be a therapeutically effective amount by those of skill in the art.

The pharmaceutical compositions disclosed herein may include a carrier, excipient, or diluent (i.e., agents), which are nontoxic to the cell or mammal being exposed thereto at the dosages and concentrations employed. Often a physiologically acceptable agent is in an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The presently disclosed peptides may be modified or formulated as a pharmaceutical composition in order to facilitate intercellular uptake. For example, the present disclosed peptides may be modified to include a protein transduction domain (e.g., as a fusion protein). Protein transduction domains (PTDs) are a class of peptides capable of penetrating the plasma membrane of mammalian cells and of transporting compounds of many types and molecular weights across the membrane. When PTDs are chemically linked or fused to other proteins, the resulting fusion proteins still are able to enter cells. PTDs are generally 10-16 amino acids in length and may be grouped according to their composition, such as, for example, peptides rich in arginine and/or lysine. PTDs also often are referred to as "Trojan peptides," "membrane translocating sequences," or "cell permeable proteins" (CPPs). PTDs have been fused to A-kinase-anchoring proteins (AKAPs) to create fusion proteins which have been shown to translocate across the cell membrane and disrupt protein kinase A (PKA) localization. (See Patel et al., J. Biol. Chem. Vol. 285, No. 36, pp 27632-27640, the content of which is incorporated herein by reference in its entirety). Accordingly, DPY-30 binding peptides fused to PTDs (either at the N-terminus, the C-terminus, or both) are contemplated herein.

Viral proteins that include protein transduction domains include HIV-1 Transactivator of Transcription (TAT) and HSV-1 VP 22 protein. The minimal PTD of TAT is the 9 amino acid protein sequence RKKRRQRRR ($TAT_{49-57}$) (SEQ ID NO:7). VP22 is the HSV-1 tegument protein, a structural part of the HSV virion. VP22 is capable of receptor independent translocation and accumulates in the nucleus. Fusion proteins comprising full length VP22 have been translocated efficiently across the plasma membrane.

Homeoproteins also have intercellular translocation properties. Homeoproteins are highly conserved, transactivating transcription factors involved in morphological processes. Several homeoproteins have been described to exhibit PTD-like activity and are capable of efficient translocation across cell membranes in an energy-independent and endocytosis-independent manner without cell type specificity. The Antennapedia protein (Antp) is a trans-activating factor capable of translocation across cell membranes, and the minimal sequence capable of translocation is a 16 amino acid peptide corresponding to the third helix of the protein's homeodomain (HD). Peptides up to 100 amino acids produced as fusion proteins with AntpHD penetrate cell membranes. Other homeodomains capable of translocation include Fushi tarazu (Ftz) and Engrailed (En) homeodomain. Many homeodomains share a highly conserved third helix.

Synthetic PTDs also have been synthesized. Many of these synthetic peptides are based on existing and well documented peptides, while others are selected for their basic residues and/or positive charge, which generally are believed to be crucial for PTD function. Synthetic peptides include, but are not limited to, PTD-4 (YARAAARQARA) (SEQ ID NO:8); PTD-5 (RRQRRTSKLMKR) (SEQ ID NO:9); MST-1 (AAVLLPVLLAAR) (SEQ ID NO:10); L-R9 (RRRRRRRRR) (SEQ ID NO:11); and Peptide 2 (SGWFRRWKK) (SEQ ID NO:12).

Human PTDs also have been identified. Human PTDs may circumvent potential immunogenicity issues upon introduction into a human patient. Peptides with PTD sequences include: Hoxa-5, Hox-A4, Hox-B5, Hox-B6, Hox-B7, HOX-D3, GAX, MOX-2, and FtzPTD. These proteins all share the sequence found in AntpPTD (RQIKI-WFQNRRMKWKK) (SEQ ID NO:13). Other PTDs include Islet-1, interleukin-1β, tumor necrosis factor, and the hydrophobic sequence from Kaposi-fibroblast growth factor or FGF-4) signal peptide, which is capable of energy-, receptor-, and endocytosis-independent translocation. Unconfirmed PTDs include members of the Fibroblast Growth Factor (FGF) family.

Additional PTD and CPPs are known in the art. (See, e.g., Foerg, C.; Merkle, H. P. On the biomedical promise of cell penetrating peptides: Limits versus prospects. *J. Pharm. Sci.* 2008, 97, 144-162; Juliano, R.; Alam, M. R.; Dixit, V.; Kang, H. Mechanisms and strategies for effective delivery of antisense and siRNA oligonucleotides. *Nucleic Acids Res.* 2008, 36, 4158-4171; Kersemans, V.; Kersemans, K.; Cornelissen, B. Cell penetrating peptides for in vivo molecular imaging applications. *Curr. Pharm. Des.* 2008, 14, 2415-2447; Torchilin, V. P. Cell penetrating peptide-modified pharmaceutical nanocarriers for intracellular drug and gene delivery. *Biopolymers* 2008, 90, 604-610; Vives, E.; Schmidt, J.; Pelegrin, A. Cell-penetrating and cell-targeting peptides in drug delivery. *Biochim. Biophys. Acta* 2008, 1786, 126-138; El-Sayed, A.; Futaki, S.; Harashima, H. Delivery of macromolecules using arginine-rich cell penetrating peptides: Ways to overcome endosomal entrapment. *AAPS J.* 2009, 11, 13-22. *Pharmaceuticals* 2010, 3 612; Fonseca, S. B.; Pereira, M. P.; Kelley, S. O. Recent advances in the use of cell-penetrating peptides for medical and biological applications. *Adv. Drug Deliv. Rev.* 2009, 61, 953-64; Heitz, F.; Morris, M. C.; Divita, G. Twenty years of cell-penetrating peptides: From molecular mechanisms to therapeutics. *Br. J. Pharmacol.* 2009, 157, 195-206; and Pujals, S.; Giralt, E. Proline-rich, amphipathic cell-penetrating peptides; the contents of which are incorporated herein by reference in their entireties).

The presently disclosed peptides also may be formulated as a pharmaceutical composition in order to facilitate intercellular uptake. In some embodiments, the disclosed peptides may be prepared as a liposomal or micelle formulation or may be complexed to a carrier (e.g., polyethylene glycol (PEG)) in order to facilitate intercellular uptake. (See, e.g., U.S. Pat. Nos. 6,147,204 and 6,011,020; the contents of which are incorporated herein by reference in their entireties). The presently disclosed peptides may be administered in the form of liposome or micelle delivery systems, such as small unilamellar vesicles, large unilamellar vesicles and multilamellar vesicles. Liposomes and micelles can be formed from a variety of phospholipids, such as cholesterol, stearylamine or phosphatidylcholines. In some embodiments, the disclosed peptides are formulated as a complex comprising a liposome or micelle with the disclosed peptides associated with the surface of the liposome or micelles or encapsulated within the liposome or micelle. Preformed liposomes or micelles can be modified to associate with the disclosed peptides. For example, a cationic liposome or micelles may associate through electrostatic interactions with the disclosed peptides. Alternatively, the disclosed peptides may be conjugated to a lipophilic compound, such as cholesterol, which are then added to preformed liposomes or micelles whereby the cholesterol becomes associated with the liposomal or micelle membrane. Alternatively, the disclosed peptides can be associated with the liposome or micelle during the formulation of the liposome or micelle. Suitable liposomes or micelles may be modified to include a water-soluble polymer, such as polyethylene glycol (PEG), which reduces the rate by which the liposome or micelle is removed from circulation and also increases the water solubility of the liposome or micelle, prolonging circulatory half-life and bioactivity.

The disclosed pharmaceutical compositions may be administered to a patient or subject in need thereof. As used herein, a "patient" may be interchangeable with "subject" and means an animal, which may be a human or non-human animal, in need of treatment. Non-human animals may include dogs, cats, horses, cows, pigs, sheep, and the like.

A "patient in need thereof" may include a patient having, suspected of having, or at risk for acquiring a disease or disorder effected by DPY-30 or by a protein having a DPY-30 binding domain. For example, a patient in need thereof may include a patient having, suspected of having, or at risk for acquiring hyperplasia or cancer (e.g., leukemia, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, liver cancer (e.g., hepatocellular carcinoma), kidney cancer (e.g., renal cell carcinoma), cervical cancer, Kaposi's sarcoma and ovarian cancer.

The methods disclosed herein may include methods of modulating cell proliferation either in vitro or in vivo (e.g., in a patient in need thereof). As used herein, "modulating" means "changing" or "regulating" and may include "inhibiting" cell proliferation. The methods may include modulating cell proliferation in a cell (e.g. inhibiting cell proliferation in a cell) exhibiting hyperplasia or in a cancerous cell. For example, the methods may include treating a cell with a peptide or a peptidomimetic as disclosed herein. The peptides and peptidomimetics disclosed herein may be administered to patients in need thereof in treatment methods or prevention methods. For example, the compounds may be administered as a pharmaceutical composition for modulating cell proliferation in a patient in need thereof.

EXAMPLES

The following Examples are illustrative only and do not limit the scope of the claimed subject matter.

Example I. A Flagellar AKAP with Two Amphipathic Helices Form a Structural Scaffold in the Radial Spoke Complex Abstract A-kinase anchoring proteins (AKAPs) contain an amphipathic helix (AH) that binds the dimerization and docking (D/D) domain, RIIa, in cAMP-dependent protein kinase (PKA). Many AKAPs were discovered solely based on the AH-RIIa interaction in vitro. An RIIa or a similar Dpy-30 domain is also present in numerous diverged molecules that are implicated in critical processes as diverse as flagellar beating, membrane trafficking, histone methylation and stem cell differentiation, yet these molecules remain poorly characterized. Here we demonstrate that an AKAP, RSP3, forms a dimeric structural scaffold in the flagellar radial spoke complex, anchoring through two distinct AHs the RIIa and Dpy-30 domains in four non-PKA spoke proteins involved in the assembly and modulation of the complex. Interestingly, one AH can bind both RIIa and Dpy-30 domains in vitro. Thus, AHs and D/D domains constitute a versatile yet potentially promiscuous system for localizing various effector mechanisms. These results greatly expand the current concept about anchoring mechanisms and AKAPs.

Introduction

Many molecules involved in signal transduction are localized to specific sub-cellular compartments. The best example is cAMP-dependent protein kinase (PKA), a key effector for the cAMP signaling pathway. PKA holoenzyme is a tetramer comprised of two catalytic subunits and two regulatory subunits. It is anchored to specific sub-cellular locations by a diverse array of A-Kinase Anchoring Proteins (AKAPs) (reviewed by Welch et al., 2010). Aside from PKA, most AKAPs also anchor additional molecules involved in other signal transduction pathways (Klauck et al., 1996; Scott and Pawson, 2009). The multitude of molecular switches anchored by AKAPs inspires a widely accepted theory that AKAPs serve as signal transduction scaffolds localizing PKA, a critical enzyme of broad substrate specificity, near intended substrates and other signaling pathways. As such, AKAPs integrate synergistic or antagonistic pathways and enhance the spatial and temporal precision of phosphoregulation. Extensive evidence has shown that AKAP-mediated anchoring is critical for PKA-regulated cellular reactions, organ functions and longevity (Greengard et al., 1991; Kammerer et al., 2003; reviewed by Mauban et al., 2009).

The anchoring of PKA is mediated by the interaction between a 14-18 amino acid (a.a.) amphipathic helix (AH) in AKAPs and the dimer of RIIa, a 40-a.a. dimerization and docking domain (D/D) in the regulatory subunit, RI or RII, of PKA. This AH-RIIa interaction has been commonly utilized to discover AKAPs (Carr et al., 1991). Many molecules are designated as AKAPs if they bind RI in a blot overlay and if the binding can be specifically blocked by a high affinity RIIa-binding AH ($AH_R$), like Ht-31 from AKAP-Lbc (Carr et al., 1992). However, accumulated evidence indicates that the applications of the AH-RIIa interaction are broader than simply anchoring PKA. Firstly, the RIIa domain is present not only in PKA regulatory subunits but also in more than 200 eukaryotic proteins with distinct molecular architectures. Some of them are enriched in cilia and flagella and bind AKAPs in vitro just as RII does (Fujita et al., 2000; Carr et al., 2001; Yang et al., 2006; Newell et al., 2008). This suggests that the RIIa domains from various proteins are functionally equivalent and the RII overlay assay can potentially reveal "AKAPs" that actually anchor non-PKA RIIa proteins. Secondly, the Dpy-30 domain that is present in over 200 proteins is similar in sequence and structure to RIIa (Wang et al., 2009; Roguev et al., 2001). Both Dpy-30 and RIIa are comprised of an X-shaped bundle of two helix-loop-helix monomers (FIG. 1), but differ at the N-terminus (Gold et al., 2006; Kinderman et al., 2006; Wang et al., 2009). Proteins with either a RIIa domain or a Dpy-30 domain are classified into two families within the RIIa clan in the Pfam database. (See Wellcome Trust Sanger Institute Pfam 26.0 database website).

Emerging evidence shows that the non-PKA members in the RIIa clan are important for a wide range of functions distinct from PKA. For example, Dpy-30 protein, the namesake of the domain, is a small core subunit in Set1-like histone methyltransferase complexes in eukaryotic cells (Cho et al., 2007). It is dispensable for the enzymatic activity (Patel et al., 2009) but modulates H3K4 tri-methylation (Jiang et al., 2011). A defective dpy-30 gene results in a dumpy body shape in *C. elegans* (Hsu et al., 1994), while depletion of Dpy-30 transcripts blocks trans-Golgi trafficking (Xu et al., 2009) and neuronal differentiation of embryonic stem cells (Jiang et al., 2011). Despite the importance, the non-PKA RIIa clan members and their interacting partners remain poorly defined.

Figure 1:
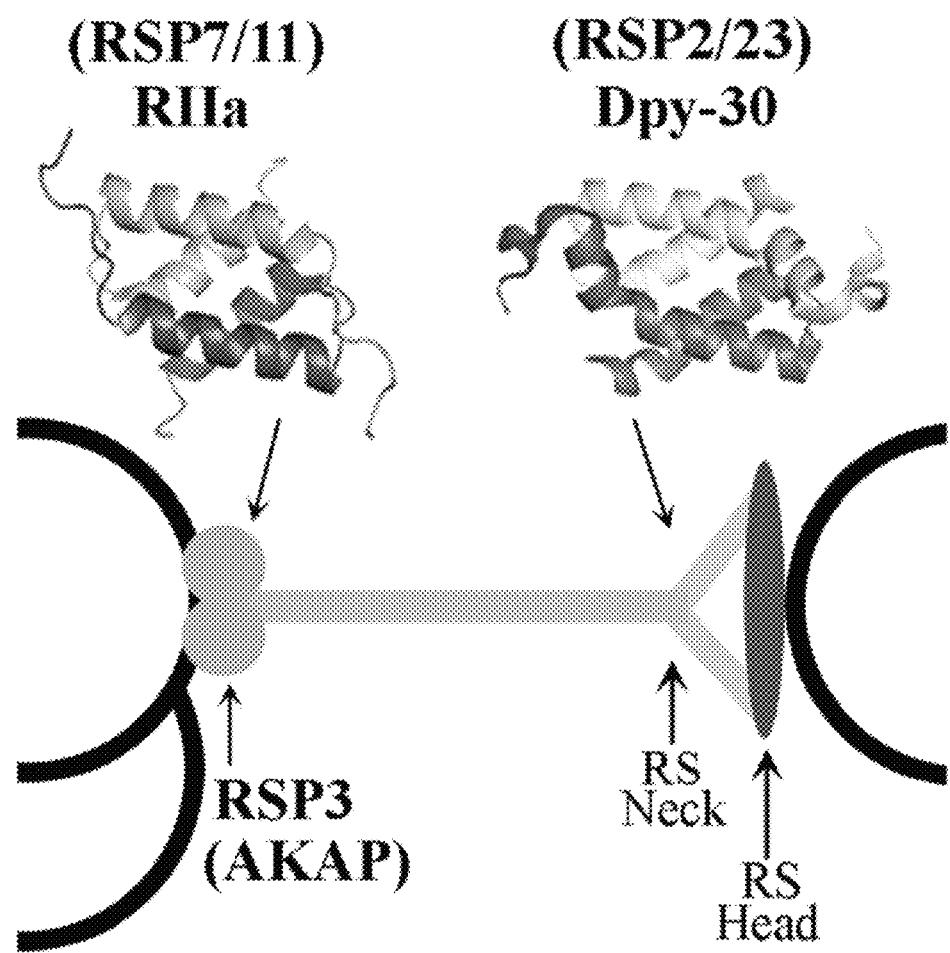
FIG. 1. Predicted locations of RSP3 AKAP and the D/D-domain-containing RSPs in the radial spoke complex. RS is positioned between the microtubule outer doublet (left) and the central pair (right). RSP3 dimer (circles) is thought to be the base of the radial spoke. The RIIa-domain-containing RSP7 and RSP11 are located toward the base while the Dpy-30-domain-containing RSP2 and RSP23 are near the neck region underneath the spokehead. The prediction is based on RS deficiencies in RS mutants. Only a fraction of the 9+2 axoneme is depicted. The crystal structures of the RIIa and Dpy-30 domains were generated using PyMol (pdb id 1L6E; Morikis et al., 2002 and 3G36; Wang et al., 2009).

To elucidate the molecular interactions of these putative D/D domains and the functions that they may tether, we investigated the radial spoke (RS) complex in *Chlamydomonas* flagella, that harbors an AKAP as revealed by the RII overlay (Gaillard et al., 2001) and four subunits with a RIIa domain or a Dpy-30 domain (Patel-King et al., 2004; Yang et al., 2006). The RS consists of a thin spoke stalk and an enlarged spoke head, nestled between outer doublet microtubules and the central pair (CP) apparatus in the 9+2 axoneme (FIG. 1). Diverse evidence suggests that the RS serves as a mechanical transducer, intermittently coupling the outer doublets and the CP to coordinate dynein motors that drive oscillatory beating (Warner and Satir, 1974; Omoto et al., 1999; Yang et al., 2008). Furthermore, the RS is involved in motility changes induced by $2^{nd}$ messengers and phosphorylation (Brokaw et al., 1982; Satir 1999; Howard et al., 1994; Habermacher and Sale, 1996; 1997). The spoke AKAP, RSP3, and the radial spoke proteins (RSPs) with a putative D/D domain appear to be involved in these central functions and are exclusively located in the spokestalk. RSP3 AKAP operates as a homodimer (Wirschell, et al., 2008). It is essential to the assembly of the entire complex and considered to be the spoke base, targeting RSs to axonemes (Williams et al., 1989; Diener et al., 1993). RSP7 and RSP11 have a RIIa domain, while RSP2 and RSP23 have a Dpy-30 domain. Aside from the putative D/D domains, they all carry distinct additional sequences implicated in assembly, calcium signaling, motility modulation or enzymatic activity (Patel-King et al., 2004; Yang et al., 2006; Yang and Yang, 2006). Most notably, RSP2 is critical for bridging the head-module and stalk-module together. The RSP deficiencies in RSP2 mutant pf24 (Huang et al., 1981; Patel-King et al., 2004) and chemical cross-linking (Kohno et al., 2011) strongly suggest that the two Dpy-30-domain-containing subunits are located underneath the spokehead, whereas the two RIIa-domain-containing subunits are located near RSP3 at the base of the RS (FIG. 1, Yang et al., 2006). Intriguingly, mutations within the $AH_R$ of RSP3 abolished the interaction of the $AH_R$ with RII in the in vitro overlay assay, yet the same mutation in *Chlamydomonas* resulted in partially paralyzed flagella that still had the RIIa-containing RSP7 and RSP11 (Gaillard et al., 2006).

These observations raise multiple questions. Does RSP3 in vivo bind PKA's RII as demonstrated in the overlay assay (Gaillard et al., 2001) or, instead, its neighboring RSPs with their RIIa domains? Which spoke protein interacts with the Dpy-30 domain? How are these four proteins with similar D/D domains localized to distinct positions within the same complex? How do these molecules contribute to the mechanism of the RS? The answers to these questions will help to elucidate cellular reactions that employ the RIIa clan members, including the RS-mediated motility control, and may broaden the impact from the discoveries of AKAPs beyond the realm of PKA. We postulate that the core of the spoke stalk is entirely comprised of a RSP3 dimer that then directly anchors the RIIa and Dpy-30 domains in the four RIIa clan RSPs to form a rigid backbone for mechanical coupling. To test this, we generated a panel of RSP3 truncation mutants in conjunction with in vitro experiments. The combined approaches revealed two similar but discrete AHs in RSP3 for anchoring the RIIa and Dpy-30 domain. These D/D domains in turn tether the effector modules that mediate the assembly and modulation of the RS. Interestingly, in vitro, the Dpy-30 domain exhibited cross reactivity for the RIIa-binding AH but the RIIa domain did not cross react with the Dpy-30-binding AH. These findings reveal that a single mechanism of unexpected versatility and promiscuity localizes distinct non-PKA effectors to specific micro-compartments, bestowing the morphology and mechanisms central to this motility-regulating complex. This principle is expected to be applicable to the other RIIa clan members and their anchoring proteins.

Results

Prediction of the RIIa Clan Anchoring Protein in the RS.

Based on electron micrographs of beating cilia, it was predicted that RSs are rigid in order to mechanically couple the mobile CP and outer doublets intermittently at a high frequency (Warner and Satir, 1974). We reason that a RS with all four RIIa clan members docking to the same core protein extending throughout the complex may have higher rigidity than a RS made from a chain of consecutive individual RIIa clan members. The core molecule should be filamentous and long enough to span the distance from the outer doublets to the CP. Furthermore, it should be evolutionarily conserved, as the dimension of typical 9+2 axonemes is similar (Mastronarde et al., 1992; Pigino et al., 2011; Barber et al., 2012). Sequence analysis showed that among the 19 spoke components, the best candidate core protein is RSP3, the dimeric spoke AKAP (Wirschell et al., 2008; Gaillard et al., 2001, Diener et al., 2011), although experimental evidence positioned RSP3, in fact only its N-terminal ~80-a.a. region, at the base of the RS, for binding the entire complex to the axoneme (Diener et al., 1993, FIG. 2).

The 516-a.a. RSP3 could be viewed as two structurally distinct segments divided by the RIIa-binding amphipathic helix ($AH_R$) at a.a.#161-178 (Gaillard et al., 2001) (FIG. 2A). The N-terminal 160-a.a. region, that binds axonemes (Diener et al., 1993; the grey bar) and a stack of 3-5 LC8 dimers, is equivalent to a 12-20-nm rod (see accompanying paper by Gupta A., Sivadas P., Diener D. R., Rosenbaum J. L. and Yang P.). The remainder of RSP3 is largely helical with a propensity to form three coiled coils (FIG. 2B), structures known for protein-protein interactions. Only the first ~320-a.a. region upstream to Coil 2 is highly conserved and is recognized as a RSP3 domain (the black bar) by the Pfam database. Coil 2, with a lower coiled coil propensity, is mildly conserved, whereas Coil 3 and the downstream sequence are unique to *Chlamydomonas* and are dispensable (Diener et al., 1993). The conserved 160-a.a. helix from $AH_R$ to Coil 2 will be ~24-nm long, if each turn of the α-helix contains 3.6 a.a. and is 0.54-nm long (Pauling et al., 1951). Together, the entire conserved 320-a.a. region, with 12-20-nm LC8-$RSP3_{1-160}$ complex and 24-nm $RSP3_{160-320}$ dimeric coiled coil, is sufficient to extend throughout the stalk of the 38-41-nm RS (Yang et al., 2001; Nicastro et al., 2005; Pigino et al., 2011). Thus, we postulate that the dimer of the conserved 320-a.a. region in RSP3 (FIG. 2C, black and grey wires) forms the core of the RS, with binding sites not only for the axoneme (Diener et al., 1993) and the RIIa domains (circles) (Gaillard et al., 2001) but also for Dpy-30 domains (circles) and possibly the spokehead (oval disk). The RIIa and Dpy-30 domains tether to four types of effector modules—armadillo repeats (ARM in RSP8, which is reduced in RSP11 mutant), calcium-binding motifs (Ca in RSP7), nucleoside diphosphate kinase (NDK in RSP23) domain and coiled coils.

RSP3 Truncation Mutagenesis Reveals the Binding Region for the RIIa Domain and its Tethered Moieties.

This model explains the observation that although mutations in RSP3's $AH_R$ abrogate the interaction of RSP3 with RII in an overlay assay (Gaillard et al, 2001), the same mutations did not perturb the assembly of the RIIa-domain containing proteins, RSP7 and RSP11 into the RS (Gaillard et al., 2006). RSP7 and RSP11 may engage in multiple interactions, directly or indirectly, with RSP3 (FIG. 2C) and hence a perturbation in the $AH_R$-RIIa interaction alone is insufficient to prevent their assembly. If the model is correct, deletion of all involved sequences in RSP3 will result in an axoneme devoid of these two RIIa-containing molecules and possibly their associated molecules, such as RSP8 with ARM repeats that are known to promote protein-protein interactions. On the other hand, retention of the $AH_R$ alone will be sufficient for the assembly of some, if not all, of these molecules.

Figure 2:
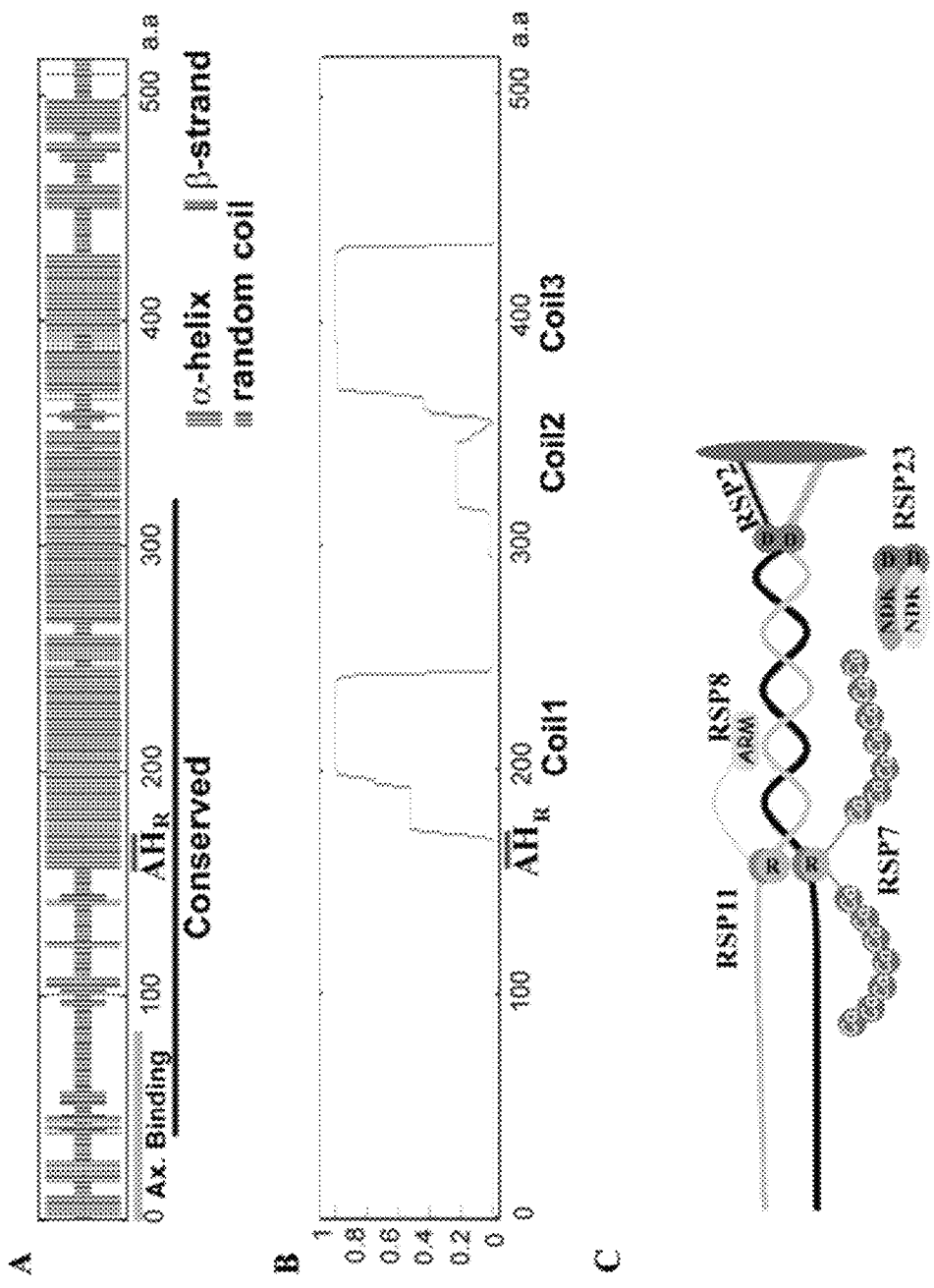
FIG. 2. Sequence analysis and the new model of RSP3-centered RS. (A) The secondary structure of RSP3 appears to be divided into two distinct areas by the RIIa-binding amphipathic helix ($AH_R$, underline). The N-terminal 160 a.a. contains random coils interspersed with short α-helices and β-strands, while the C-terminus is primarily composed of α-helices. The black bar corresponds to the RSP3 domain that is highly conserved among orthologues. The grey bar corresponds to the axoneme-binding region. (B) RSP3 contains three areas with different propensities to form coiled coils. The prediction was made by the COILS program using the window size of 28 a.a. (C) A model depicting RSP3 dimer (black and gray lines) as the core in the RS, with two sites for anchoring RIIa (R) and Dpy-30 (D), domains in two pairs of RSPs. Each domain tethers distinct molecular moieties as effector mechanisms, like RSP8, an armadillo repeat protein (ARM); calcium-binding EF-hands (Ca) in RSP7; coiled coils and nucleoside diphosphate kinase (NDK) in RSP2 and RSP23 respectively.

To test this, we first created two complementary deletion strains guided by the predicted molecular modules: the 1-178 strain that terminates at the end of the $AH_R$; and Δ1 strain that lacks Coil 1 (a.a.#171-244) and, as a consequence, is missing part of the $AH_R$ (FIG. 2). The third strain, Δ2, that lacks the small Coil 2 (#316-354), and wild type strain served as controls. All polypeptides retained the axonemal binding region at the first 80 a.a. so that they could be assembled into the axoneme. The C-terminus of all RSP3 polypeptides was tagged with 3 HA epitopes and 12 His residues for detection, semi-quantitative comparison and protection of the truncated free end.

All of the deletion constructs were modified from a plasmid carrying the wild type (WT) RSP3 genomic DNA. An antibiotic-resistant cassette was inserted into each plasmid to aid the selection of *Chlamydomonas* clones carrying the transgene. The intact and deletion constructs were transformed individually into the RSP3 mutant pf14 in which a premature stop codon results in diminished expression of the RSP3 polypeptide and the spoke-less axonemes (Williams, et al., 1989; Diener et al., 1993). More than 40 antibiotic-resistant clones for each construct were screened microscopically. All clones in both the Δ1 and 1-178 groups were paralyzed. On the other hand, among the 118 Δ2 clones screened, 50 clones contained motile cells (Table 1):

TABLE 1

| Construct | Observed | Motile[a] | Flagella prep.[b] | HA+ |
| --- | --- | --- | --- | --- |
| Δ1 | 160 | 0 | 23 | 5 |
| Δ2 | 118 | 50 | 16 | 7 |
| 1-178 | 40 | 0 | 10 | 2 |
| 1-244 | 50 | 0 | 10 | 3 |
| 1-269 | 92 | 0 | 10 | 2 |
| 1-316 | 114 | 47 | 10 | 7 |

[a]The numbers of colonies that contained swimmers. The percentage of swimmers from each clone varied. The swimmers cannot maintain linear trajectory and their flagella had a higher rate of asynchrony than WT cells.
[b]The flagella quantity from each crude preparation for HA western blots varied, affected by the population of flagellated cells and the deflagellation level.

Single colonies of antibiotic-resistant transformants were randomly picked and re-streaked on agar plates. A fraction of each colony was resuspended in water or media for light microscopy. The crude flagella preparation was made from a plate of clones randomly selected from the group of Δ1, 1-178, 1-244 and 1-269 that were 100% paralyzed; or from the clones with swimmers from the group of Δ2 and 1-316. The samples were then assessed by HA western blots. Recorded in each column of Table 1 was the colony number.

A fraction of cells in the suspension were swimming. But unlike WT cells, they could not maintain helical trajectories. Their flagella beat with largely normal waveform but lost synchrony frequently. The flagella of immotile cells were paralyzed or twitching. The mixture of swimmers and immotile cells from a single clone resembles the phenotype of several mutants with mild RS deficiencies (Huang et al., 1981; Yang and Yang, 2006; Gaillard et al., 2006; Wei et al., 2010). This indicates that Δ2-RSP3 polypeptides were restored to the axoneme of the swimmers and were capable of rescuing paralyzed flagella, albeit partially. For those Δ2 clones that have paralyzed or twitching flagella only, the Δ2-RSP3 plasmid may not have inserted into the genome properly to restore the polypeptides at a sufficient quantity.

Figure 3:
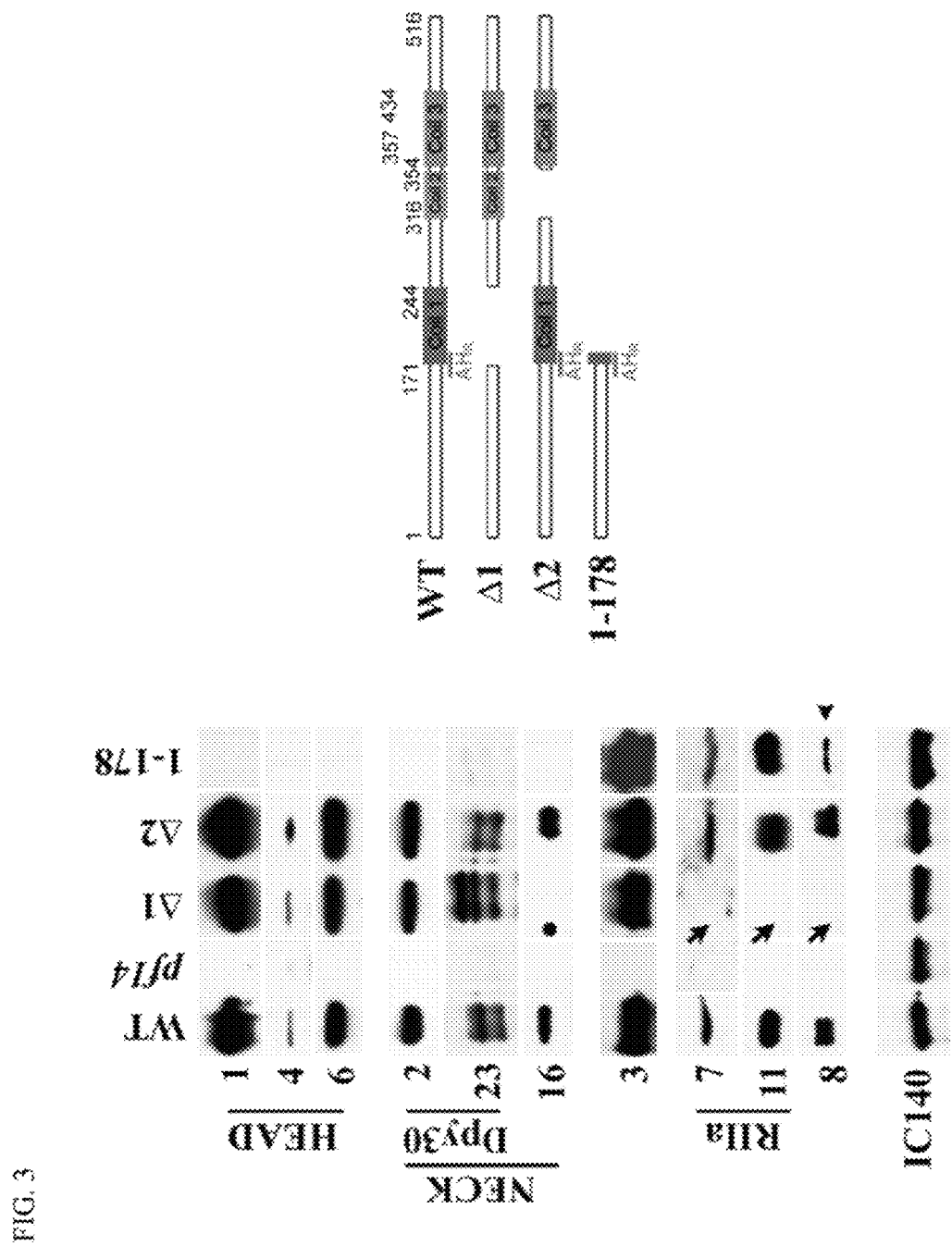
FIG. 3. Deletions around the Coil 1 region resulted in the deficiencies in RIIa-domain-dependent assembly. Representative western blots of axonemes (left panel) from WT and the RSP3 strains defective in the region around coiled coils (right panel) were probed for relevant RSPs as indicated. RIIa proteins (RSP7 and 11) and the ARM protein (RSP8) were missing in the Δ1 strain (arrows) in which half of the RIIa-binding $AH_R$ was truncated. RSP16, whose assembly required RSP2, was also absent (dot). These proteins appeared normal in Δ2 axoneme. The 1-178 axonemes that retained RSP3 sequence up to the $AH_R$ lacked all the proteins in the spokehead and spokeneck but contained RIIa proteins (RSP7 and RSP11). Note RSP8 was less abundant (arrowhead). The spoke-less pf14 was the negative control. IC140, an inner dynein arm subunit, indicated the protein load.

To identify those clones with tagged RSP3 present in the axoneme, HA western blots were conducted on crude flagella preparations made from at least 10 clones randomly selected from the paralyzed Δ1 and 1-178 groups; and from the motile clones in the Δ2 group. Axonemes, purified from the positive clones (Table 1), were then probed for HA and representative RSPs (FIG. 3). The amounts of RSP3 variants and wild type (WT) RSP3-HAHis appeared similar. The axonemes from the Δ1 strain that was missing Coil 1 (a.a.#171-244) and part of the $AH_R$ (a.a.#161-178) in RSP3 lacked both the RIIa-containing RSP7 and RSP11, as well as the ARM repeat protein RSP8 as expected (FIG. 3, arrows, compare blots on the left and prediction on the right), while the more distally-located proteins in the spoke head and neck region, including the Dpy-30-domain-containing RSPs, were present at normal levels. This result confirms that the RS is not comprised of a string of consecutive RSPs. RSP16, the spoke HSP40, was drastically reduced in the axoneme of the RSP2 mutant (Huang et al., 1981; Yang et al., 2005) and was absent in the Δ1 axoneme (dot) despite the presence of RSP2. The HSP40 deficiency in mutants either defective in RSP2 or RSP3's Coil 1 suggests that HSP40 interacts with both RSP2 and RSP3. For the 1-178 axonemes, in which RSP3 fragment was terminated immediately after the $AH_R$ (a.a.#161-178), both RSP7 and RSP11 were present, but the head proteins (RSP1, RSP4, RSP6) and neck proteins (RSP2, RSP23 and RSP16) were absent (FIG. 3). Therefore, the region up to $AH_R$ is sufficient to anchor the two non-PKA RIIa proteins. Note that 1-178 axonemes (arrowhead) contained less RSP8 than the WT control, like the axoneme of the RSP11 mutant pf25 (Yang et al., 2006). The RSP8 deficiency in strains defective either in RSP3 Coil 1 (1-178 or Δ1 strains) or in RSP11 supports the prediction that RSP11 and RSP8 form a tri-molecular sub-complex with RSP3 Coil 1 (FIG. 2C). Furthermore, the fact that Dpy-30 domain containing RSP2 and RSP23 are absent in the 1-178 strain but normal in the Δ1 and Δ2 strains suggests that the Dpy-30 domain binding site is located between Coil 1 and Coil 2. The band patterns of RSP23 varied among preparations and among different strains defective in RSs or dyneins (Yang et al., 2009; Patel-King et al., 2004). It is unclear if the variation is due to RSP23's unusual susceptibility to degradation or is partly due to RSP3 mutations.

RSP3's Helical Region Associates with Dpy-30-Domain-Containing Proteins.

To identify the region that bind RSP2 and RSP23, we took the same strategy to generate three more strains in which RSP3 polypeptides terminate at different residues between Coil 1 and Coil 2, i.e. a.a.#244, 269, and 316 respectively. As expected, all clones in the 1-244 and 1-269 groups were paralyzed (Table 1), whereas ~40% of the clones in the 1-316 group that lacks Coil 2 and the downstream sequence contained swimmers, just like the Δ2 group that lacks Coil 2 only. This further confirms that the less conserved Coil 2 region is beneficial, albeit dispensable, to flagellar beating. Preliminary western blots of flagella from selected clones identified RSP3 (HA)-positive clones. The axonemes from these clones were subjected to detailed western blot analysis.

Figure 4:
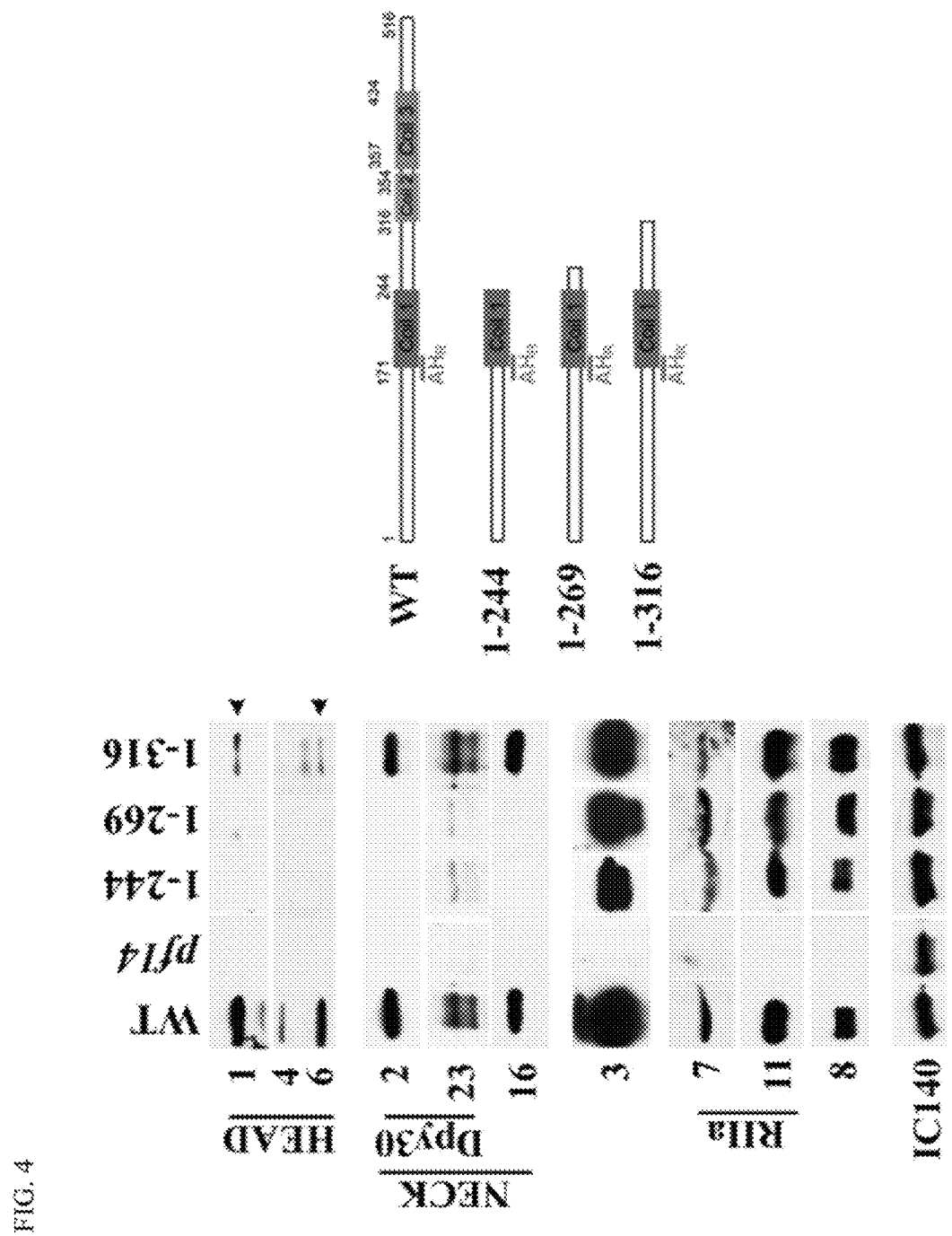
FIG. 4. Deletions between the first two coils resulted in the deficiencies in Dpy-30-domain-dependent assembly. Western blots of axonemes (left panel) extracted from WT and three mutants with different truncations distal to Coil 1 (right panel) were probed for relevant RSPs as indicated. 1-244 strain and 1-269 strain were deficient in the spokehead proteins and the spokeneck proteins including RSP16 and the two Dpy-30-domain-containing RSP2 and RSP23. These proteins were present in 1-316 strain but the spokehead proteins were less abundant (arrowheads) than that in the WT control.

The axonemes from the paralyzed 1-244 and 1-269 strains resembled 1-178 axonemes, lacking the neck proteins (RSP2, RSP23 and RSP16) and the head proteins (RSP1, RSP4 and RSP6) (FIG. 4). This suggests that the region involved in the head-neck assembly and in anchoring the Dpy-30 domain is within a.a.#269-316 in RSP3. For the 1-244 and 1-269 strains that retain both $AH_R$ and Coil 1, the axoneme had normal amounts of RIIa-domain-containing RSP7 and RSP11 as well as the ARM repeat protein RSP8, consistent with the prediction that the mutually interacting RSP11 and RSP8 bind to $AH_R$ and Coil 1. The 1-316 axonemes, in which RSP3 lacks both Coil 2 and Coil 3, were similar to Δ2 axonemes, in which all RSPs were present (compare FIG. 3 and FIG. 4) except that the head proteins (RSP1, RSP4 and RSP6) were drastically reduced (arrowheads). Consistent with this, fewer cells expressing 1-316 swam in stationary phase cultures (axonemes were harvested from stationary phase cultures) than in the suspension from fresh plates or the log phase culture. This media effect on the motility level and assembly was noted previously in two spoke mutants (Yang and Yang, 2006; Wei et al., 2010). The head protein deficiency in this strain missing RSP3's C-terminus resembles the phenotype of the RSP2 mutant pf24 (Huang et al., 1981; Patel-King et al., 2004; Yang et al., 2006), suggesting that both RSP2 and RSP3's C-terminus are involved in, albeit not required for, the assembly of the spokehead and thus head proteins are not entirely absent when only one of them is defective. Furthermore, the 47-a.a. $RSP3_{269-316}$ may harbor the Dpy-30 domain binding site. The in vitro experiment for mapping the precise binding site will be described later.

Distinct Dwarf RSs in RSP3 Mutant Axonemes.

Figure 5:
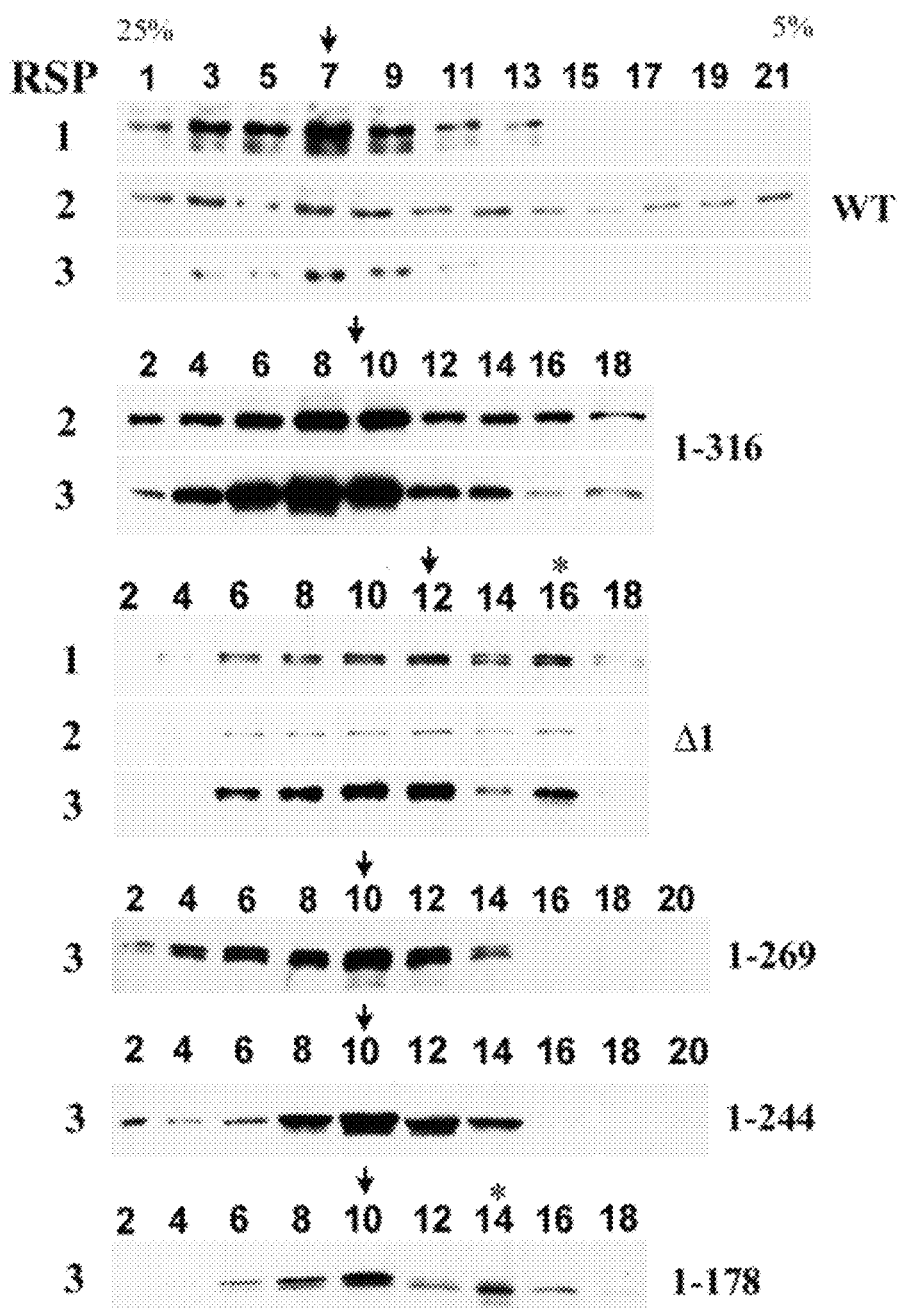
FIG. 5. Radial spokes extracted from RSP3 deletion mutants sedimented as smaller particles. The KI axonemal extracts from the indicated strains were centrifuged through a 5-25% sucrose density gradient and the fractions were assessed by western blots probed for relevant RSPs as indicated. The major peaks were indicated by arrows. The RSPs from all truncation mutants largely sedimented in a single peak as intact particles smaller than WT RSs. A prominent $2^{nd}$ RS peak (asterisk) was present in the gradients from Δ1 and 1-178 strains that lacked Coil 1.

To assess the RSs with truncated RSP3 independently, we investigated axonemes using two additional approaches. Firstly, RSs were extracted from axonemes and the dialyzed extract was fractionated by sucrose gradient velocity sedimentation. The fractions of the gradient were then assessed by western blots (FIG. 5). The RS complex from the WT control sedimented as an intact particle at 20S (Yang et al., 2001, arrow). For all other transgenic strains, RSs with truncated RSP3 sedimented near the middle of the gradient as smaller particles, similar to or smaller than RS stalk particles from the mutants lacking the head proteins (Yang et al., 2001). While the gradients of 1-244, 1-269 and 1-316 strains contain a single RSP3 peak (arrow), the gradients of the Δ1 and 1-178 strains that lack Coil 1 contained another minor peak (asterisk), suggesting that Coil 1, possibly through a coiled coil interaction, is critical to the stability of the RS complex.

Figure 6A:
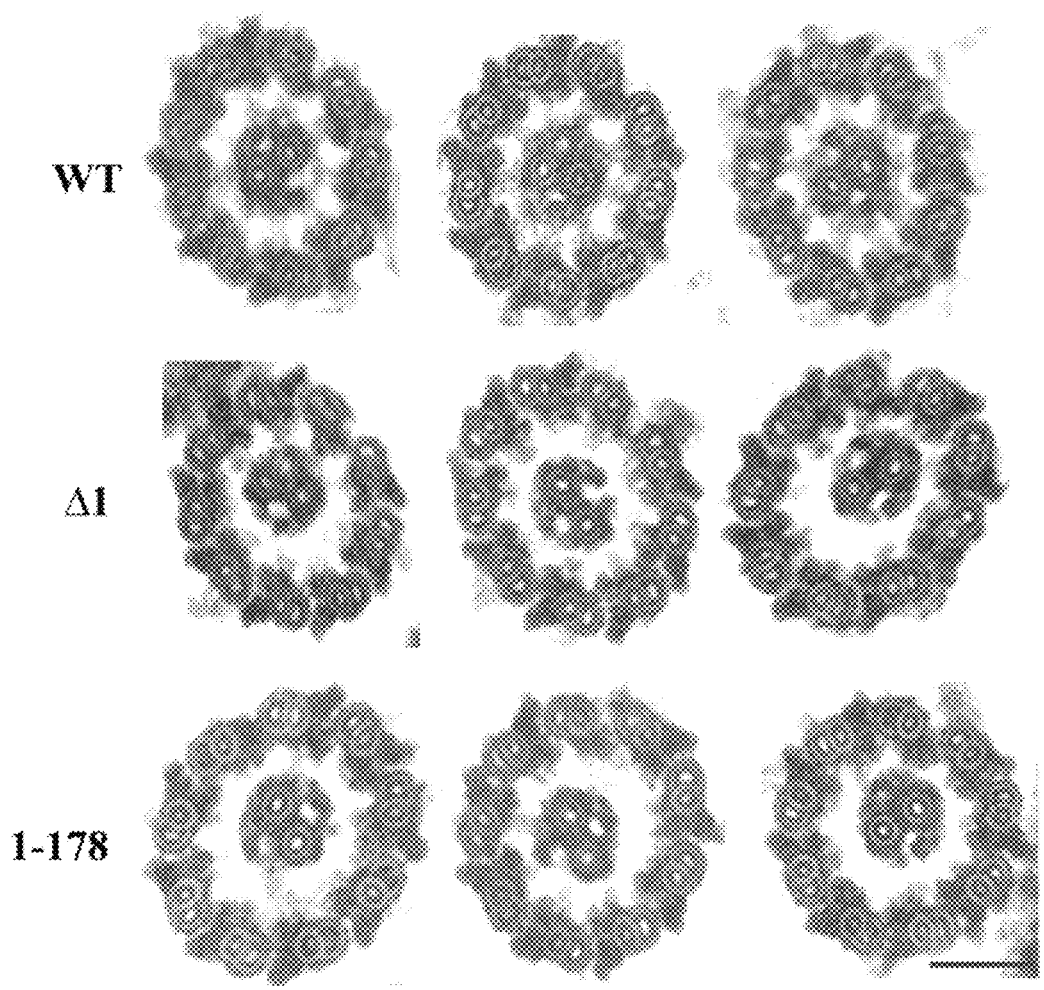
FIG. 6. Distinct stubby spokes in the axonemes from the Δ1 and 1-178 mutants. (A) The representative transmission electron microscopic images of cross-sectioned axonemes from the WT, Δ1 and 1-178 strains. The bottom panel gives an enlarged view of the axoneme cross sections. The arrows highlight representative radial spokes in each strain. The enlarged spokehead is present in the RSs of WT and Δ1 axonemes. Bar, 100 nm. (B) Schematic pictures depicting the RSs in each strain. (C) The length distributions of RSs in cross sectioned axonemes. The radial spokes with an identifiable morphology were measured from 13 WT sections; 24 Δ1 sections and 22 1-178 sections. Radial spokes were separated based on the spoke length and the number in each group was plotted into a distribution histogram.
Figure 6B:
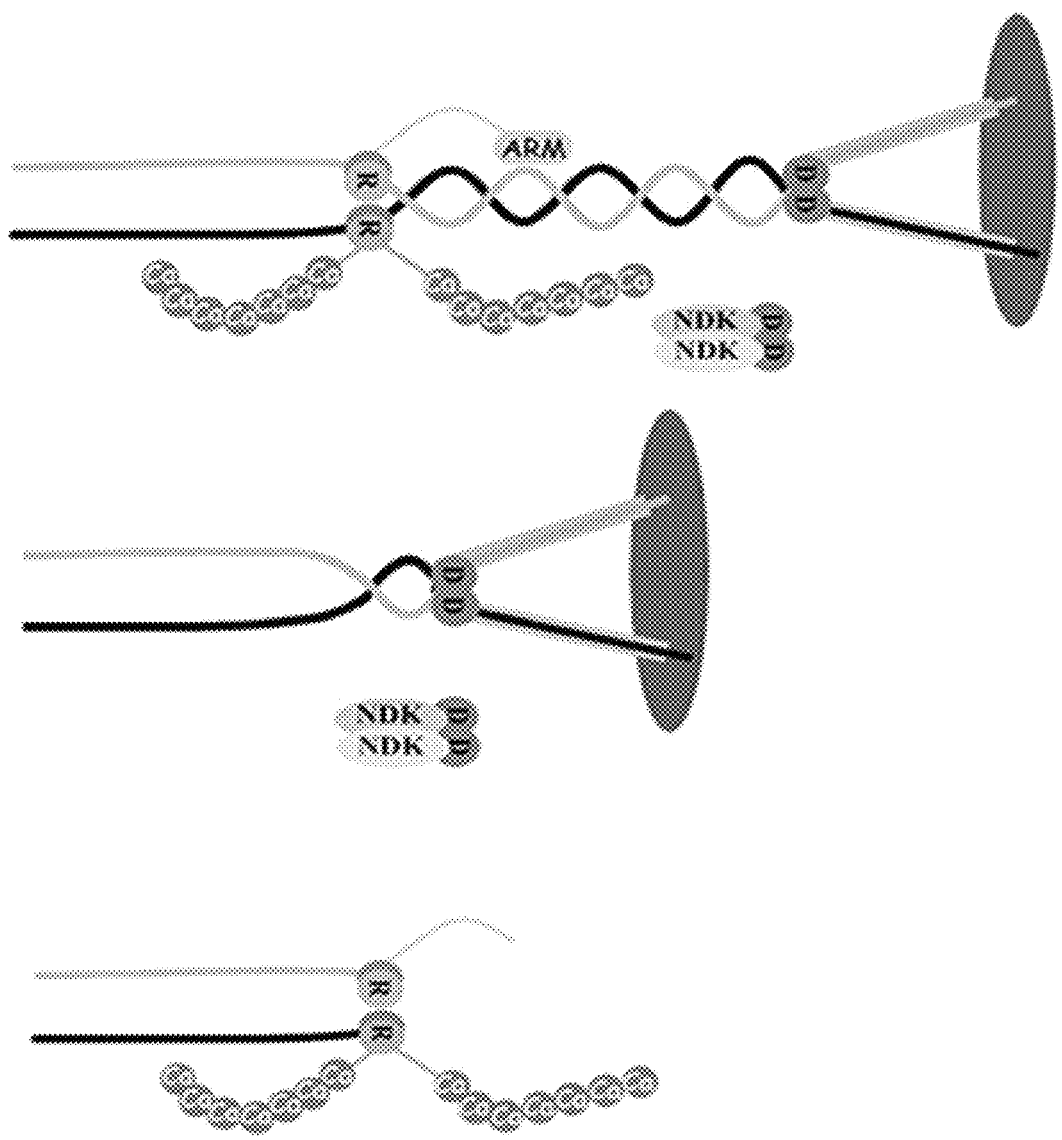

The morphology of the RS with truncated RSP3 was assessed by electron microscopy (EM). Due to the resolution of EM and the similar sizes of extracted RS particles from mutant flagella, we only compared the axonemes of WT, Δ1 and 1-178 strains (FIG. 6). The EM images of axoneme cross sections revealed two main defects, stubby RSs (arrows) and a lateral shift of the CP, a signature of RS deficiencies (Witman et al., 1978) (FIG. 6A and Table 2).

TABLE 2

| Strain | % with shifted CP[a] | # with measurable shift[b] | % of the shift[c] |
|---|---|---|---|
| WT | 3.7% (n = 27) | 0 | — |
| Δ1 | 92% (n = 38) | 14 | 16.6% |
|  |  | 3 | 15% |
|  |  | 2 | 20% |
| 1-178 | 69% (n = 39) | 9 | 16.6% |
|  |  | 5 | 20% |

[a]The percentage of axoneme cross sections in which the CP appeared shifting from the center by visual inspection.
[b]The number of axoneme cross sections in which the lateral shift of the CP was significant enough to be measured.
[c]% of the shift was derived from the distance between the centers of two central pair microtubules and the axoneme divided by the radius of the axoneme.

Figure 6C:
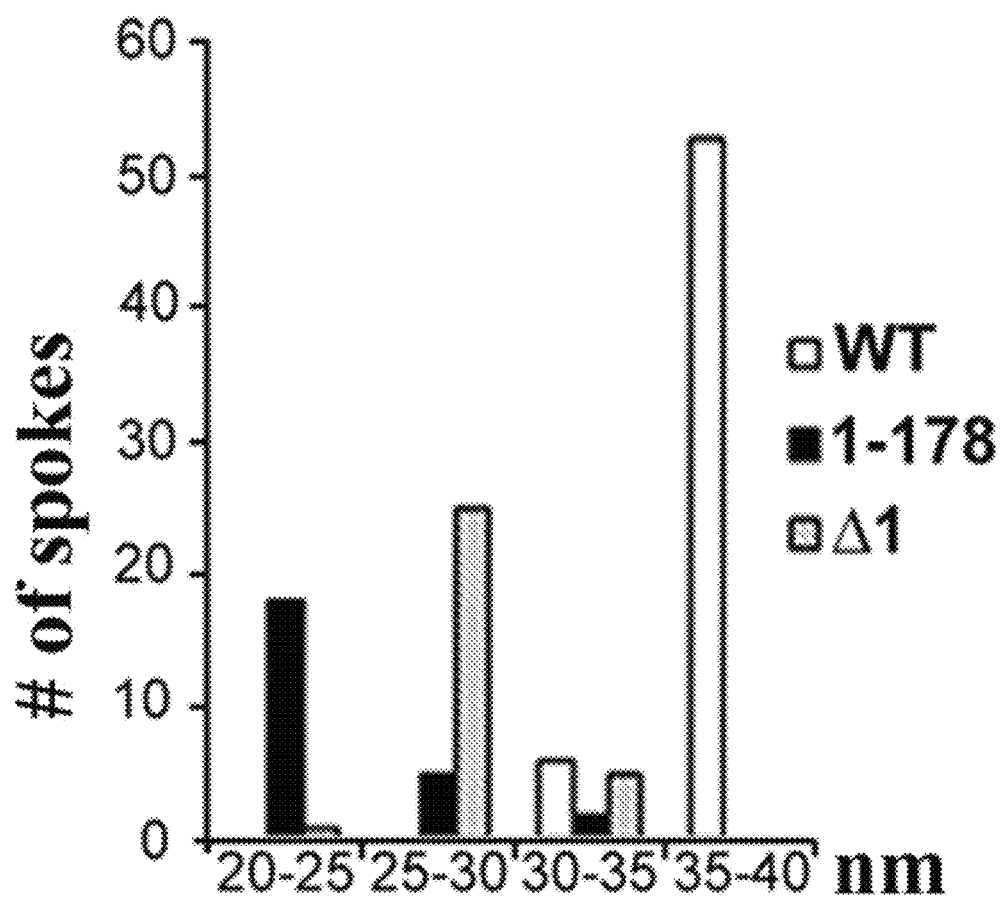

Table 2 illustrates the incidence of lateral-shifted central pair (CP) apparatus and the extent of deviation in electron micrograph of axonemes, where "n" is the total number of cross-sectioned axoneme images that were visually inspected. Importantly, some RS stubs in Δ1 axonemes but not 1-178 axonemes exhibited an enlarged head (bottom panel), consistent with the proposed model (FIG. 6B) and the presence of head proteins only in the Δ1 axonemes (FIG. 4). The RSs are the longest in the WT and the shortest in 1-178, that has the shortest RSP3 polypeptide (FIG. 6C). The CP shifted laterally in about 92% of Δ1 images and about 69% of 1-178 images (Table 2). The higher incidence of shifted CP in Δ1 axonemes despite their longer RSs than in 178 axonemes is consistent with the predicted interaction of the CP and the spokehead that is only present in Δ1 dwarf RSs (Warner and Satir, 1974) and may pull the CP away from the center.

Identification of the Dpy-30 Domain Binding Site in RSP3.

Based on the phenotypes of RSP3 transgenic strains (FIG. 4), an in vitro approach was taken to test that $RSP3_{269-316}$ contains a Dpy-30 domain binding site. RIIa-binding AHs are 14-18-a.a. long. Some of AHs are clearly comprised of ΦΦXX repeats in which the first two residues are hydrophobic residues (Φ) positioned to interact with complementary residues at the binding grooves of the RIIa domain (Burns-Hamuro et al., 2003; Kinderman et al., 2006; Sarma et al., 2010), whereas for the other RIIa-binding AHs the repeats are not as evident (Gold et al., 2006; Gaillard et al., 2001). Typical ΦΦXX repeats were noted within the Dpy-30 binding fragment in BIG1 at the trans-Golgi network but were not tested yet (Xia et al., 2010). For $RSP3_{269-316}$, typical and degenerate ΦΦXX repeats are present throughout this region, thus the precise Dpy-30 binding site was determined objectively by Ni-NTA pulldown. As a control, the His-tagged RIIa domain from RSP7 was co-expressed with the GST-tagged $RSP3_{96-180}$ that harbors $AH_R$ at a.a.#161-178 (Gaillard et al., 2001; FIG. 3) and both polypeptides were co-purified by Ni-NTA (FIG. 7A). Various Dpy-30 domain containing RSP2 and RSP23 polypeptides were tested but were not compatible for this assay due to poor expression or precipitation propensity. Therefore we used the His-tagged human Dpy-30 protein for Ni-NTA pulldown instead. As expected, both $GST-RSP3_{245-316}$ and $GST-RSP3_{269-316}$ were co-purified with His-Dpy-30 by Ni-NTA (FIGS. 7B and 7C). In contrast, the GST control was not co-purified (FIG. 7D).

Figure 7:
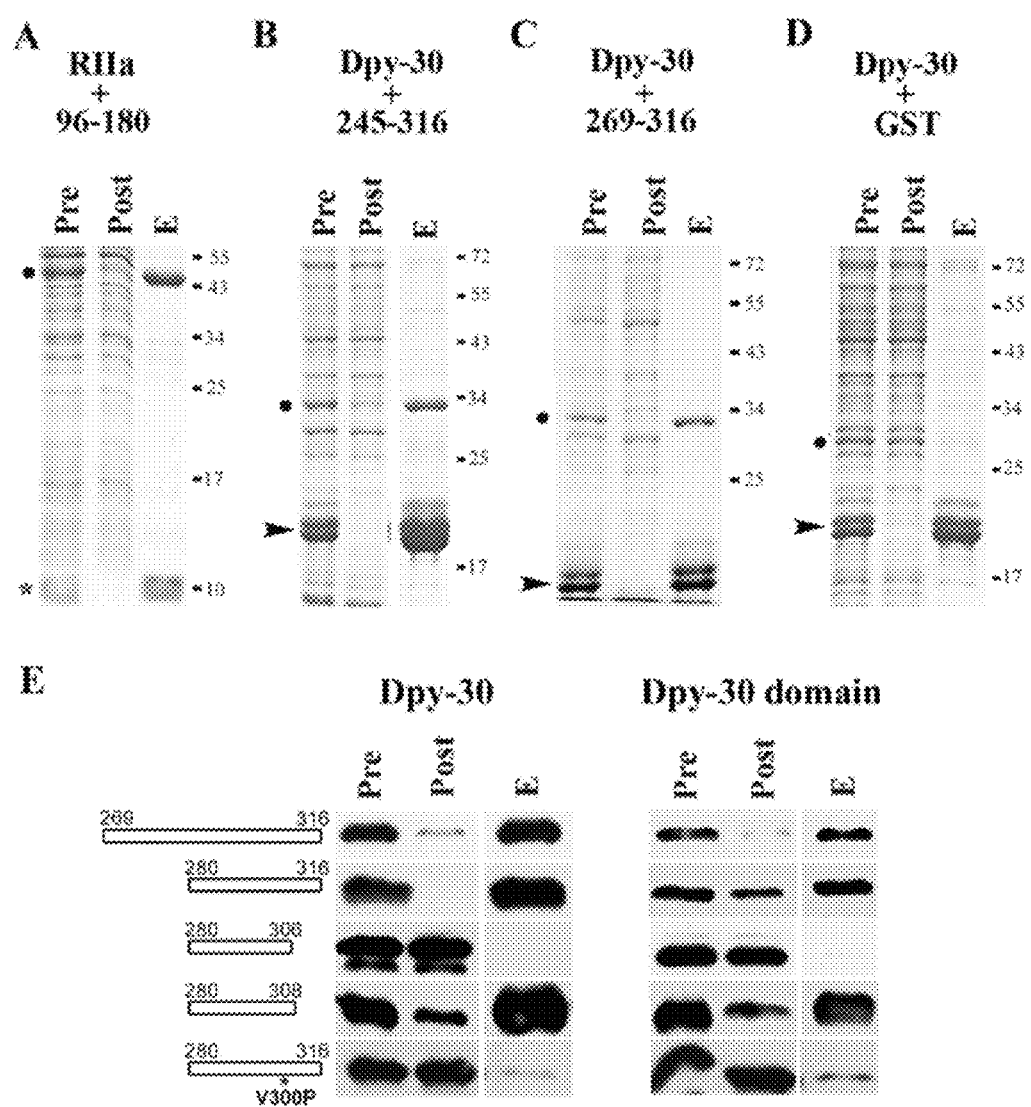
FIG. 7. Two sites in RSP3 bind to the RIIa and the Dpy-30 domain. His-tagged RIIa from RSP7 (asterisk) or His-tagged Dpy-30 protein (arrowhead) were co-expressed with a GST-tagged RSP3 peptide (dot) in bacteria. The Ni-NTA pull-down from the extracts was analyzed by Coomassie stained gel (A-D) or GST western blots (E). (A) The positive control, the co-purification of the RIIa domain and $RSP3_{96-180}$ that contains the RIIa-binding $AH_R$ (Gaillard, 2001). (B) and (C) The co-purification of His-tagged human Dpy-30 protein and GST-tagged $RSP3_{245-316}$ or $RSP3_{269-316}$ (dot). (D) The negative control. GST alone did not interact with Dpy-30 protein. (E) The smallest region that binds the Dpy-30 domain is a.a. #280-308 in RSP3. The interaction is perturbed by $V_{300}P$ mutation. His-tagged full-length Dpy-30 protein or the Dpy-30 domain only was co-expressed with GST-tagged RSP3 peptides as indicated. Pre, the bacterial extract; Post, the flow through from Ni-NTA matrix; and E, the eluate. Dpy-30 often migrated as double bands due to the susceptibility of its C-terminal end to proteolysis.

The experiments were further conducted on smaller segments within a.a.#269-316. $GST-RSP3_{280-316}$ and $GST-RSP3_{280-308}$, but not $GST-RSP3_{280-306}$, were also pulled down by His-Dpy-30 (FIG. 7E, left panel). This suggests that the Dpy-30 binding site is near the end of $RSP3_{280-308}$. To ensure that the co-purification occurs through the Dpy-30 domain rather than its flanking sequence, the same experiment was conducted with the Dpy-30 domain only (Dpy-$30_{45-99}$, Wang et al., 2009). The results from the experiments using Dpy-30 domain alone or full-length Dpy-30 protein were similar (FIG. 7E, right panel). Based on the similar dimensions of the RIIa and Dpy-30 domains (FIG. 1), we tested if the Dpy-30 binding peptide is centered on the 18-a.a. helix at the a.a.#291-308 by mutating $V_{300}$ in the middle of the region into P, a strategy used to study $AH_R$ (Gaillard et al., 2001; Carr et al., 1992). This $V_{300}$P mutation abrogated the binding of $RSP3_{280-316}$ to the full-length Dpy-30 and the Dpy-30 domain (FIG. 7, bottom row). Together, these results strongly suggest that the Dpy-30 domain binding site is within the 18-a.a. $RSP3_{291-308}$.

Figure 8B:
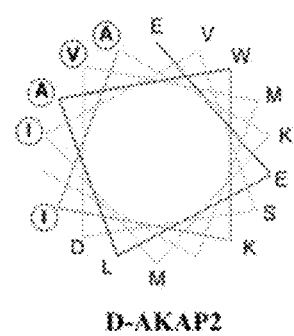
FIG. 8. Similarity of the RIIa and Dpy-30 domain binding sequences. (A) Alignment of RIIa- and Dpy-30-binding sequences in representative AKAPs and RSP3; and putative Dpy-30 binding sequence in Ash2 and BIG1. These regions contain three or four 4-a.a. repeats in which the first two residues are often, but not always, hydrophobic residues (black boxes). No particular conserved residues distinguish the two groups of sequences. D-AKAP2 is a dual specific AKAP that binds the RIIa domain in RI and RII of PKA. The alignment for RSP3 sequences is generated by Multiple Sequence Alignment program and based on Gaillard et al. (2001). The alignment of AH sequences from AKAPs is based on Kinderman, et al., (2006) and Gold et al., (2006). The precise Dpy-30 binding sites in Ash2 and BIG1 remain to be tested. RII-AKAP, Q12802; RI-AKAP, AAC24507; C.r., *Chlamydomonas reinhardtii*; C.e., *Caenorhabditis elegans*; D.r., *Danio rerio*; H.s., *Homo sapiens*; S.c., *Saccharomyces cerevisiae*. (B) Helical Wheel plots of RIIa- and Dpy-30 binding sequences from D-AKAP2 and *Chlamydomonas* RSP3 (asterisk in A). One side of the RSP3's Dpy-30-binding helix is enriched with hydrophobic residues (bold and circled) like $AH_D$ that binds RIIa and thus this region is designated as $AH_D$.
Figure 8B:
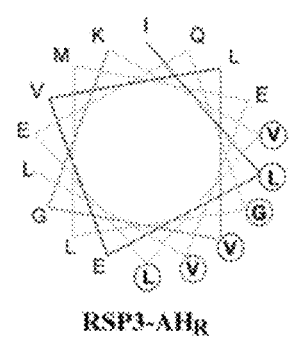
Figure 8B:
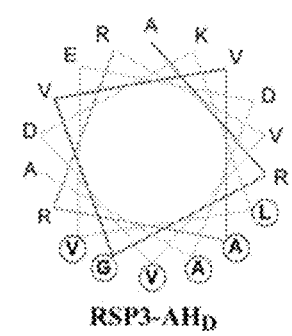

Comparing the RIIa clan domains and their binding sequences. We compared $RSP3_{291-308}$ with representative RIIa-binding sequences (FIG. 8A). As reported previously, typical and degenerate ΦΦXX repeats (left panel) are noticeable in the AH of AKAPs that bind PKA's RI (RI-AKAP), RII (RII-AKAP), or both (D-AKAP2) and in $AH_R$ at $RSP3_{160-178}$ and the equivalent region in RSP3 orthologues. Likewise the loosely defined repeats are present at $RSP3_{291-308}$, the counterparts in RSP3 orthologues and a helix within the Dpy-30 binding fragments in BIG1 (Xia et al., 2010) and in Ash2 (South et al., 2010) (right panel). Like $AH_R$ in D-AKAP2 or at $RSP3_{160-178}$, $RSP3_{291-308}$ can be plotted into an AH by the Helical Wheel program (FIG. 8B), in which the hydrophobic residues (bold circled letters) are enriched at one side of the helix. Hence, the Dpy-30 binding helix in RSP3 is referred here as $AH_D$. Despite the differences between the Dpy-30 domain and RIIa domains and their distinct locations in the RS (FIG. 1), both associate with AHs of similar a.a. patterns.

The similarity of $AH_R$ and $AH_D$ prompted us to align the crystal structures of the Dpy-30 domain and the complexes of $AH_R$ from the dual specific D-AKAP2 and the RIIa domain from the RI and RII subunit (Wang et al., 2009; Kinderman et al., 2006; Sarma et al., 2010) (data not shown). The N-terminus of both RI's RIIa and Dpy-30 were observed to form an α-helix that contributes to a deep pocket for the AH. In contrast, the N-terminus of RII's RIIa is a β-strand which contributes to a shallower binding cleft. The $AH_R$ rests in the binding clefts from the two RIIa domains in a similar fashion except for a shift in helical register (Sarma et al., 2010). The binding pocket of the Dpy-30 domain bears close resemblance to both RIIa domains but more so to RI's RIIa because of their common α-helix at the N-terminus. Nonetheless, all structures are highly similar and are able to accommodate $AH_R$. Thus, with regards to tertiary structure, the RIIa and Dpy-30 domain are not as distinctive as their classification.

Dpy-30 Binds $AH_R$ in RSP3 In Vitro.

Figure 9:
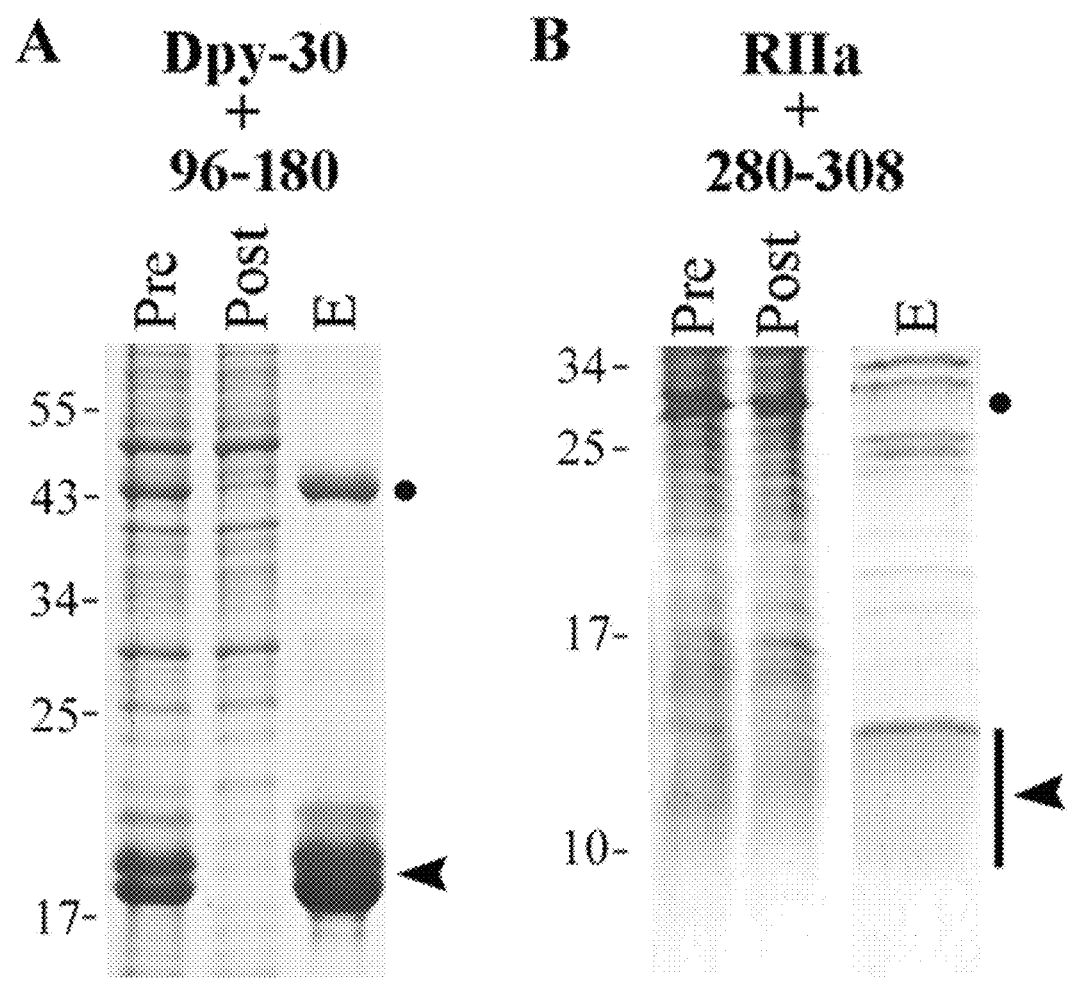
FIG. 9. Cross recognition of the Dpy-30 domain and RSP3-$AH_R$. (A) His-tagged Dpy-30 protein (arrowhead) or (B) His-tagged RIIa domain from RSP7 (line and arrowhead) was co-expressed with GST-tagged RSP3-$AH_R$ or $AH_D$ respectively (dot). The extract was subjected to Ni-NTA affinity chromatography and the samples were analyzed by Coomassie-stained gel. RSP3-$AH_R$ in the bacterial extract (Pre) was mostly depleted after incubation with the Ni-NTA (see the flow through, Post) and was enriched in the eluate (E). In contrast, RSP3-$AH_D$ did not bind to the His-tagged RIIa domain, appearing similar in the Pre and the Post; and negligible in the eluate.

Based on the structural similarity, we tested for the cross-recognition of His-Dpy-30 and $AH_R$ (GST-RSP3g); and RSP7's RIIa and $AH_D$ ($GST-RSP3_{280-308}$) by the described Ni-NTA pulldown assay. His-Dpy-30 pulled down the mismatched $AH_R$ (FIG. 9A), while His-RIIa did not significantly pull down the mismatched $AH_D$ (FIG. 9B). Thus Dpy-30 that has a deep pocket from an additional α-helix recognizes both $AH_R$ and $AH_D$, whereas RSP7's RIIa, as PKA's RII, only binds RSP3's $AH_R$ (Gaillard et al., 2001). The pocket depth in D/D domains does not seem related to the specificity. Consistent with this, the less diverse AH partners of RI compared to RII that has a shallow AH-binding groove is attributed to the RI-unique disulfide bonds that restrict the flexibility of the additional α-helix (Banky et al., 2003; Sarma et al., 2010). From the perspective of AHs, RSP3's $AH_R$ is analogous to a dual-specific $AH_R$ that binds both RI and RII, while RSP3's $AH_D$ appears to be monospecific.

Discussion

A New RS Model with Dimeric RSP3 as a Structural Scaffold.

The results from motility, biochemical and morphological analyses consistently support the proposed model (FIG. 2C). The two $AH_D$s in a RSP3 dimer anchor the Dpy-30 domain present in RSP2 and RSP23. The nearby sequences in dimeric RSP3 and in dimeric RSP2 further interact with each other and with the head components, leading to a Y-shape spokehead, consistent with the Y-shaped images revealed by the recent cryotomographic studies (Pigino et al., 2011; Barber et al., 2012). As for RSP23, the Dpy-30 domain could tether the associated NDK to the RS complex for an unknown purpose. Based on the co-assembly of RSP2 and RSP23 (Patel-King et al., 2004), we speculate that the two RIIa-containing proteins are also located in the same RS. Alternatively, the two RIIa-containing proteins may respectively localize in spoke 1 and spoke 2 in each 96-nm axonemal unit. Or they might form heterodimers. Regardless the precise arrangement, RSP11's short flanking sequence and the tethered the ARM repeat protein (RSP8) interact with the Coil 1 region in RSP3 directly or indirectly, constitutively enhancing the rigidity of the dimeric RSP3 core to prevent paralysis in the exhausted media as exhibited by RSP11 mutants (Yang and Yang, 2006). On the other hand, EF-hands in RSP7 may allosterically modulate the stalk when calcium increases, analogous to the cAMP-induced allosteric regulation of PKA. Taken together, the collective evidence strongly suggests that dimeric RSP3 is a bona fide core scaffold of the entire RS complex. The various effectors anchored through AH-D/D domain interactions facilitate the assembly of the RS and possibly modulate the scaffold itself in a calcium-dependent and independent manner.

The single AH-D/D system for anchoring various effector mechanisms. Such an anchoring system is not restricted to the RS, flagella or *Chlamydomonas*. RSP3 and its $AH_R$ and $AH_D$ are conserved, as are Dpy-30-domain-containing NDK and potential RSP2 orthologues that were found to be partners in the human interactome (Rual et al., 2005). Neither will RSP3 be the only AKAP that binds non-PKA RIIa clan members. AKAP3 and a non-PKA RIIa clan member were pulled down together from testis extract, while RIIa clan members are not only located in cilia and flagella (Newell et al., 2008). As for the Dpy-30 protein, it may function primarily in the nucleus and trans-Golgi network (Xu et al., 2009). Thus AHs and D/D domains constitute a versatile system to anchor PKA and a wide spectrum of reactions in different cellular compartments.

The interactions of RSP3's $AH_R$ with RII in vitro but with RSP7 and RSP11 in vivo firmly establish the functional equivalence of RIIa domains. This equivalence is also true for the Dpy-30 domains—Dpy-30 in the histone methyltransferase complex recognizes $AH_D$ in the RS. Furthermore, $AH_R$ and $AH_D$ share a similar pattern while $AH_R$ even recognizes both RIIa and Dpy-30. These findings strongly suggest that the interaction of diverged D/D domains and AHs employs an identical principle. This highlights the importance of using physiological evidence to interpret the effector mechanism while accentuating the question about specificity in vivo. How are the various effector mechanisms anchored to specific locations in the RS and in the cytoplasm? A dual-specific $AH_{R/D}$, albeit conceivable from the structural perspective, could potentially misplace the spoke subunits in the RS or target Dpy-30 to AKAPs. There is no evidence that such mis-targeting has occurred and thus mechanisms must be in place to ensure correct localization. One such cue could be differential affinities. In general, the affinity of the AHs for RI is lower than that for RII (Herberg et al., 2000; Sarma et al., 2010; Means et al., 2011) and those with a higher affinity may interact first. Or the sequences flanking AHs and D/D domains may contribute to the specificity. The flanking sequences augment the recognition of RI and dual-specific AKAPs (Jarnaess et al., 2008) and may explain the assembly of RSP7 and RSP11 in the RS (FIG. 3) despite the abolished $AH_R$(Gaillard et al., 2006). In such scenarios, flanking sequences may provide recognition while the AH and D/D domain are more about docking than specific targeting as perceived currently. Although thought provoking, dual specific AHs are relatively rare. Most AH sequences, possibly including RSP3's $AH_D$, are monospecific because of distinct a.a. residues (Burns-Hamuro et al., 2003; Alto et al., 2003; Angelo and Rubin, 1998; Hirsch et al., 1992).

While AKAPs are known as signal transduction scaffolds, the function of AH-containing proteins may be as functionally diverged as the RIIa clan family members that they anchor. RSP3 not only anchors effectors related to signal transduction but also serves as the structural scaffold that anchors molecules involved in assembly. Similar dual roles may be applicable to BIG1 and BIG2, two large paralogous molecules forming heterodimeric scaffold, in the trans-Golgi network. Aside from binding to molecular switches that regulate membrane trafficking, they contain 1-3 AHs for anchoring RIIa- or Dpy-30-domain containing proteins (Xia et al., 2010; Li et al., 2003), some of which may play a structural role. On the other hand, monomeric Ash2 that interacts with Dpy-30 and multiple molecules that lack signaling moieties in the Set1-like histone methyltransferases (Patel et al., 2009; Cho et al., 2007; Cao et al., 2010; Chen et al., 2011) could be primarily a structural scaffold. This versatile AH-D/D system highlights the need of a new term to complement "AKAPs", which implies exclusively PKA anchoring and signal transduction scaffolds. We propose to use D/D-domain Anchoring Proteins (DAPs) to encompass what appears to be a much broader spectrum of molecules that anchor various RIIa clan members.

Materials and Methods

Cell Strains, Culture Conditions and Biochemistry.

*Chlamydomonas reinhardtii* wild-type strain (CC-124) and paralyzed RSP3 mutant strain (pf14) were used in this study. Cells were cultured in Tris-acetate-phosphate (TAP) medium with aeration over a 14 hr/10 hr light-dark cycle. Axoneme biochemistry was conducted at 4° C. as described previously (Yang et al., 2008) with minor modifications. Following sedimentation of cells at 1,800×g for 8 min and dibucaine deflagellation, flagella were centrifuged down at 11 K×g and demembranated with 0.5% NP-40. For velocity sedimentation, RSs were extracted from the axoneme pellets with 0.6 M KI at 5 mg/ml and the extract was sedimented through a 5-25% sucrose gradient at 220 K×g for 14 hours.

Genomic DNA Constructs.

An NcoI fragment containing the RSP3 genomic sequence was released from a BAC clone and inserted into the same site in pGEM-T Easy vector (Promega). The SacI site and its downstream sequence in the 3' flanking region were eliminated by limited restriction digest followed by treatment with T4 DNA polymerase (New England Bio-Labs) and ligation. PCR with modified primers was performed to add the sequence for 6 His codons flanked by an XhoI site at one end and the endogenous stop codon followed by an Xba site at the other end. Subsequently, into the XhoI site a PCR product containing 3HA-6His coding sequence was inserted. This fragment was amplified using the p3HA plasmid (Silflow et al., 2001) as a template. This final RSP3 genomic construct, pRSP3-HAHis, expressed a polypeptide with a 3 HA and 12 His tag. This construct was used to create all the mutant constructs with a PCR based approach. S and AS in primer names denote sense and antisense directions. To create the Δ1 construct, deleting the Coil 1-coding sequence, the sequences flanking Coil 1 (171-244 a.a.) were amplified from pRSP3-HAHis vector using the following primer pairs: XbaS (tccaactctaca<u>tctagag</u>ctcgcagagagg) (SEQ ID NO:14) and XhoAS (tctccatcaggccct<u>gctcgag</u>caccttgcccac) (SEQ ID NO:15); and XhoS (tctcgagctgtctggcattgtcaacacggtg) (SEQ ID NO:16) and AS (tcttgtccgcctcccacttggcgttg) (SEQ ID NO:17). The PCR products Xba-Xho (1055 bp) and Xho-AS (370 bp) were ligated into the pRSP3-HAHis construct digested with Spe and Not enzymes. Xba and Spe digestions generated identical adhesive ends compatible for ligation but the ligated mutant construct lost the Spe site, distinct from the parental clones. This mutated construct was further modified by adding the paromomycin (PMM) resistance cassette from pSI103 plasmid (Yang et al., 2008) into the AatII site in the vector to aid the selection of transgenic strains. The final plasmid is designated as pΔ1PMM. To create the Δ2 construct, sequences flanking Coil 2 coding region was amplified from pRSP3-HAHis using SpeS (ccgcaagctcactcgttcaccataaac) (SEQ ID NO:18) and NotAS (a gcggccgcgcgattggctgccagcgccgccgc) (SEQ ID NO:19) primers. The amplified fragment was ligated into pΔ1PMM vector digested with Spe and Not.

To generate the remaining RSP3 constructs, the PMM cassette was first cloned into the AatII site in pGEM-T Easy to create pGEM-PMM. To create $RSP3_{1-178}$ construct, two fragments were amplified from the pRSP3-HAHis construct. The first fragment which extended from the 5'UTR to the codon for a.a.#178 was generated using a sense primer with a built-in EcoRI site (EcoRIS: ggaattccgctctgctctccagtccgactaggg) (SEQ ID NO:20) and an antisense primer with a built-in Xba site (XbaAS3: gctctagactcctcctcctccagcacctccatcag) (SEQ ID NO:21). The second fragment which extended from the HAHis tag to the 3'UTR was generated using a sense primer with a built-in Xba site (XbaS: gctctagacgccagggtgctgcgattggctgcc) (SEQ ID NO:22) and an antisense primer with a built-in EcoRI site (RIAS: ggaattctgttgcctgagagctccgcctcggcc) (SEQ ID NO:23). To create the $RSP3_{1-244}$ construct, flanking sequences were amplified using the same set of primers for make $RSP3_{1-178}$ except XbaAS3 was replaced with the XbaAS2 primer (gctctagaccgcgcgcaaaggcgctggccgcc) (SEQ ID NO:24). To create $RSP3_{1-316}$ construct, XbaAS2 primer was replaced by the XbaAS1 primer (gctctagacgccagggtgctgcgattggctgcc) (SEQ ID NO:25). Each paired EcoRI-Xba and Xba-EcoRI PCR fragments were ligated into the EcoRI site in pGEM-PMM. To create $RSP3_{1-269}$ construct, two fragments were amplified from the pRSP3-HAHis construct. The first fragment which extended from the 5'UTR to the codon for a.a. #269 was generated using the EcoRIS primer (described above) and the ICAS primer with a built-in Xho site (ac ctcgaggggtcgtagatgtagccgct) (SEQ ID NO:26). The second fragment which extended from the HAHis tag to RSP3's 3'UTR was generated using the XhoS primer with a built-in Xho site: acctcgagcaccaccaccaccaccactaagctagaggg) (SEQ ID NO:27) and the RIAS primer (described above). The two fragments (RI-Xho and Xho-RI) generated by PCR, were also ligated into the EcoRI site in pGEM-PMM.

cDNA Constructs.

The constructs expressing GST-tagged $RSP3_{96-180}$, $RSP3_{245-316}$ and $RSP3_{269-316}$ were generated by first PCR amplifying the corresponding sequences using a GST-RSP3 cDNA construct as a template (Diener et al., 1993). PCR products were then inserted into BamHI and EcoRI sites in pGEX-2T vector. The pGEX-$RSP3_{245-316}$ was used as a template to amplify the coding sequence for GST-tagged $RSP3_{280-316}$, $RSP3_{280-306}$ and $RSP3_{280-308}$. The PCR products were cloned into the NcoI and EcoRI site in pET-Duet vector (Novagen). The $V_{300}$ codon in $pRSP3_{280-316}$ was replaced with the proline codon using QuikChange Site-Directed mutagenesis strategy (Stratagene). The resulting plasmid was named $pRSP3_{V300P}$. To create the $HRSP3_{301-325}$ construct, the GST-coding sequence was amplified from pGEX-2T and the RSP3 coding sequence was amplified from a human RSP3 cDNA clone. Both fragments were fused by PCR and the joint product was inserted between NcoI and EcoRI site in pET-Duet vector. To create the His-tagged human Dpy-30, full length or 45-99 a.a., the corresponding sequences were PCR amplified from a commercial available cDNA clone and inserted between the Nde and Xho site in pET-28a vector. For expression of recombinant proteins, all constructs were transformed into BL21 (DE3) cells. The cultures were induced with 1 mM IPTG overnight at 18° C.

Transformation of Chlamydomonas.

All genomic constructs were transformed into the RSP3 mutant pf14 using the glass beads method (Kindle K L, 1990). Briefly, autolysin-treated cells were washed with TAP medium and resuspended in the same solution to a final concentration of $1 \times 10^8$ cells/ml. Plasmid (1-2 μg), glass beads and 100 μl freshly prepared 20% PEG was added to 500 μl of the cell suspension. This mixture was vortexed for 45 sec followed by immediate suspension with 10 ml TAP media. The cells in the suspension were spun down and resuspended in fresh TAP media and recovered under light overnight. The following day cells resuspended in TAP media were plated on TAP agar plates containing 10 μg/ml PMM. Single colonies that appeared after 4-5 days were transferred to fresh TAP plates. A fraction of each colony was resuspended in 200 μl TAP media in 96-well plates for observation using a compound microscope (Olympus BH-2).

In-Vitro Binding Analysis.

For Ni-NTA (Qiagen) affinity co-purification, GST-tagged RSP3 constructs and His-tagged HDpy-30 constructs were co-transformed into BL21(DE3) cells. The recombinant proteins were induced using 1 mM IPTG overnight at 16° C. Following induction, the cell pellet from a 5-ml culture was resuspended in 750 μl lysis buffer and sonicated using Branson digital Sonifier (Emerson Industrial Automation). The sonicated mixtures were centrifuged at 4° C., 12,000 rpm for 25 min. The supernatant was incubated with 100 μl Ni-NTA for 1 hour at room temperature. The matrix was subsequently washed thrice and elution was carried out as instructed by the manufacturer.

Western Blot.

For SDS-PAGE, protein samples were mixed with 5× Laemmli samples buffer and boiled for 5 min. In general, samples from 10-20 μg axonemes, or 10 μl bacterial samples were loaded in each lane in acrylamide gels of different percentage varying from 7% to 14% based on the molecular mass of proteins to be examined. RSP7 that co-migrated with tubulins was resolved in 10% gels. Following electrophoresis, proteins were transferred to nitrocellulose membranes and the blots were probed with the antibodies as indicated. Anti-RSP2 and anti-RSP23 were raised in rabbits with Ni-NTA-purified recombinant polypeptides of Chlamydomonas $RSP2_{7-119}$ and $RSP23_{1-201}$. Rabbit anti-RSP3 was raised against His-tagged recombinant human RSP3. The other rabbit polyclonal antibodies for the axonemal proteins were described previously (Yang et al., 2006). Briefly, anti-RSP1, -RSP4 and -RSP6 antibodies were raised against proteins purified from 2-D gels. Anti-RSP11 and anti-RSP16 were raised against respective Hi-tagged fusion proteins. Anti-RSP8 was raised against conjugated RSP8's C-terminal fragment. Anti-HA polyclonal antibody was from Covance Inc (CA). Anti-GST monoclonal antibody was from Genscript (NJ). Anti-RSP7 was raised in chicken against a purified 25-kD His-tagged RSP7 C-terminal fragment. The anti-RSP7 IgY was used at 1:1,000 dilution while, the other primary and $2^{nd}$ antibodies, were used at 1:5,000 dilutions in 5% dry milk in Tris-Buffer-Saline, pH 7.4.

Electron Microscopy.

Axonemes from WT, $RSP3_{1-178}$ and Δ1 strains were prepared by two methods: (1) a standard EM procedure with a 2.5% glutaraldehyde and cacodylate buffer primary fixative, osmium secondary fixative, dehydrated in ethanol, en bloc stained, and embedded in PolyBed resin; (2) primary fixation with 1% tannic acid, 1% glutaraldehyde in cacodylate buffer (modification of Mitchell and Sale, 1999), osmium secondary fixative, and dehydrated in ethanol, en bloc stained, and embedded in PolyBed resin. Gold-silver sections were double stained with lead citrate and uranyl acetate and examined at a magnification of 80 k with a Zeiss T109 electron microscope with Gatan Digital Micrograph software operating at 80 kV. Focused axoneme cross-sections (approximately 50 from each type of flagella and from each fixation) were analyzed further. The lengths of radial spokes were measured and plotted into a distribution histogram. The number of axonemes with a central pair that was visibly deviated was divided by the number of total axonemes examined to generate the percentage of axonemes with a deviated central pair. For axonemes in which the deviation was substantial to be measured, the maximum difference in the distance from the middle of the central pair to the inner edge of the opposing outer doublets was determined as the deviated distance. This length divided by the average radius was computed as percentage deviation.

Sequence Analysis.

Protein secondary structure was analyzed using the Hierarchical Neural Network (HNN) predict program. The COILS program was used to assess the propensity of coil formation. (See Lupas, A., et al. (1991) Predicting Coiled Coils from Protein Sequences Science 252:1162-1164; Lupas, A. (1996) Prediction and Analysis of Coiled-Coil Structures Meth. Enzymology 266:513-525; Parry, D. A. D. (1982) Coiled-coils in alpha-helix-containing proteins, Biosci. Rep. 2:1017-1024). Amphipathic helices were plotted using the Helical Wheel program.

Example 2. The Distinctions of the D/D-Domain-Binding Amphipathic Helices in Ash2 and AKAPs Abstract The Dpy-30 domain is present in proteins crucial for functions as diverse as chromatin modification and flagellar beating. Its tertiary structure bears great resemblance to that of RIIa, the dimerization and docking domain in the cAMP-dependent protein kinase (PKA) for docking the tetrameric holoenzyme to the hydrophobic patch of an amphipathic helix (AH) in a number of A-kinase anchoring proteins (AKAPs). In flagella, the Dpy-30 domain binds to an AH near the bifurcation point of the Y-shaped radial spoke complex in flagella. Here we demonstrate that, likewise, in the Y-shaped core complex of Set1/MLL/Compass-like histone methyltransferases, the Dpy-30 domain in Dpy-30 protein binds to an AH in Ash2. This AH with conserved charged residues at unexpected positions exhibits low affinity for RIIa but becomes dual specific by a mutation of a conserved glutamic acid. This finding sheds light on the extraordinary diversity of these similar molecular modules for forming or localizing various vital complexes of bilateral symmetry and on applications of AHs in specific functional perturbations.

Introduction

The discovery of A-kinase anchoring proteins (AKAPs) gave rise to the concept that signal transduction pathways in eukaryotic cells are organized spatially (reviewed by Welch et al., 2010). The cAMP-dependent protein kinase (PKA) is a tetrameric holoenzyme with two identical regulatory subunits that each binds to a catalytic subunit. Two identical regulatory subunits, RI or RII, also undergo homodimerization through their RIIa domain. On the surface of RIIa dimer is a groove with strong hydrophobicity for associating with AKAPs' amphipathic helix (AH) (Newlon et al., 2001). Aside from the AH, typical AKAPs, which differ significantly in sequences, harbors additional binding sites for other molecules involved in signal transduction (Klauck et al., 1996; Scott and Paulson, 2009). Through this paradigm, PKA, the key effector of the cAMP signaling pathway, capable of spurious phosphorylation, is targeted near its intended substrates and other signaling pathways at various subcellular compartments for integrated and precise regulation. High affinity AHs for RIIa domains have been developed for perturbing the AH-D/D interactions and the localization of PKA in cells (Alto et al., 2003; Burns-Hamuro et al., 2003; Carlson et al., 2006). Targeting function of AKAPs proves to be critical for human health (Kammerer et al., 2003; Mauban et al., 2009)

After numerous proteins were discovered in recent years, it became evident that domains resembling RIIa, the ~40-a.a. dimerization and docking (D/D) domain of PKA, are present in hundreds of proteins. For some, the similarity is evident in primary sequences (Fujita et al., 2000; Carr et al., 2001; Yang and Yang, 2006; Newell et al., 2008), while for the others, the common feature is limited to the helix-loop-helix secondary structure and the tertiary structure. Upon dimerization, the peptides fold into an X-type four-helix bundle preceded by either a short β-strand or α-helix (Roguev et al., 2001; Banky et al., 2000; Wang et al., 2009) that is involved in AH binding as well (Banky et al., 2003; Gold et al., 2006; Kinderman et al., 2006; Sarma et al., 2010). Based on primary sequences, in the protein family database, Pfam (see Wellcome Trust Sanger Institute Pfam 26.0 database website), these proteins are categorized into two families in the RIIa clan, RIIa and Dpy-30, the latter named after the *C. elegans* gene. Aside from the common domain, the rest of the sequences in the RIIa clan members diverge significantly. Many are predicted to form distinct functional moieties, whereas a few are feature-less and rather short. It seems contradictory that the basic interacting modules for targeting a master molecular switch ends up in hundreds of molecules with diverged functions.

It is particularly intriguing that four RIIa clan members are subunits of the radial spoke, a Y-shaped complex in eukaryotic flagella (Pigino et al., 2011; Barbar et al, 2011) for regulation of oscillatory beating (Lindemann, 2007; Warner and Satir, 1974)—two with a RIIa domain and two with a Dpy-30 domain (Yang et al., 2006; Patel-King et al., 2004). None of them contains the other domains of PKA that are necessary for the cAMP signal transduction. However, the flagella of a *Chlamydomonas* mutant defective in an RIIa spoke protein are paralyzed reversibly depending on the condition of culture media (Yang and Yang, 2006), whereas the flagella defective in a Dpy-30 member are permanently paralyzed, defective the head part of the radial spoke (Huang et al., 1981; Yang et al., 2004; Pigino et al., 2011). This reveals the general significance of the RIIa clan members. Recently, we found that a dimeric scaffold protein in the radial spoke has two AHs—each for binding the RIIa domain or the Dpy-30 domain (unpublished). This finding demonstrated the single interacting principle for the diverse members. The question is how Dpy-30 protein employs this principle in the cell body.

Among the RIIa clan members, Dpy-30 is particularly interesting because it interacts with many important molecules despite of its small size (~100 a.a.) with no discernable functional moiety other than the Dpy-30 domain. It associates with BIG1, a guanine nucleotide exchange factor (GEF) at the trans-Golgi network (Xu, 2009) and also resides in a number of chromatin modification complexes in numerous metazoans and single cell organisms, such as X-chromosome dosage compensation complex (Pferdihert et al., 2011) and various Set/MLL/Compass-like histone methyltransferases (HMT), which exert transcriptional control and epigenetic regulation by methylating the lysine 4 residue in histone 3, H3K4, in master genes (reviewed by Mohan et al., 2010). The C. elegans mutant defective in Dpy-30, the namesake of the domain, exhibits a dumpy body shape (Hsu et al., 1994). In mammals, the complex appears to be involved in the carcinogenesis of mixed lineage leukemia (MLL) (Mohan et al., 2010), whereas knocking down Dpy-30 blocks H3K4 tri-methylation and neuronal differentiation from pluripotent stem cells, although mono- and di-methylations are less affected (Jiang et al., 2011).

In fact, Dpy-30 and three polypeptides—Ash2, Dpy-30 and two WD-repeat-containing proteins, RbBP5 and WDR5—form a core complex that is present in various HMT complexes from a wide range of organism (Cho et al., 2007; Patel et al., 2011; Takahashi et al., 2011). Independent evidence suggests that each subunit interacts with every other subunits (FIG. 10) and additional molecules outside the core complex (for example, Dou et al., 2006; Steward et al., 2006; Southall et al., 2009; Rual et al., 2010; Mak et al., 2010; Stoller et al., 2010; Cao et al., 2010). For instance, Ash2 contains two major structural moieties: the PHD-WH domain that binds DNA (Avdic et al., 2011; Chen et al., 2011), and the SPRY domain that interacts with the WD-repeat proteins (Chen et al., 2012). Dpy-30 also interacts with the two WD repeat proteins and the C-terminal region after the SPRY domain in Ash2 (South et al., 2010). Refining the molecular interaction between Ash2 and Dpy-30 could clarify the complex interactions in this important core complex and reveal the common property but discreet roles of the RIIa clan members.

Here we demonstrate that the Dpy-30 domain in Dpy-30 protein (Dpy-30 D/D) binds to an AH-like region near the C-terminus of human Ash2 (hAsh2). This AH binds poorly to RI's and RII's D/D domains (RIα D/D and RIIα DID), yet the mutation of a conserved charged residue in hAsh2's AH enables this fairly mono-specific AH to bind RIIα D/D as well. This finding explains the Y-shape morphology of the core complex and sheds light on a mechanism for curtailing cross reactivity of many D/D domains and AHs in eukaryotic cells and in practical applications.

Results

RIα DID or RIIα D/D binds to a helix that consists of four consecutive ΦΦXX repeats, in which the first two residues are hydrophobic residues (Φ); or often a hydrophobic residue is replaced by a polar, uncharged a.a. (Angelo and Rubin, 1998; Burns-Hamuro et al., 2003; Gold et al., 2006). The arrangement allows the formation of a hydrophobic patch at one side of the helix to associate with the hydrophobic pockets aligned into a diagonal groove on the dimeric D/D. It has been demonstrated that Dpy-30 binds to Ash2 at the C-terminus after the SPRY domain (South et al., 2010). The $10^{-7}$ M $K_d$ (Patel et al., 2009) is in line with that for most AHs and RIα D/D (Herberg et al., 2000; Burns-Hamuro et al., 2003; Means et al., 2011). We reasoned that if Ash2 C-terminal region binds the Dpy-30 domain, the binding site should be an α-helix with ΦΦXX-like repeats. Sequence analysis of this region from diverse organisms showed that they contain at least one α-helix (FIG. 10B, underlined). However, the hydrophobic residues (FIG. 10B, shaded in grey) are not exactly aligned with the ΦΦXX repeats and some of the motifs are not consecutive or aligned with the helix. In contrast, two acidic residues, E and D, are perfectly aligned. We hypothesized that the Dpy-30 domain binds to these helices.

To test this, we performed pull down assays for His-Dpy-30 and GST-hAsh2$_{593-623}$. The human Ash2 fragment contains a helix with two typical and three atypical ΦΦXX motifs. The hAsh2 DNA was fused downstream to GST DNA by PCR and the product was cloned into an expression vector. Three clones—#9 and #14 with the expected in-frame fusion and #6 with an out-of-frame fusion—were expressed in bacteria. Their extract was mixed with equal volume of bacterial extract with His-Dpy-30; and the mixture was subjected to Ni-NTA purification. As revealed by a Coomassie-stained SDS-PAGE gel, GST-hAsh2$_{593-623}$ from #9 and #14 (FIG. 11A, arrow) were co-purified with His-Dpy-30 (double arrowheads) in the eluate, whereas the incorrect fusion peptide from #6 clone was not co-purified. Thus hAsh2$_{593-623}$ interacts with Dpy-30 specifically.

To refine the boundary of the binding region, we modified the constructs to express four different mutated hAsh2 peptides (Table 3).

TABLE 3

| | | | |
|---|---|---|---|
| hAsh2$_{593-623}$ | PMSDMGWGAVVEHTLADVLYHVETEV DGRRS | + | (SEQ ID NO: 28) |
| hAsh2$_{593-617}$ | PMSDMGWGAVVEHTLADVLYHVETE* | + | (SEQ ID NO: 29) |
| W$_{500}$P | PMSDMGPGAVVEHTLADVLYHVETEV DGRRS | − | (SEQ ID NO: 30) |
| Δ$_{614-619}$ | PMSDMGWGAVVEHTLADVLYH----- -GRRS | − | (SEQ ID NO: 31) |
| Δ$_{610-619}$ | PMSDMGWGAVVEHTLAD--------- -GRRS | − | (SEQ ID NO: 32) |
| E$_{604}$K | PMSDMGWGAVVKHTLADVLYHVETEV DGRRS | + | (SEQ ID NO: 33) |

Table 3 illustrates the protein sequences of hAsh2's C-terminal region (hAsh2$_{593-623}$) and its variants, where "+" or "−" indicates if the peptides were or were not evidently co-purified with Dpy-30. The shorter fusion protein GST-hAsh2$_{593-617}$ that terminated right after the last possible ΦΦXX-like motif, VETE (SEQ ID NO:35), in the helix was also co-purified with His-Dpy-30 (FIG. 11B, arrow and double arrowheads), no matter expressed separately or co-expressed. Both polypeptides were depleted in the flow through of Ni-NTA matrix (Post in FIG. 11B) and retained in the eluate.

To differentiate if the interaction is via the Dpy-30 domain or the N-terminal fragment, His-Dpy-30 D/D (a.a. #49-99) was co-expressed with GST-hAsh2$_{593-623}$ (FIG. 11C). To define the N-terminal end of Dpy-30 D/D binding site in hAsh2, W$_{599}$ in the first potential ΦΦXX motif was mutated into P to disrupt helicity, an approach to abolish D/D-binding (Carr et al., 1982; Burns-Hamuro et al., 2003). Both GST-hAsh2$_{593-623}$ and its W$_{599}$P variant were still co-purified with the Dpy-30 domain (arrow and arrowhead in FIG.

11C). On the other hand, deleting VETEVD (SEQ ID NO:34) or one more adjacent motifs (Δ614-619 or Δ610-619) abolished the co-purification. Thus, the site that directly binds Dpy-30 D/D resides within hAsh2$_{600-617}$ that is after W$_{599}$ and contains four ΦΦXX-like motifs, even though an acidic residue occupies a supposedly hydrophobic position in the last motif, VETE (SEQ ID NO:35). The affinity may be further enhanced by adjacent sequences (Burns-Hamuro et al., 2003; Banky et al., 2003).

Most AHs are mono-specific to RIIα D/D except a few that are either RIα D/D-specific (Angelo and Rubin, 1998; Means et al., 2011; Welch et al., 2010) or dual specific, binding to both (Huang et al., 1997; Jarnaess et al., 2008). To test if hAsh2 AH can cross-react with PKA's D/D, we created constructs expressing the D/D domain and the flanking sequences from bovine RIα (a.a.#1-81) and mouse RIIα (a.a.#1-64). His-RIα D/D or His-RIIα D/D was co-expressed with GST-RSP3$_{96-180}$, which contains the AH (RSP3$_{160-178}$) that bind RII in the overlay assay (Gaillard et al., 2001). Their abundance in the extract were substantially reduced in the flow through following the incubation with the Ni-NTA matrix (FIG. 12A, left panel, compare Extract and Post), indicating their interactions in the bacterial extract. In the eluate, the ratio of RSP3$_{96-180}$-RIα D/D was the lowest, followed by RSP3$_{96-180}$-RIIα D/D and then RSP3$_{96-180}$-RIIα D/D from RSP7, the de facto partner of RSP3. Although RSP3$_{96-180}$ in the extract was also the most concentrated when co-expressed with RSP7's RIIα, this likely is due to effective binding of RSP7's D/D, protecting GST-RSP3$_{96-180}$ from proteolysis, which occurred when GST-RSP3$_{96-180}$ was expressed by itself (not shown). Similarly, when co-expressed with GST-hAsh2$_{593-623}$, RIα D/D and RIIα D/D were depleted in the flow through but few polypeptides, especially RIIα D/D, were present in the eluate (FIG. 12A, right panel, compare Extract, Post and Elute).

Figure 12:
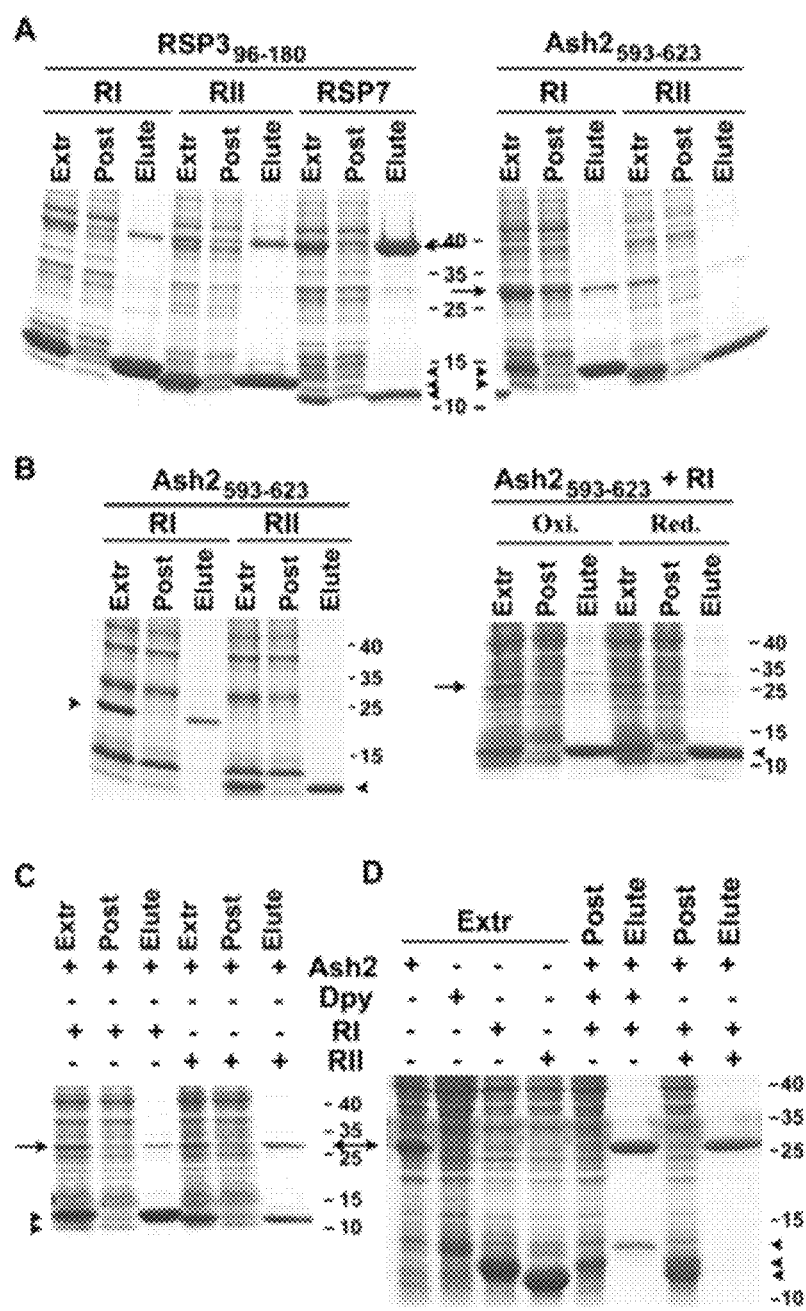
FIG. 12. GST-$hAsh2_{593-623}$ has lower affinity for RIα D/D or RIIα D/D. (A) As a control, the co-purification of RIIα-like D/D domain with the amphipathic helix in the radial spoke GST-$RSP3_{90-180}$ is the most efficient for its de-facto partner, RSP7's RIIα domain, followed by RIIα and RIα (left panel). A small fraction of RIα was co-purified with GST-$hAsh2_{593-623}$, whereas the co-purification of RIIα domain was negligible. Notably, both RIα D/D and RIIα D/D appeared depleted in the flow through (post). (B) In non-reducing SDS-PAGE gel, RIα D/D, which could form inter-monomer disulfide bonds, migrated as a homodimer, contrary to monomeric RIIα D/D. However, addition of 5 mM b-mercaptoethanol did not change the outcome significantly. (C) Reduction of [NaCl] from 300 mM to 100 mM resulted in more co-purification of RIIα D/D, but not RIα D/D, with GST-hAsh2$_{593-623}$. (D) Glutathione affinity purification of GST-hAsh2$_{593-623}$ from the bacterial mixtures which contained two D/D domains, only co-purified the Dpy-30 domain, despite excessive amounts of RIα and RIIα. The samples were fractionated by SDS-PAGE and revealed by Coomassie stain.

Although both RIα D/D and Dpy-30 D/D have a common α0 helix (Wang et al., 2009), GST-hAsh2$_{593-623}$ cross reacted with RIα D/D poorly. We wondered if this was due to disulfide bonds via the conserved cysteine residues in RIα D/D in oxidative states. To test this, the samples from repeated experiments were analyzed in the non-reducing SDS-PAGE. As shown by the Coomassie-stained gel, RIα D/D indeed migrated as a dimer whereas RIIα D/D, which does not have cysteines, migrated as a monomer (FIG. 12B, compare arrowheads). To test if the presence of a reducing agent would improve the association, Ni-NTA pulldown was conducted in the presence of 5 mM β-mercaptoethanol. RIα D/D was pull down equally by Ni-NTA in both conditions, but the reducing agent did not increase the pulldown of GST-hAsh2$_{593-623}$.

To test if the 300 mM NaCl in all buffers for Ni-NTA affinity purification dissociated the cross-recognition, the NaCl concentration was decreased to 100 mM. The lower salt condition did enhance the co-purification of GST-hAsh2$_{593-623}$ with RIIα D/D but not RIα D/D (FIG. 12C). This suggests that electrostatic interaction accounts for the weak RIIα D/D-hAsh2$_{593-623}$ cross recognition, whereas the RIα D/D-hAsh2$_{593-623}$ association may rely on the other types of attractions. To directly compare the association, all fusion proteins were expressed separately, and equal volume of the extracts containing RIα D/D, Dpy-30 D/D, and GST-hAsh2$_{593-623}$ were mixed together and then with Glutathione Sepharose. A parallel experiment was conducted with RIα D/D, RIIα D/D and GST-hAsh2$_{593-623}$. As shown in the eluate, only Dpy-30 domain was obviously pulled down with GST-hAsh2$_{593-623}$ (FIGS. 12C and 12D). Taken together, these data show different interactions involved between D/Ds and AHs; and the interactions between the de facto partners, RSP7 D/D-RSP3 or Dpy-30 D/D-hAsh2, are the strongest.

Figure 10:
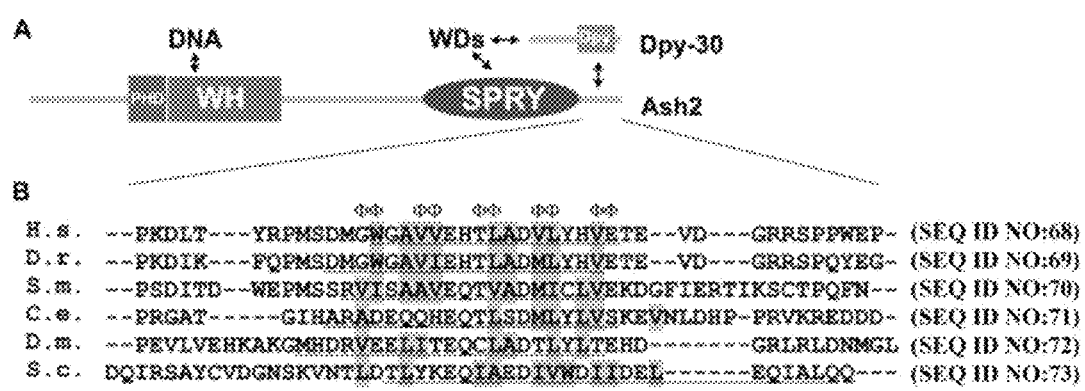
FIG. 10. Analysis of Dpy-30-binding sequence at the C-terminus of Ash2. (A) The schematic depicting the molecular modules in the 99-a.a. Dpy-30 and the 628-a.a. Ash2 from human. Ash2 has two major domain—PHD-WH, that binds DNA; and SPRY, which associates with WD-repeat proteins. The sequence downstream to the SPRY domain binds Dpy-30, which contains only the Dpy-30 domain. Dpy-30 also interacts with WD-repeat proteins. The molecular modules, based on crystal structures, are depicted in proportion to their sizes. Double-headed arrows indicate molecular interactions. (B) The sequences at the Dpy-30-binding region in Ash2-like proteins diverge but all contain an α-helix of varying length (underlined). The position of hydrophobic residues (shaded in grey) in the helices are not consistently positioned like those in a typical RIIα-binding AH, four consecutive repeats with paired hydrophobic residues (Φ) present in every four a.a. The multiple sequence alignment was generated by ClustalW2. Consensus secondary structure predictions were generated based on the combined results of the default methods (MLRC, DSC and PHD) in Pole Bioinformatique Lyonnais. H.s., *Homo sapiens*; D.r., *Danio rerio*; S.m., *Schistosoma mansoni*; C.e., *Caenorhabditis elegans*; D.m., *Drosophila melanogaster*; S.c., *Saccharomyces cerevisiea*.

Mutation and peptide arrays demonstrated that changes in a.a. within and around AHs could affect their affinity and specificity for D/Ds (Burns-Hamuro et al., 2003). To learn what it takes to turn GST-hAsh2$_{593-623}$ into an RIα- or RIIα-binding helix, we mutated E$_{604}$ in the first 4-a.a. motif, VVEH (SEQ ID NO:36), to K. This residue appears to be conserved among Ash2 from human to yeast (FIG. 10). As shown in the eluate, the E$_{604}$K mutation substantially enhanced the pulldown of RIIα D/D but not RIα D/D (FIG. 13, left panel), but the mutated GST-hAsh2$_{593-623}$ was still pulled down substantially with the full-length Dpy-30 (FIG. 13, right panel). In this experiment, over expressed Dpy-30 D/Ds form stable oligomers even in the presence of SDS-containing sample buffer (Dong et al., 2005).

Discussion

The Dpy-30 Domain Binds to an Amphipathic Helix Near the C-Terminus of hAsh2.

Figure 11:
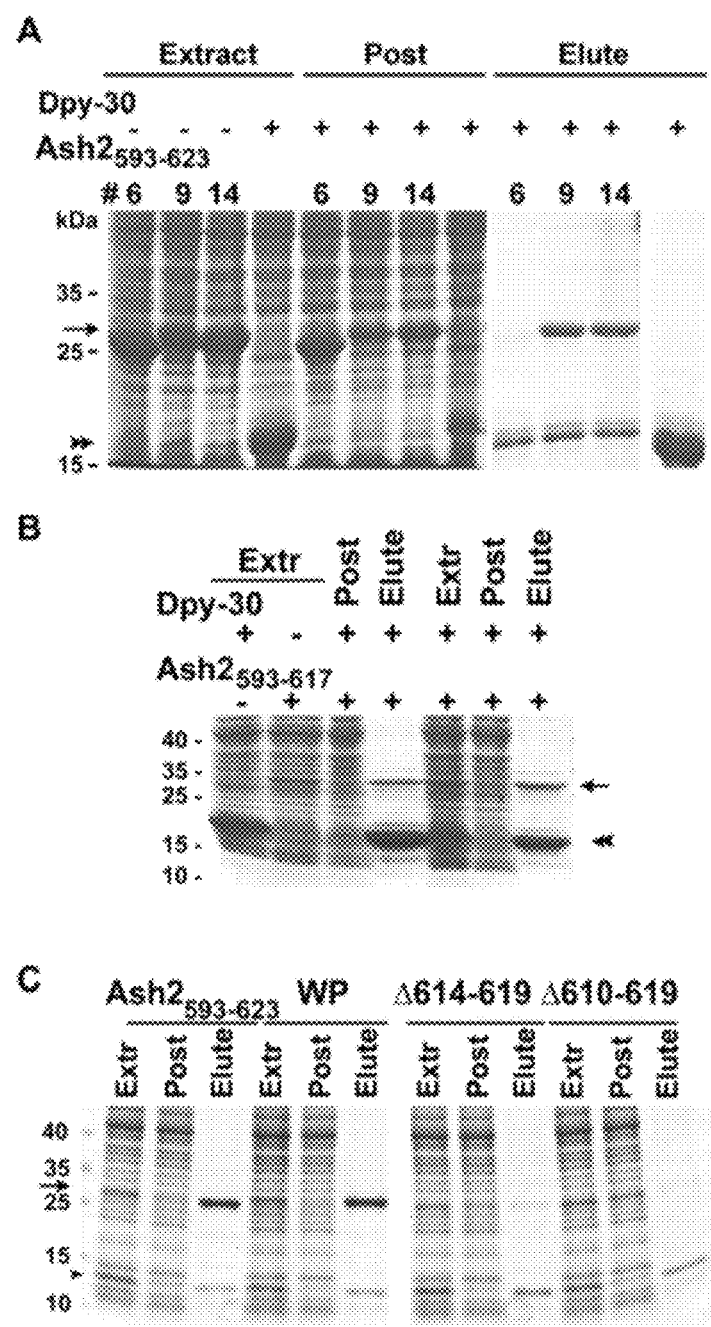
FIG. 11. The region near $hAsh2_{600-617}$ binds the Dpy-30 domain. (A) The in-frame GST-$hAsh2_{593-623}$ fusion protein from #9 and #14 clones (arrow) bind to His-Dpy-30 (double arrowhead) as shown by Ni-NTA pull down. As a control, the out-of-frame, slightly shorter, fusion polypeptide from the #6 clone cannot. The extract (Extr), flow through (Post) and eluate (Elute) were fractionated by SDS-PAGE and revealed by the Coomassie Blue stain. (B) The interaction of Dpy-30 and GST-$hAsh2_{593-617}$ that terminates after the possible motif, VETE. They were co-expressed or expressed separately in bacteria. For the latter, an equal volume of the extracts from one GST-tag clone and the Dpy-30 clone were mixed together first. The extracts containing both fusion polypeptides were subjected to Ni-NTA pulldown. (C) The interaction was not affected by the replacement of $W_{599}$ in GST-$hAsh2_{593-623}$ with P($W_{599}$P), but largely abolished by the deletion of a.a. at #614-619 or #610-619. The Dpy-30 domain used in crystallography ($Dpy-30_{49-99}$, arrowhead) was used in this experiment.

Founded on the previous discovery that Dpy-30 protein binds to the region downstream to the SPRY domain in Ash2, the in vitro co-purification experiments further refined the mechanism via Dpy-30 D/D and a helix with four consecutive typical and atypical ΦΦXX motifs (FIG. 10B), like the AHs that bind RIα D/D, RIIα D/D, and Dpy-30 D/D in the radial spoke. The gross similarity in secondary and tertiary structures, among D/Ds and among AHs, is reflected in the depletion of GST-hAsh2 in the flow through following pulldown of His-RIα D/D or His-RIIα D/D by Ni-NTA (FIG. 12A). However, the mismatched association is not substantial enough to retain most hAsh2 in the eluate, compared to the co-purification hAsh2 with its genuine partner, His-Dpy-30 (FIG. 11). Likewise, only His-Dpy-30 D/D was visibly pulled down with GST-hAsh2 by glutathione affinity (FIG. 12D). Thus hAsh2 uses the same principle that AKAPs employ to anchor RIα D/D and RIIα D/D for binding Dpy-30 D/D selectively. The consecutive repeats are also evident in the helical region in yeast Ash2 (Bre2) (FIG. 14A), although the motif-containing sequences do not align precisely by multiple sequence alignment (FIG. 14B). Perhaps the motifs, instead of the primary sequences, are conserved for D/D-AH interactions.

Unique Features in the Dpy-30 Domain and Ash2's AH.

The surface topography and chemical property of D/D and AHs are distinct enough to determine the affinity and specificity for most D/Ds and AHs (Burns-Hamuro et al., 2003; Gold et al., 2006; Kinderman et al., 2006; Sarma et al., 2010), with the exception of RIα D/D-AH interactions that also involve a flanking loop (Angelo and Rubin, 1998; Jarnaess et al., 2008; Means et al., 2011). This appears to be true for Ash2/Dpy-30 as well, but with an unexpected mechanism and versatility. RIIα has a flexible N-terminal β-strand, which could bend toward AHs, enabling tight hydrophobic interactions of the conserved isoleucines, Is, (FIG. 14A) with the residues in the first two ΦΦXX motifs (Kinderman et al., 2006; Sarma et al., 2010). Consequentially, the third and fourth ΦΦXX motifs are less significant in D/D-AH interaction. Contrary to the flexible RIIα D/D's β-strand, both RIα D/D and Dpy-30 D/D have an α0 helix (Wang et al., 2009). But this similarity does not lead to significant cross recognition of RIα D/D with hAsh2, regardless of redox conditions or salt concentrations (FIG. 12A-12C). This may be related to unique features of Ash2 and Dpy-30. Contrary to the highly hydrophobic surface of RIα D/D and RIIα D/D, the surface of Dpy-30 D/D is much more hydrophilic, primarily due to a positively charged R in the α0 helix (FIG. 14B, double arrowhead) (Wang et al., 2009), adjacent to the YL residues (residues shaded in grey) typical for all Dpy-30 domains. The long positive side chains of the R residues from two protomers flank both ends of the hydrophobic groove. One of them may explain the unusual acidic $E_{615}$ in the $2^{nd}$ hydrophobic position of the last motif, VETE (FIG. 14A, arrowhead) and the decisive impact of this seemingly degenerate motif in the Dpy-30/Ash2 interaction (FIGS. 11B and 11C). $E_{615}$, equivalent to the hydrophobic M in the last motif of D-AKAP2 (arrowhead in FIGS. 14A and 14C upper panel), will present a negative side chain toward the positive side chain of the R in one protomer (double arrowhead in FIG. 14B). Perhaps the salt bridge and/or hydrogen bond through these charged polar residues near the end of the AH and the α0 helix are crucial for their association, lessening the reliance on the hydrophobic interactions through the first two ΦΦXX motifs, which are not apparent in some Ash2-like molecules (FIG. 14A).

In contrast, $E_{604}$ in hAsh2's first ΦΦXX motif, VVEH (SEQ ID NO:36) (FIG. 14A, arrow), seems strictly conserved for a different reason. Based on the tertiary structure, this E corresponds to the bulky W in D-AKAP2 (data not shown), that could be replaced by a number of different a.a. residues without deleterious effects on RIα binding (Banky et al., 2003; Sarma et al., 2010). Likewise, $E_{604}K$ mutation does not affect hAsh2's binding with Dpy-30 D/D. However, the change is sufficient to allow the mutated hAsh2 to be pull down with RIIα D/D, converting the monospecific AH into a dual specific AH. The positive-charge side chain may foster new bond formation with RIIα D/D, elevating the poor affinity from the cross recognition. Alternatively, this mutated dual specific AH, when binding to RIIα, may shift forward an entire helical turn as D-AKAP2, which binds RIα and RIIα starting with #1 and #2 ΦΦXX motifs respectively (Sarma et al., 2010; Kinderman et al., 2006). Regardless, the increased cross recognition raises a possibility that this E residue is conserved to prevent cross-recognition of Ash2 with PKA, rather than to enhance the association of Ash2 and Dpy-30.

Curiously, these charged R and E residues are not present in the Dpy-30 domain and their complementary AHs in the radial spoke proteins; or in the putative AH in BIG1, a nucleotide exchange factor in the trans-Golgi network (FIG. 14) (Xia et al., 2010). In fact, AHs from RSP3 and BIG1 are comprised of four typical ΦΦXX motifs. Perhaps the interaction of Dpy-30 D/D with AHs in RSP3 and BIG1 relies more on hydrophobic interaction than with Ash2's AH. The significance of the subtle differences is also reflected in the co-purification with the RIIα D/D-binding RSP3 AH (FIG. 12A). Although this AH binds RIIα in the overlay assay (Gaillard et al., 2001), its co-purification with its de facto partner, RSP7's D/D, is much better than with RIIα D/D or RIα (FIG. 12A). These results strongly suggest that the sequences of de facto partners co-evolved to ensure specificity. Extensive evidence have showed that high affinity AHs for RIα D/D or RIIα D/D could displace PKA (for example, Carr et al., 1992; Alto et al., 2003; Burns-Hamuro et al., 2003; Carlson et al., 2006). Perhaps Dpy-30-selective AHs could also be used to perturb H3K4 methylation by Set/MLL/Compass-like methyltransferases. On the other hand, it is imperative to verify cross recognitions of blocking peptides.

The D/D Domain—a Tool to Form Symmetric Module?

While PKA holoenzyme may form a symmetric complex due to the D/D domain, a symmetry conformation may not be relevant to its function, as the holoenzyme actually is inactive and catalytic subunits function as monomers after dissociating from RI or RII when the cAMP concentration increases (Beavo et al., 2002). However, the similarities between the Compass core complex and the radial spoke, suggest that D/D domains may be one of the eukaryotic strategies to form perfect or imperfect symmetric functional modules. High-resolution electron microscopy revealed that both complexes are Y-shape particles, with Dpy-30-domain-containing proteins situated near the bifurcation (Takahashi et al., 2011; Pigino et al., 2011; Barbar et al., 2012). This similar conformation could be explained by a model of a two-prong structural linker. For example, the dimeric D/D from RSP2 docks to an AH in RSP3, the scaffold in the radial spoke (Sivadas et al, unpublished), whereas its flanking C-terminal helices may form coiled coils with the two spokehead paralogues (RSP4 and RSP6) (Yang et al., 2006; Kohno et al., 2011). Likewise, in the Compass, Dpy-30's D/D dimer interacts with Ash2's C-terminal AH, while the two flanking N-terminal fragments may harness the two WD-repeat subunits (RbBP5 and WDR5). The two distinct polypeptides with identical molecular modules, one more critical than the other, could introduce subtle asymmetry (Southall et al., 2009; Takahashi, et al., 2011; Barber et al., 2011). As such, only one side of the core complex further associate with a Set1 domain into a particular conformation necessary for H3K4 tri-methylation, which is conferred by Dpy-30 and Ash2 (Takahashi et al., 2011; Jiang et al, 2011; Dou et al., 2006; Steward et al., 2006).

Materials and Methods

Construct Design.

PCR was used to amplify DNA fragments for protein coding sequences with the primer pairs listed below. Primers are named after the recombinant polypeptides with an additional S or AS to depict the sense or anti-sense direction. The built-in restriction sites for cloning purposes are underlined; the nucleotides for mutagenesis are in bold letters; the space within primers indicates the junction of two separated DNA sequences.

DPY30S:
(SEQ ID NO: 37)
CC<u>CATATG</u>GAGCCAGAGCAGATGCTGGAG

DPY30AS:
(SEQ ID NO: 38)
GC<u>CTCGAG</u>TCAGITTCGATC TTCAAACTGTGCC

DPY$_{49-99}$S:
(SEQ ID NO: 39)
G<u>CTGCAG</u>AAGGTAGATCTCCAGTCTTTGCCAAC

DPY$_{49-99}$AS:
(SEQ ID NO: 40)
GG<u>CTAGC</u>TCAGMCGATCTTCAAACTGTCC

RIIαS:
(SEQ ID NO: 41)
AC<u>CATATG</u>GGCCACATCCAGATCCCGC

RIIαAS:
(SEQ ID NO: 42)
AC<u>CTCGAG</u>CTAGCTGGACTCCTGCGTGTGAAAGGTCG

RIαS:
(SEQ ID NO: 43)
AC<u>CATATG</u>GCTTCCGGCACCACCGC

RIαAS:
(SEQ ID NO: 44)
AC<u>CTCGAG</u>CTATTCATCCTCCCGAGAGTCTGCACG

-continued

GSTS:
(SEQ ID NO: 45)
GCCCATGGAGTCCCCTATACTAGGTTATTGG

GSTAS:
(SEQ ID NO: 46)
GGGGGATCCACGCGGAACCAGATCCG

GSThAsh2fuseS:
(SEQ ID NO: 47)
CTGGTTCCGCGTGGATCCCCC_CCTATGAGTGACATGGGCTGG

HAsh2$_{593-623}$AS:
(SEQ ID NO: 48)
AATGCATTCAACTGCGCCTCCCATCCACTTC

HASH2$_{593-617}$S:
(SEQ ID NO: 49)
GTATCACGTGGAGACAGAATAAGATGGGAGG

W*PS:
(SEQ ID NO: 50)
CCTATGAGTGACATGGGCCCGGGCGCCGTGGTAGAGC

W*PAS:
(SEQ ID NO: 51)
GGATACTCACTGTACCCGGGCCCGCGG

E$_{604}$KS:
(SEQ ID NO: 52)
GCGCCGTGGTAAAGCACACCCTGGCTGACG

Δ$_{614-619}$ S:
(SEQ ID NO: 53)
CTGGCTGACGTCTTGTATCAC_GGGAGGCGCAGTTGAATGCAGG

Δ$_{610-619}$ S:
(SEQ ID NO: 54)
GGTAGAGCACACCCTGGCTGACG_GGAGGCGCAGTTGAATGC

Uni-GSThAsh2AS:
(SEQ ID NO: 55)
GCCCATGTCACTCATAGG

Briefly, Dpy-30 fragments, full length or a.a.#49-99, were amplified using purchased IMAGE cDNA clone #4081996 as a template. The two PCR products were respectively cloned into pET28(a) vector between the sites of Nde and Xho; and into pET28-H8-TEV vector between the sites of Pst and Nhe. Bovine RIα and mouse RIIα DNA fragments encoding the D/D domains and short flanking sequences were amplified using the full-length templates pRSETB-RIα and pRSETB-RIIα kindly provided by Dr. Susan Taylor at University of California, San Diego and the PCR products were cloned into pET28(a) vector between the sites of Nde and Xho. The constructs will express RIα's N-terminal 81-a.a. and RIIα's N-terminal 64 a.a. Both fragments include an RIIa domain and a short flanking sequence (Newlon et al., 2001; Banky et al., 2003). The pGST-hAsh2 construct expressing GST-hAsh2's AH was generated by first PCR-amplifying DNA fragments encoding GST and the hAsh2 peptide respectively from pGEX-2T vector and a purchased human Ash2 (hAsh2) IMAGE cDNA clone #3921999. Both fragments were fused together by re-PCR with three primers—GSTS, GSThAsh2fuseS and HAsh2$_{593-623}$AS. The fused DNA fragment was inserted between the Nco and Pst site in pET-Duet vectors. The GST-RSP3 construct was generated similarly (Sivadas et al., unpublished). The pGST-hAsh2 plasmid was used as a template for creating mutated hAsh2 constructs by site-directed mutagenesis using the QuikChange strategy (Stratagene) except that primer pair sequences were overlapped only partially or not at all. All clones were sequenced to confirm sequence accuracy.

In-Vitro Binding Analysis.

All expression constructs were transformed or co-transformed into BL21(DE3) cells. The colonies were selected based on the antibiotic-resistant gene in each plasmid. The cultures were induced with 1 mM IPTG overnight at 18° C. The cell pellet from a 5-ml culture was resuspended in 750-μl lysis buffer supplemented with Complete Mini EDTA-free protease inhibitor cocktail tablets (Roche) and the suspension was sonicated on ice using Branson digital Sonifier until clarified (Emerson Industrial Automation). The sonicated mixtures were centrifuged at 4° C., 12,000 rpm for 25 min. The supernatant or combinations of supernatants as indicated were incubated with ~100 μl Ni-NTA (Qiagen or Clontech) or Glutathione Sepharose 4B (Amersham Biosciences) for 1 hour at room temperature. The matrix was subsequently washed as instructed by manufacturers, unless indicated otherwise. The matrix was then treated with 75-μl elution buffer alone or the elution buffer in 2× Laemmli SDS-PAGE sample buffer for more effective elution.

SDS-PAGE.

Bacterial extract, flow through and eluate in 1× Laemmli samples buffer were boiled for 5 min. In general, 10 μl samples were loaded in each lane in 4-20% precast acrylamide gels (Bio-Rad or DGEL Electrosystem, Canada) or 14% manually cast gels.

Sequence Analysis.

Protein secondary structure was analyzed using the program in Pôle Bioinformatique Lyonnais. The crystal structures were generated using the Cn3D program available through National Center for Biotechnology Information.

REFERENCES

Alto, N. M., S. H. Soderling, N. Hoshi, L. K. Langeberg, R. Fayos, P. A. Jennings, and J. D. Scott. 2003. Bioinformatic design of A-kinase anchoring protein-in silico: a potent and selective peptide antagonist of type II protein kinase A anchoring. Proc Natl Acad Sci USA. 100:4445-50.

Angelo, R., and C. S. Rubin. 1998. Molecular characterization of an anchor protein (AKAPCE) that binds the RI subunit (RCE) of type I protein kinase A from Caenorhabditis elegans. J Biol Chem. 273:14633-43.

Avdic, V., P. Zhang, S. Lanouette, A. Groulx, V. Tremblay, J. Brunzelle, and J. F. Couture. 2011. Structural and biochemical insights into MLL1 core complex assembly. Structure. 19:101-8.

Banky, P., M. Roy, M. G. Newlon, D. Morikis, N. M. Haste, S. S. Taylor, and P. A. Jennings. 2003. Related protein-protein interaction modules present drastically different surface topographies despite a conserved helical platform. J Mol Biol. 330:1117-29.

Barber C. F., T. Heuser, B. I. Carbajal-González, V. V. Jr. Botchkarev, and D. Nicastro. 2012. Three-dimensional structure of the radial spokes reveals heterogeneity and interactions with dyneins in Chlamydomonas flagella. Mol Biol Cell. 23:111-20.

Beavo, J. A., and L. L. Brunton. 2002. Cyclic nucleotide research—still expanding after half a century. Nat Rev Mol Cell Biol. 3:710-8.

Brokaw, C. J., 1987. Regulation of sperm flagellar motility by calcium and cAMP-dependent phosphorylation. J Cell Biochem. 35(3):175-84.

Burns-Hamuro, L. L., Y. Ma, S. Kammerer, U. Reineke, C. Self, C. Cook, G. L. Olson, C. R. Cantor, A. Braun, and S. S. Taylor. 2003. Designing isoform-specific peptide disruptors of protein kinase A localization. Proc Natl Acad Sci USA. 100:4072-7.

Cao, F., Y. Chen, T. Cierpicki, Y. Liu, V. Basrur, M. Lei, and Y. Dou. 2010. An Ash2L/RbBP5 heterodimer stimulates the MLL1 methyltransferase activity through coordinated substrate interactions with the MLL1 SET domain. PLoS One. 5:e14102.

Carlson, C. R., B. Lygren, T. Berge, N. Hoshi, W. Wong, K. Tasken, and J. D. Scott. 2006. Delineation of type I protein kinase A-selective signaling events using an RI anchoring disruptor. J Biol Chem. 281:21535-45.

Carr, D. W., A. Fujita, C. L. Stentz, G. A. Liberty, G. E. Olson, and S. Narumiya. 2001. Identification of sperm-specific proteins that interact with A-kinase anchoring proteins in a manner similar to the type II regulatory subunit of PKA. J Biol Chem. 276:17332-8.

Carr, D. W., Z. E. Hausken, I. D. Fraser, R. E. Stofko-Hahn, and J. D. Scott. 1992. Association of the type II cAMP-dependent protein kinase with a human thyroid RII-anchoring protein. Cloning and characterization of the RII-binding domain. J Biol Chem. 267:13376-82.

Carr, D. W., R. E. Stofko-Hahn, I. D. Fraser, S. M. Bishop, T. S. Acott, R. G. Brennan, J. D. Scott. 1991. Interaction of the regulatory subunit (RII) of c-AMP dependent protein kinase with RII-anchoring proteins occurs through an amphipathic helix binding motif. J Biol Chem. 266(22):14188-92.

Chen, Y., F. Cao, B. Wan, Y. Dou, and M. Lei. Structure of the SPRY domain of human Ash2L and its interactions with RbBP5 and DPY30. Cell Res. 22:598-602.

Chen, Y., B. Wan, K. C. Wang, F. Cao, Y. Yang, A. Protacio, Y. Dou, H. Y. Chang, and M. Lei. 2011. Crystal structure of the N-terminal region of human Ash2L shows a winged-helix motif involved in DNA binding. EMBO Rep. 12:797-803.

Cho, Y. W., T. Hong, S. Hong, H. Guo, H. Yu, D. Kim, T. Guszczynski, G. R. Dressier, T. D. Copeland, M. Kalkum, and K. Ge. 2007. PTIP associates with MLL3- and MLL4-containing histone H3 lysine 4 methyltransferase complex. J Biol Chem. 282:20395-406.

Diener, D. R., L. H. Ang, and J. L. Rosenbaum. 1993. Assembly of flagellar radial spoke proteins in *Chlamydomonas*: identification of the axoneme binding domain of radial spoke protein 3. J Cell Biol. 123:183-90.

Diener, D. R., P. Yang, S. Geimer, D. G. Cole, W. S. Sale, J. L. Rosenbaum. 2011. Sequential assembly of flagellar radial spokes. Cytoskeleton. 68(7):389-400.

Dong, X., Y. Peng, Y. Peng, F. Xu, X. He, F. Wang, X. Peng, B. Qiang, J. Yuan, and Z. Rao. 2005. Characterization and crystallization of human DPY-30-like protein, an essential component of dosage compensation complex. Biochim Biophys Acta. 1753:257-62.

Dou, Y., T. A. Milne, A. J. Ruthenburg, S. Lee, J. W. Lee, G. L. Verdine, C. D. Allis and R. G. Roeder. 2006. Regulation of MLL1 H3K4 methyltransferase activity by its core components. Nat Struct Mol Biol. 3(8):713-9.

Fujita, A., K. Nakamura, T. Kato, N. Watanabe, T. Ishizaki, K. Kimura, A. Mizoguchi, and S. Narumiya. 2000. Ropporin, a sperm specific binding protein of rhophilin that is localized in the fibrous sheath of sperm flagella. J Cell Sci. 113(Pt1):103-12.

Gaillard, A. R., D. R. Diener, J. L. Rosenbaum, and W. S. Sale. 2001. Flagellar radial spoke protein 3 is an A-kinase anchoring protein (AKAP). J Cell Biol. 153:443-8.

Gaillard, A. R., L. A. Fox, J. M. Rhea, B. Craige, and W. S. Sale. 2006. Disruption of the A-kinase anchoring domain in flagellar radial spoke protein 3 results in unregulated axonemal cAMP-dependent protein kinase activity and abnormal flagellar motility. Mol Biol Cell. 17:2626-35.

Gold, M. G., B. Lygren, P. Dokurno, N. Hoshi, G. McConnachie, K. Tasken, C. R. Carlson, J. D. Scott, and D. Barford. 2006. Molecular basis of AKAP specificity for PKA regulatory subunits. Mol Cell. 24:383-95.

Greengard, P., J. Jen, A. C. Nairn, and C. F. Stevens. 1991. Enhancement of the glutamate response by cAMP-dependent protein kinase in hippocampal neurons. Science. 253:1135-8.

Habermacher, G., and W. S. Sale. 1996. Regulation of flagellar dynein by an axonemal type-1 phosphatase in *Chlamydomonas*. J Cell Sci. 109(Pt 7):1899-907.

Habermacher, G., and W. S. Sale. 1997. Regulation of flagellar dynein by phosphorylation of a 138-kD inner arm dynein intermediate chain. J Cell Biol. 136:167-76.

Herberg, F. W., A. Maleszka, T. Eide, L. Vossebein, and K. Tasken. 2000. Analysis of A-kinase anchoring protein (AKAP) interaction with protein kinase A (PKA) regulatory subunits: PKA isoform specificity in AKAP binding. J Mol Biol. 298:329-39.

Hirsch, A. H., S. B. Glantz, Y. Li, Y. You, and C. S. Rubin. 1992. Cloning and expression of an intron-less gene for AKAP 75, an anchor protein for the regulatory subunit of cAMP-dependent protein kinase II beta. J Biol Chem. 267:2131-4.

Howard, D. R., G. Habermacher, D. B. Glass, E. F. Smith, and W. S. Sale. 1994. Regulation of *Chlamydomonas* flagellar dynein by an axonemal protein kinase. J Cell Biol. 127:1683-92.

Hsu, D. R., and B. J. Meyer. 1994. The dpy-30 gene encodes an essential component of the *Caenorhabditis elegans* dosage compensation machinery. Genetics. 137:999-1018.

Huang, B., G. Piperno, Z. Ramanis, and D. J. Luck. 1981. Radial spokes of *Chlamydomonas* flagella: genetic analysis of assembly and function. J Cell Biol. 88:80-8.

Huang, L. J., K. Durick, J. A. Weiner, J. Chun, and S. S. Taylor. 1997. D-AKAP2, a novel protein kinase A anchoring protein with a putative RGS domain. Proc Natl Acad Sci USA. 94:11184-9.

Huang, L. J., K. Durick, J. A. Weiner, J. Chun, and S. S. Taylor. 1997. Identification of a novel protein kinase A anchoring protein that binds both type I and type II regulatory subunits. J Biol Chem. 272:8057-64.

Jarnaess, E., A. Ruppelt, A. J. Stokka, B. Lygren, J. D. Scott, and K. Tasken. 2008. Dual specificity A-kinase anchoring proteins (AKAPs) contain an additional binding region that enhances targeting of protein kinase A type I. J Biol Chem. 283:33708-18.

Jiang, H., A. Shukla, X. Wang, W. Y. Chen, B. E. Bernstein, and R. G. Roeder. 2011. Role for Dpy-30 in ES cell-fate specification by regulation of H3K4 methylation within bivalent domains. Cell. 144:513-25.

Kammerer, S., L. L. Burns-Hamuro, Y. Ma, S. C. Hamon, J. M. Canaves, M. M. Shi, M. R. Nelson, C. F. Sing, C. R. Cantor, S. S. Taylor, and A. Braun. 2003. Amino acid variant in the kinase binding domain of dual-specific A kinase-anchoring protein 2: a disease susceptibility polymorphism. Proc Natl Acad Sci USA. 100:4066-71.

Kinderman, F. S., C. Kim, S. von Daake, Y. Ma, B. Q. Pham, G. Spraggon, N. H. Xuong, P. A. Jennings, and S. S. Taylor. 2006. A dynamic mechanism for AKAP binding to RII isoforms of cAMP-dependent protein kinase. Mol Cell. 24:397-408.

Kindle, K. L. 1990. High-frequency nuclear transformation of *Chlamydomonas reinhardtii*. Proc Natl Acad Sci USA. 87:1228-32.

Klauck, T. M., M. C. Faux, K. Labudda, L. K. Langeberg, S. Jaken, and J. D. Scott. 1996. Coordination of three signaling enzymes by AKAP79, a mammalian scaffold protein. Science. 271:1589-92.

Kohno, T., K. Wakabayashi, D. R. Diener, J. L. Rosenbaum, and R. Kamiya. 2011. Subunit interactions within the *Chlamydomonas* flagellar spokehead. Cytoskeleton (Hoboken). 68:237-46.

Li, H., R. Adamik, G. Pacheco-Rodriguez, J. Moss, and M. Vaughan. 2003. Protein kinase A-anchoring (AKAP) domains in brefeldin A-inhibited guanine nucleotide-exchange protein 2 (BIG2). Proc Natl Acad Sci USA. 100:1627-32.

Lindemann, C. B. 2007. The geometric clutch as a working hypothesis for future research on cilia and flagella. Ann N Y Acad Sci. 1101:477-93.

Mak, A. B., Z. Ni, J. A. Hewel, G. I. Chen, G. Zhong, K. Karamboulas, K. Blakely, S. Smiley, E. Marcon, D. Roudeva, J. Li, J. B. Olsen, C. Wan, T. Punna, R. Isserlin, S. Chetyrkin, A. C. Gingras, A. Emili, J. Greenblatt, and J. Moffat. A lentiviral functional proteomics approach identifies chromatin remodeling complexes important for the induction of pluripotency. Mol Cell Proteomics. 9:811-23.

Mastronarde, D. N., E. T. O'Toole, K. L. McDonald, J. R. McIntosh, and M. E. Porter. 1992. Arrangement of inner dynein arms in wild-type and mutant flagella of *Chlamydomonas*. J Cell Biol. 118:1145-62.

Mauban, J. R., M. O'Donnell, S. Warrier, S. Manni, and M. Bond. 2009. AKAP-scaffolding proteins and regulation of cardiac physiology. Physiology (Bethesda). 24:78-87.

Means C. K., B. Lygren, L. K. Langeberg, A. Jain, R. E. Dixon, A. L. Vega, M. G. Gold, S. Petrosyan, S. S. Taylor, A. N. Murphy, T. Ha, L. F. Santana, K. Tasken, J. D. Scott. 2011. An entirely specific type I A-kinase anchoring protein that can sequester two molecules of protein kinase A at mitochondria. Proc Natl Acad Sci USA. 108(48): E1227-35.

Mohan, M., C. Lin, E. Guest, and A. Shilatifard. Licensed to elongate: a molecular mechanism for MLL-based leukaemogenesis. Nat Rev Cancer. 10:721-8.

Newell, A. E., S. E. Fiedler, J. M. Ruan, J. Pan, P. J. Wang, J. Deininger, C. L. Corless, and D. W. Carr. 2008. Protein kinase A RII-like (R2D2) proteins exhibit differential localization and AKAP interaction. Cell Motil Cytoskeleton. 65:539-52.

Newlon, M. G., M. Roy, D. Morikis, D. W. Carr, R. Westphal, J. D. Scott, and P. A. Jennings. 2001. A novel mechanism of PKA anchoring revealed by solution structures of anchoring complexes. Embo J. 20:1651-62.

Nicastro, D., J. R. McIntosh, and W. Baumeister. 2005. 3D structure of eukaryotic flagella in a quiescent state revealed by cryo-electron tomography. Proc Natl Acad Sci USA. 102:15889-94.

Nicastro, D., C. Schwartz, J. Pierson, R. Gaudette, M. E. Porter, and J. R. McIntosh. 2006. The molecular architecture of axonemes revealed by cryoelectron tomography. Science. 313:944-8.

Omoto, C. K., I. R. Gibbons, R. Kamiya, C. Shingyoji, K. Takahashi, and G. B. Witman. 1999. Rotation of the central pair microtubules in eukaryotic flagella. Mol Biol Cell. 10:1-4.

Patel, A., V. Dharmarajan, V. E. Vought, and M. S. Cosgrove. 2009. On the mechanism of multiple lysine methylation by the human mixed lineage leukemia protein-1 (MLL1) core complex. J Biol Chem. 284:24242-56.

Patel-King, R. S., O. Gorbatyuk, S. Takebe, and S. M. King. 2004. Flagellar radial spokes contain a Ca2+-stimulated nucleoside diphosphate kinase. Mol Biol Cell. 15:3891-902.

Pauling, L., R. B. Corey, and H. R. Branson. 1951. The structure of proteins; two hydrogen-bonded helical configurations of the polypeptide chain. Proc Natl Acad Sci USA. 37:205-11.

Pferdehirt, R. R., W. S. Kruesi, and B. J. Meyer. An MLL/COMPASS subunit functions in the *C. elegans* dosage compensation complex to target X chromosomes for transcriptional regulation of gene expression. Genes Dev. 25:499-515.

Pigino .G, K. H. Bui, A. Maheshwari, P. Lupetti, D. R. Diener, T. Ishikawa. 2011. Cryoelectron tomography of radial spokes in cilia and flagella. J Cell Biol. 195(4): 673-87.

Roguev, A., D. Schaft, A. Shevchenko, W. W. Pijnappel, M. Wilm, R. Aasland, and A. F. Stewart. 2001. The *Saccharomyces cerevisiae* Set1 complex includes an Ash2 homologue and methylates histone 3 lysine 4. Embo J. 20:7137-48.

Rual, J. F., K. Venkatesan, T. Hao, T. Hirozane-Kishikawa, A. Dricot, N. Li, G. F. Berriz, F. D. Gibbons, M. Dreze, N. Ayivi-Guedehoussou, et al. 2005. Towards a proteome-scale map of the human protein-protein interaction network. Nature. 437:1173-8.

Sarma, G. N., F. S. Kinderman, C. Kim, S. von Daake, L. Chen, B. C. Wang, and S. S. Taylor. 2010. Structure of D-AKAP2:PKA RI complex: insights into AKAP specificity and selectivity. Structure. 18:155-66.

Sarvan, S., V. Avdic, V. Tremblay, C. P. Chaturvedi, P. Zhang, S. Lanouette, A. Blais, J. S. Brunzelle, M. Brand, and J. F. Couture. Crystal structure of the trithorax group protein ASH2L reveals a forkhead-like DNA binding domain. Nat Struct Mol Biol. 18:857-9.

Satir, P. 1999. The cilium as a biological nanomachine. Faseb J. 13 Suppl 2:S235-7.

Scott, J. D., and T. Pawson. 2009. Cell signaling in space and time: where proteins come together and when they're apart. Science. 326:1220-4.

Silflow, C. D., M. LaVoie, L. W. Tam, S. Tousey, M. Sanders, W. Wu, M. Borodovsky, and P. A. Lefebvre. 2001. The Vfl1 Protein in *Chlamydomonas* localizes in a rotationally asymmetric pattern at the distal ends of the basal bodies. J Cell Biol. 153:63-74.

Smith, E., C. Lin, and A. Shilatifard. The super elongation complex (SEC) and MLL in development and disease. Genes Dev. 25:661-72.

South, P. F., I. M. Fingerman, D. P. Mersman, H. N. Du, and S. D. Briggs. 2010. A conserved interaction between the SDI domain of Bre2 and the Dpy-30 domain of Sdc1 is required for histone methylation and gene expression. J Biol Chem. 285:595-607.

Southall, S. M., P. S. Wong, Z. Odho, S. M. Roe, and J. R. Wilson. 2009. Structural basis for the requirement of additional factors for MLL1 SET domain activity and recognition of epigenetic marks. Mol Cell. 33:181-91.

Stelter, P., R. Kunze, D. Flemming, D. Hopfner, M. Diepholz, P. Philippsen, B. Bottcher, and E. Hurt. 2007. Molecular basis for the functional interaction of dynein light chain with the nuclear-pore complex. Nat Cell Biol. 9:788-96.

Steward, M. M., J. S. Lee, A. O'Donovan, M. Wyatt, B. E. Bernstein and A. Shilatifard. 2006. Molecular regulation of H3K4 trimethylation by ASH2L, a shared subunit of MLL complexes. Nat Struct Mol Biol. 13(9):852-4.

Stoller, J. Z., L. Huang, C. C. Tan, F. Huang, D. D. Zhou, J. Yang, B. D. Gelb, and J. A. Epstein. 2010. Ash2l interacts with Tbx1 and is required during early embryogenesis. Exp Biol Med (Maywood). 235:569-76.

Takahashi, Y. H., G. H. Westfield, A. N. Oleskie, R. C. Trievel, A. Shilatifard, and G. Skiniotis. Structural analysis of the core COMPASS family of histone H3K4 methylases from yeast to human. Proc Natl Acad Sci USA. 108:20526-31.

Wang, L., R. K. Sunahara, A. Krumins, G. Perkins, M. L. Crochiere, M. Mackey, S. Bell, M. H. Ellisman, and S. S. Taylor. 2001. Cloning and mitochondrial localization of full-length D-AKAP2, a protein kinase A anchoring protein. Proc Natl Acad Sci USA. 98:3220-5.

Wang, X., Z. Lou, X. Dong, W. Yang, Y. Peng, B. Yin, Y. Gong, J. Yuan, W. Zhou, M. Bartlam, X. Peng, and Z. Rao. 2009. Crystal structure of the C-terminal domain of human DPY-30-like protein: A component of the histone methyltransferase complex. J Mol Biol. 390:530-7.

Warner, F. D., and P. Satir. 1974. The structural basis of ciliary bend formation. Radial spoke positional changes accompanying microtubule sliding. J Cell Biol. 63:35-63.

Welch, E. J., B. W. Jones, and J. D. Scott. 2010. Networking with AKAPs: context-dependent regulation of anchored enzymes. Mol Interv. 10:86-97.

Wei, M., P. Sivadas, H. A. Owen, D. R. Mitchell, and P. Yang. 2010. Chlamydomonas mutants display reversible deficiencies in flagellar beating and axonemal assembly. Cytoskeleton (Hoboken). 67:71-80.

Williams, B. D., M. A. Velleca, A. M. Curry, and J. L. Rosenbaum. 1989. Molecular cloning and sequence analysis of the Chlamydomonas gene coding for radial spoke protein 3: flagellar mutation pf-14 is an ochre allele. J Cell Biol. 109:235-45.

Wirschell, M., F. Zhao, C. Yang, P. Yang, D. Diener, A. Gaillard, J. L. Rosenbaum, and W. S. Sale. 2008. Building a radial spoke: flagellar radial spoke protein 3 (RSP3) is a dimer. Cell Motil Cytoskeleton. 65:238-48.

Witman, G. B., J. Plummer, and G. Sander. 1978. Chlamydomonas flagellar mutants lacking radial spokes and central tubules. Structure, composition, and function of specific axonemal components. J Cell Biol. 76:729-47.

Xia, B., A. Joubert, B. Groves, K. Vo, D. Ashraf, D. Djavaherian, J. Awe, Y. Xiong, J. Cherfils, and D. Ma. 2010. Modulation of cell adhesion and migration by the histone methyltransferase subunit mDpy-30 and its interacting proteins. PLoS One. 5:e11771.

Xu, Z., Q. Gong, B. Xia, B. Groves, M. Zimmermann, C. Mugler, D. Mu, B. Matsumoto, M. Seaman, and D. Ma. 2009. A role of histone H3 lysine 4 methyltransferase components in endosomal trafficking. J Cell Biol. 186: 343-53.

Yang, C., H. A. Owen, and P. Yang. 2008. Dimeric heat shock protein 40 binds radial spokes for generating coupled power strokes and recovery strokes of 9+2 flagella. J Cell Biol. 180:403-15.

Yang, C., and P. Yang. 2006. The flagellar motility of Chlamydomonas pf25 mutant lacking an AKAP-binding protein is overtly sensitive to medium conditions. Mol Biol Cell. 17:227-38.

Yang, P., D. R. Diener, C. Yang, T. Kohno, G. J. Pazour, J. M. Dienes, N. S. Agrin, S. M. King, W. S. Sale, R. Kamiya, J. L. Rosenbaum, and G. B. Witman. 2006. Radial spoke proteins of Chlamydomonas flagella. J Cell Sci. 119:1165-74.

Yang, P., C. Yang and W S Sale. 2006. Flagellar radial spoke protein 2 is a calmodulin binding protein required for motility in Chlamydomonas reinhardtii. Eukaryotic Cell. 3: 72-81.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/ or variation of the concepts herein disclosed may be resorted to by those skilled in the art, and that such modifications and variations are considered to be within the scope of this invention.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A method comprising administering to a cell that expresses dumpy-30 protein (Dpy-30) a peptide or peptidomimetic, wherein the peptide or peptidomimetic binds to Dpy-30 and comprises the amino sequence of SEQ ID NO:2, SEQ ID NO:4, or SEQ ID NO:6, and wherein the peptide or peptidomimetic is no more than 50 amino acids in length.

2. The method of claim 1, wherein the cell is exhibiting hyperplasia or the cell is a cancerous cell.

3. The method of claim 1, wherein prior to being administered the peptide or peptidomimetic is formulated as a pharmaceutical composition in order to facilitate intercellular uptake.

4. The method of claim 3, wherein the peptide or peptidomimetic is formulated as a liposomal or micelle formulation.

5. A method comprising administering to a cancerous cell a peptide or peptidomimetic, wherein the peptide or peptidomimetic binds to dumpy-30 protein (Dpy-30) and comprises the amino acid sequence of SEQ ID NO:2, SEQ ID NO:4, or SEQ ID NO:6, and wherein the peptide or peptidomimetic is no more than 50 amino acids in length.

6. The method of claim 5, wherein prior to being administered the peptide or peptidomimetic is formulated as a pharmaceutical composition in order to facilitate intercellular uptake.

7. The method of claim 6, wherein the peptide or peptidomimetic is formulated as a liposomal or micelle formulation.

* * * * *